(12) United States Patent
Stripecke et al.

(10) Patent No.: US 12,054,529 B2
(45) Date of Patent: Aug. 6, 2024

(54) CHIMERIC ANTIGEN RECEPTOR AND CAR-T CELLS THAT BIND A HERPES VIRUS ANTIGEN

(71) Applicants: MEDIZINISCHE HOCHSCHULE HANNOVER, Hannover (DE); HELMHOLTZ ZENTRUM MÜNCHEN—DEUTSCHES FORSCHUNGSZENTRUM FÜR GESUNDHEIT UND UMWELT (GMBH), Neuherberg (DE)

(72) Inventors: Renata Stripecke, Hannover (DE); Constanze Slabik, Heidelberg (DE); Reinhard Zeidler, Olching (DE); Wolfgang Hammerschmidt, Munich (DE)

(73) Assignees: MEDIZINISCHE HOCHSCHULE HANNOVER, Hannover (DE); HELMHOLTZ ZENTRUM MÜNCHEN—DEUTSCHES FORSCHUNGSZENTRUM FÜR GESUNDHEIT UND UMWELT (GMBH), Neuherberg (DE)

( * ) Notice: Subject to any disclaimer, the term of this patent is extended or adjusted under 35 U.S.C. 154(b) by 961 days.

(21) Appl. No.: 17/048,928

(22) PCT Filed: Apr. 17, 2019

(86) PCT No.: PCT/EP2019/059928
§ 371 (c)(1),
(2) Date: Oct. 19, 2020

(87) PCT Pub. No.: WO2019/201995
PCT Pub. Date: Oct. 24, 2019

(65) Prior Publication Data
US 2021/0230245 A1 Jul. 29, 2021

(30) Foreign Application Priority Data
Apr. 20, 2018 (EP) .................................... 18168410

(51) Int. Cl.
| | | |
|---|---|---|
| C07K 14/725 | (2006.01) | |
| A61K 35/17 | (2015.01) | |
| A61P 31/22 | (2006.01) | |
| C07K 14/705 | (2006.01) | |
| C07K 16/08 | (2006.01) | |
| A61K 39/00 | (2006.01) | |

(52) U.S. Cl.
CPC .......... C07K 14/7051 (2013.01); A61K 35/17 (2013.01); A61P 31/22 (2018.01); C07K 14/70517 (2013.01); C07K 14/70521 (2013.01); C07K 14/70578 (2013.01); C07K 16/087 (2013.01); *A61K 2039/505* (2013.01)

(58) Field of Classification Search
CPC .......... C07K 14/7051; C07K 14/70517; C07K 14/70521; C07K 14/70578; C07K 16/087; A61P 31/22; A61K 35/17; A61K 2039/505
See application file for complete search history.

(56) References Cited

FOREIGN PATENT DOCUMENTS

| CN | 107922489 A * | 4/2018 | ............. A61K 35/17 |
|---|---|---|---|
| WO | WO 2017/172981 A2 | 10/2017 | |

OTHER PUBLICATIONS

Khyatti et al., Binding of the endogenously expressed Epstein-Barr virus (EBV) envelope glycoprotein gp350 with the viral receptor masks the major EBV-neutralizing epitope and affects gp350-specific ADCC, Journal of Leukocyte Biology (1998), 64: 192-197 (Year: 1998).*
Janeway CA Jr, Travers P, Walport M, et al. Immunobiology: The Immune System in Health and Disease. 5th edition. New York: Garland Science; 2001. The structure of a typical antibody molecule. Available from: https://www.ncbi.nlm.nih.gov/books/NBK27144/ (Year: 2001).*
(Ahsan et al., Epstein-Barr Virus Transforming Protein LMP1 Plays a Critical Roles in Virus Production, Journal of Virology. (2005), 79(7): 4415-4424). (Year: 2005).*

(Continued)

*Primary Examiner* — Evelyn Y Pyla
*Assistant Examiner* — Katherine R Small
(74) *Attorney, Agent, or Firm* — Knobbe, Martens, Olson and Bear, LLP

(57) ABSTRACT

An isolated chimeric antigen receptor (CAR) polypeptide, wherein the CAR includes an extracellular antigen-binding domain, including an antibody or antibody fragment that binds to a protein encoded by a herpes virus, or to a protein complex including the protein (herpes virus antigen), wherein the herpes virus antigen is present on the surface of a human cell that is latently infected with said herpes virus and supports the lytic phase of viral replication. The invention further relates to a nucleic acid molecule encoding the CAR of the invention, a genetically modified immune cell, preferably a T cell, expressing the CAR of the invention and the use of the cell in the treatment of a medical disorder associated with human herpesvirus, such as herpes virus-associated cancers, chronic active herpes virus infections or primary herpes virus infections. In preferred embodiments the herpes virus is Epstein-Barr virus (EBV) and a preferred herpes virus antigen target of the CAR is the EBV glycoprotein 350/220 (gp350/gp220).

13 Claims, 16 Drawing Sheets
Specification includes a Sequence Listing.

(56) References Cited

OTHER PUBLICATIONS

Smith, Sequence Variation within Botulinum Neurotoxin Serotypes Impacts Antibody Binding and Neutralization, Infection and Immunity (2005), 73(9): 5450-5457. (Year: 2005).*
Chen et al., A Human Fab-Based Immunoconjugate Specific for the LMP1 Extracellular Domain Inhibits Nasopharyngeal Carcinoma Growth In Vitro and In Vivo, Mol. Cancer Ther. (2012), 11(3):594-603 (Year: 2012).*
Chia et al., Adoptive T-cell Transfer and Chemotherapy in the First-line Treatment of Metastatic and/or Locally Recurrent Nasopharyngeal Carcinoma, Molecular Therapy. (2013), p. 1-8 (Year: 2013).*
Chen et al., Fusion Protein Linkers: Property, Design and Functionality, Adv Drug Deliv Rev. (2013), 65(10): 1357-1369 (Year: 2013).*
Daniyan and Brentjens, At the Bench: Chimeric antigen receptor (CAR) T cell therapy for the treatment of B cell Malignancies, Journal of Leukocyte Biology. (2016), 100: 1255-1264 (Year: 2016).*
International Search Report and Written Opinion, from PCT/EP2019/059928, mailed Jul. 3, 2019.
Tang, X., et al., 2014 "T cells expressing a LMP1-specific chimeric antigen receptor mediate antitumor effects against LMP1-positive nasopharyngeal carcinoma cells in vitro and in vivo", *Journal of Biomedical Research*, vol. 28, No. 6: 468-475.
Von Laer, D., et al., 2009 "Antiviral gene therapy", Handbook of Experimental Pharmacology, Springer Verlag, Berlin, DE, vol. 189: 265-297.
Danisch, S., et al., 2018 "CAR-T Cells Targeting gp350 Recognize Immortalized Cells Latently Infected with EBV", *Blood*, vol. 132: 4540.
Adhikary, Dinesh, et al., "Control of Epstein-Barr virus infection in vitro by T helper cells specific for virion glycoproteins," The Journal of Experimental Medicine, vol. 203, No. 4, Apr. 17, 2006, 995-1006.
Al-Lazikani, Bissan, et al., "Standard Conformations for the Canonical Structures of Immunoglobulins," J. Mol. Biol. (1997) 273, 927-948.
Antsiferova, Olga, et al., "Adoptive Transfer of EBV Specific CD8+ T Cell Clones Can Transiently Control EBV Infection in Humanized Mice," PLOS Pathogens, Aug. 2014, vol. 10, Issue 8, e1004333.
Daenthanasanmak, Anusara, et al., "Engineered dendritic cells from cord blood and adult blood accelerate effector T cell immune reconstitution against HCMV," Molecular Therapy—Methods & Clinical Development (2014) 1, 14060.
Dotti, Gianpietro, et al., "Design and development of therapies using chimeric antigen receptor-expressing T cells," Immunological Reviews 2014, vol. 257: 107-126.
Eyquem, Justin, et al., "Targeting a CAR to the TRAC locus with CRISPR/Cas9 enhances tumour rejection," Nature, vol. 543, Mar. 2, 2017.
Full, Florian, et al., "T Cells Engineered with a Cytomegalovirus-Specific Chimeric Immunoreceptor," Journal of Virology, Apr. 2010, vol. 84, No. 8, p. 4083-4088.
Hutt-Fletcher and Lindsey M., "EBV glycoproteins: where are we now?" Future Virol. 2015; 10(10): 1155-1162.
Mamonkin, Maksim, et al., "A T-cell-directed chimeric antigen receptor for the selective treatment of T-cell malignancies," Blood, Aug. 20, 2015, vol. 126, No. 8: 983-992.
Mátés, Lajos, et al., "Molecular evolution of a novel hyperactive Sleeping Beauty transposase enables robust stable gene transfer in vertebrates," Nature Genetics, vol. 41, No. 6: 753-761, Jun. 2009.
Papadopoulou, Anastasia, et al., "Activity of Broad-Spectrum T Cells as Treatment for AdV, EBV, CMV, BKV, and HHV6 Infections after HSCT," Science Translational Medicine, Jun. 25, 2014, vol. 6, Issue 242.
Queen, Cary, et al., "A humanized antibody that binds to the interleukin 2 receptor," Proc. Natl. Acad. Sci. USA, vol. 86, pp. 10029-10033, Dec. 1989.
Salguero, Gustavo, et al., "Dendritic Cell-Mediated Immune Humanization of Mice: Implications for Allogeneic and Xenogeneic Stem Cell Transplantation," The Journal of Immunology, 2014: 192:4636-4647.
Tang, Xiaojun, et al., "T cells expressing a LMP1-specific chimeric antigen receptor mediate antitumor effects against LMP1-positive nasopharyngeal carcinoma cells in vitro and in vivo," The Journal of Biomedical Research, 2014, 28(6):468-475.
Von Laer, D., et al., "Antiviral Gene Therapy", Antiviral Strategies, Handbook of Experimental Pharmacology, Springer-Verlag Berlin Heidelberg 2009, 189: 265-297.
Weekes, Michael P., et al., "Quantitative Temporal Viromics: An Approach to Investigate Host-Pathogen Interaction," Cell 157, 1460-1472, Jun. 5, 2014.
Wu et al., "From therapeutic antibodies to chimeric antigen receptors (CARs): making better CARs based on antigen-binding domain," Expert Opinion on Biological Therapy, 16:12, 1469-1478 (2016).

* cited by examiner

Fig. 1
A 7A1 and 6G4 monoclonal Abs neutralize infection of Raji cells with EBV
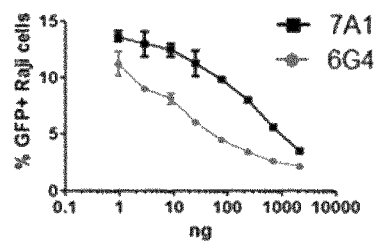
B Schematic representation of CAR constructs
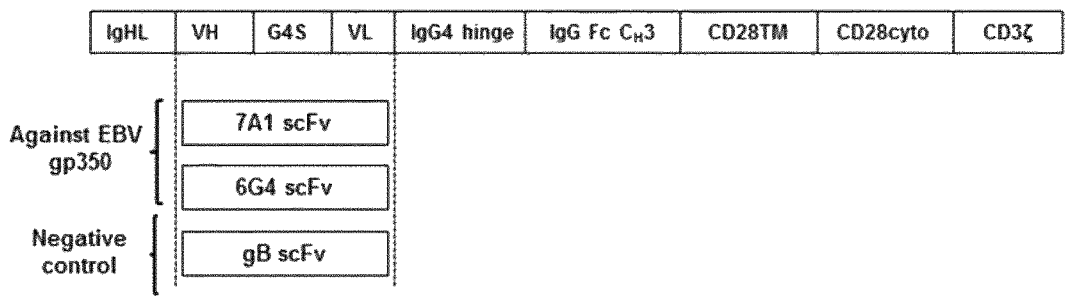
C Generation of CAR-T cells
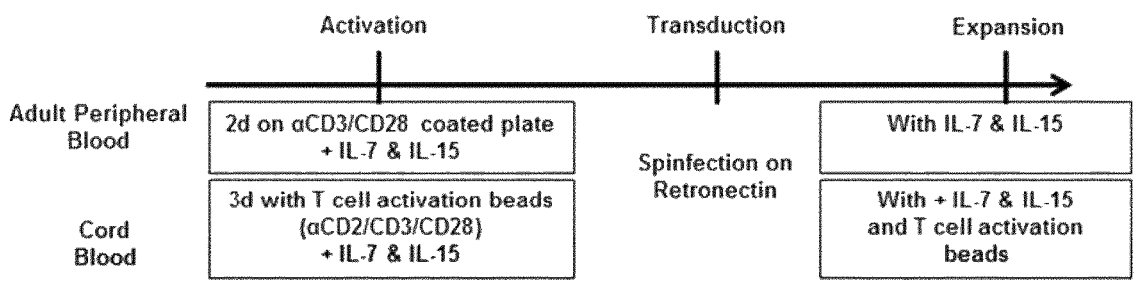
D Adult peripheral blood T cells
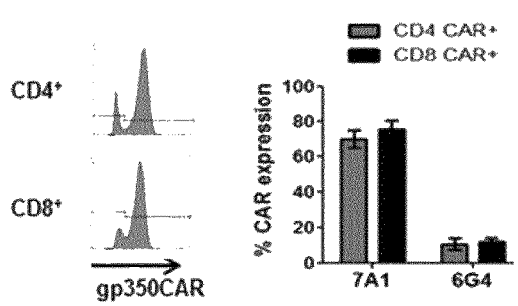
E Cord blood T cells
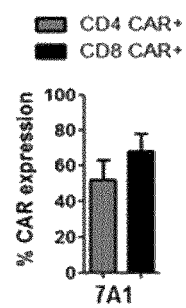

Fig. 1 (cont.)
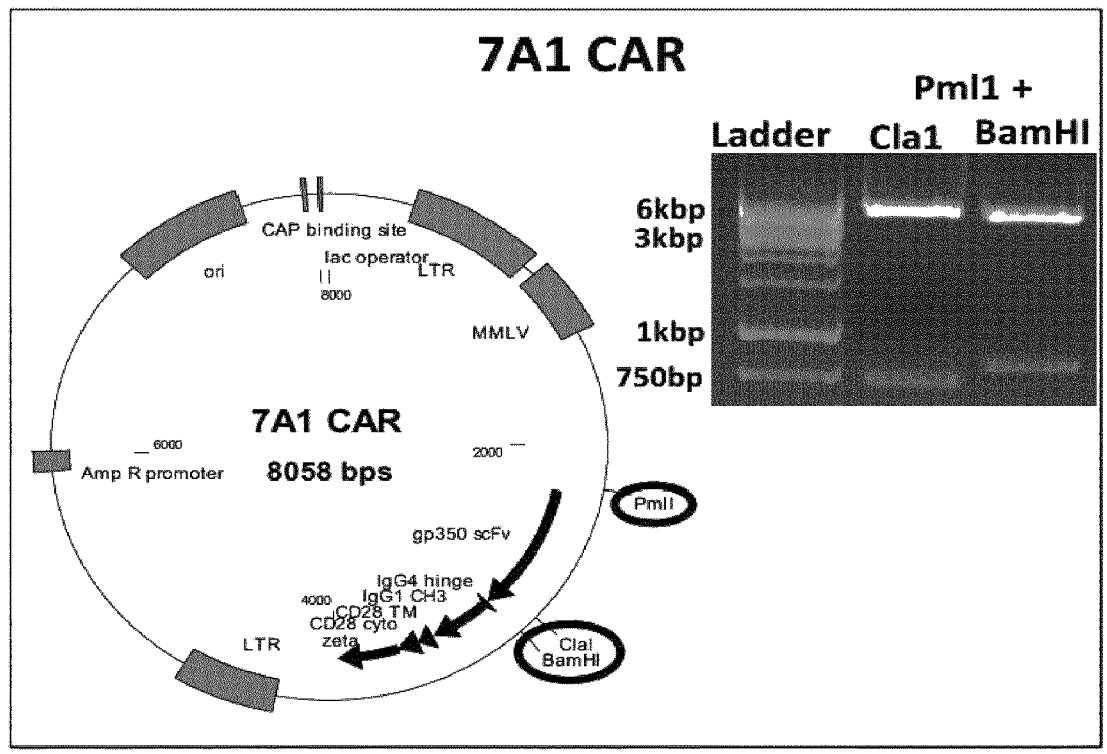
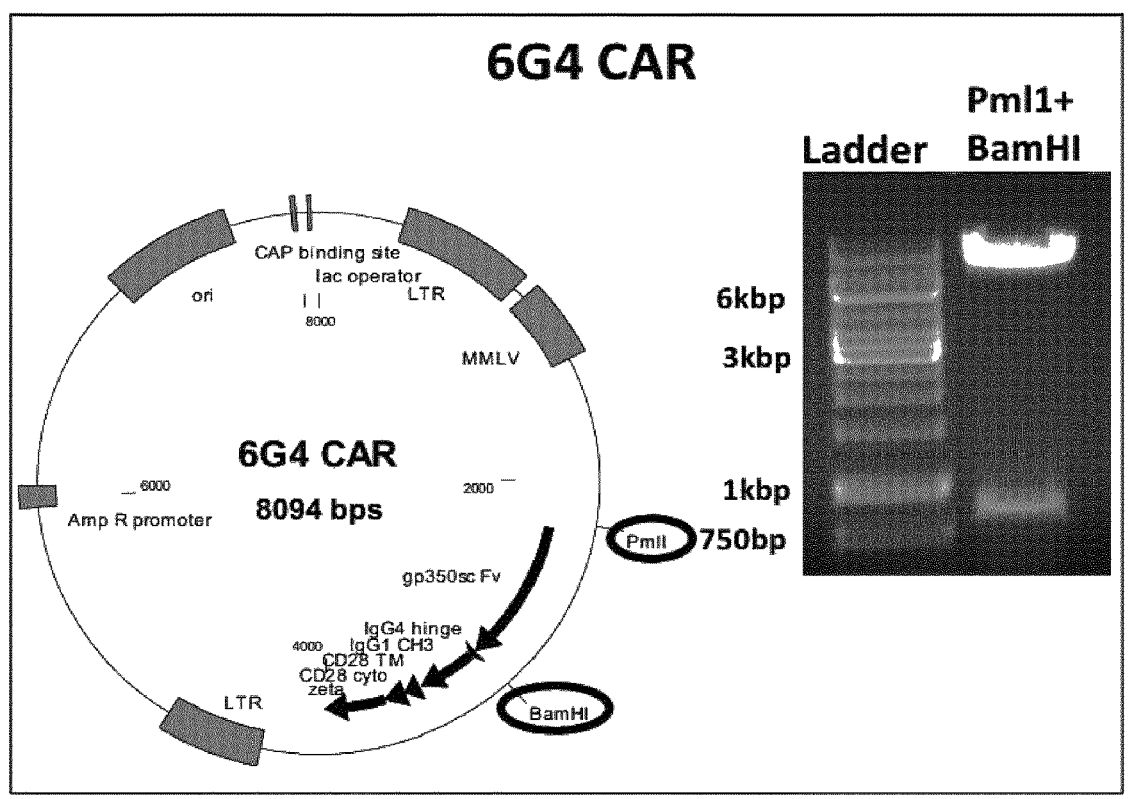

Fig. 2
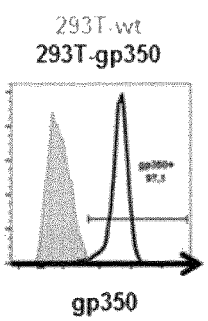
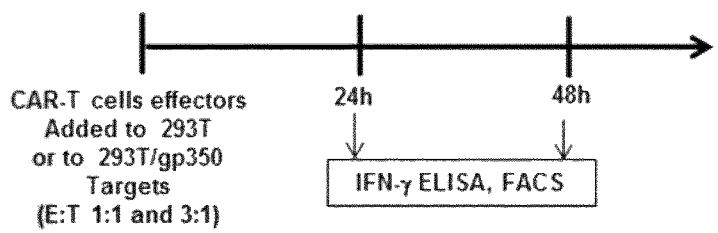
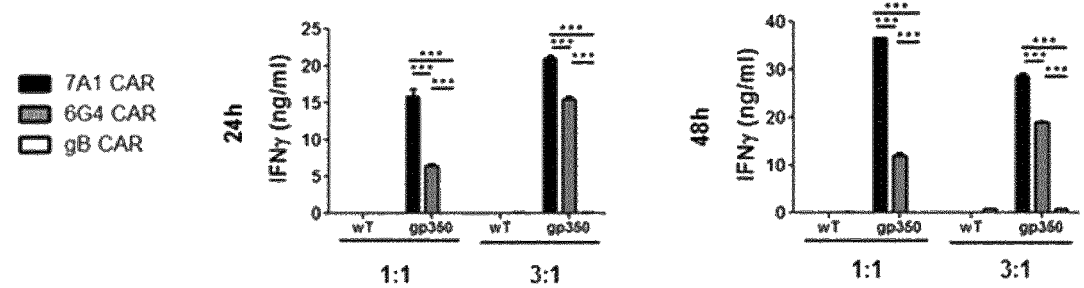
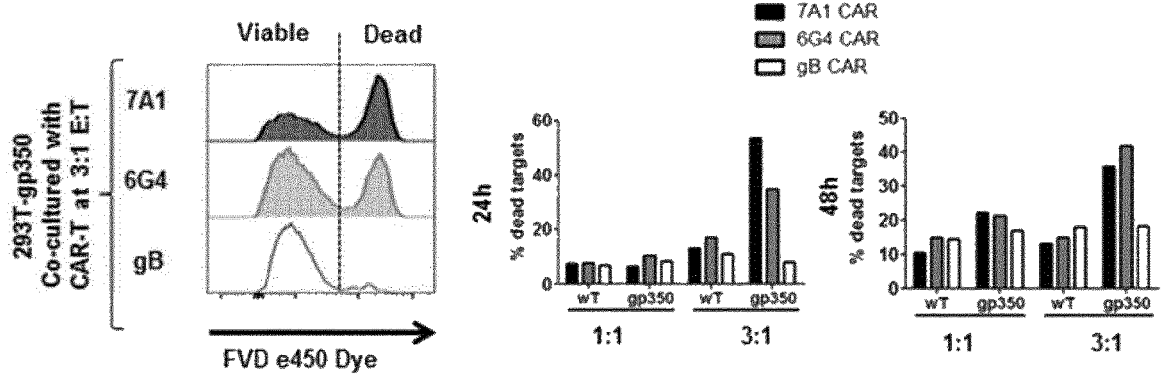
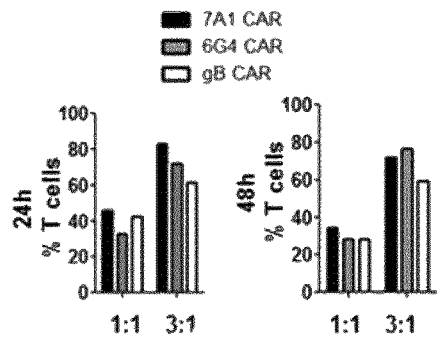
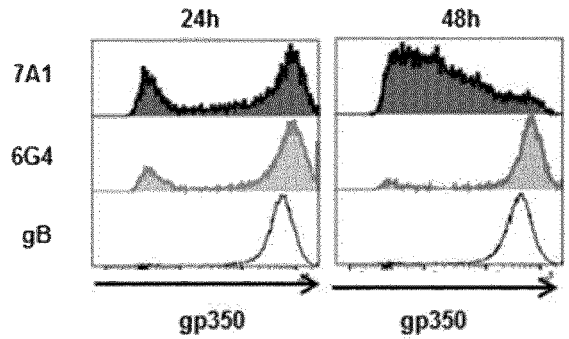

Fig. 4
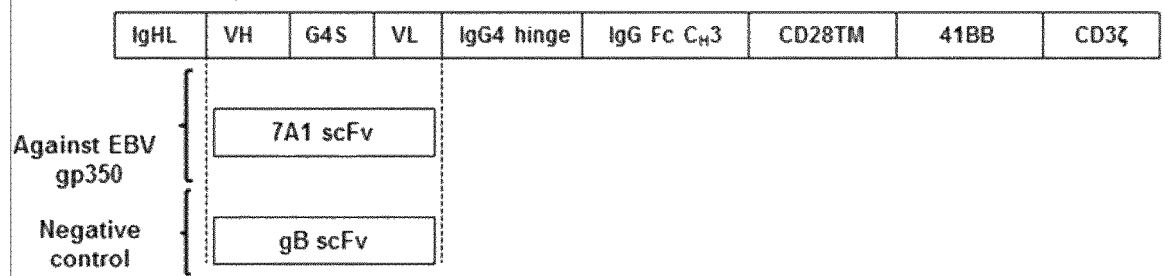
A Schematic representation of CAR constructs
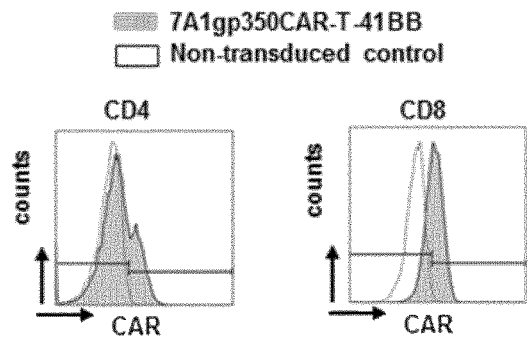
B Expression of CAR on T cells
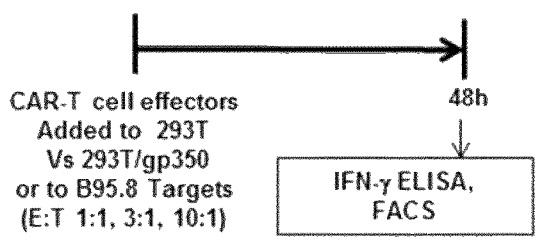
C Experimental scheme
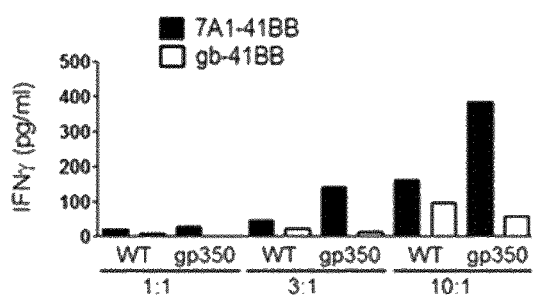
D Detection of IFN-γ after 293T co-culture
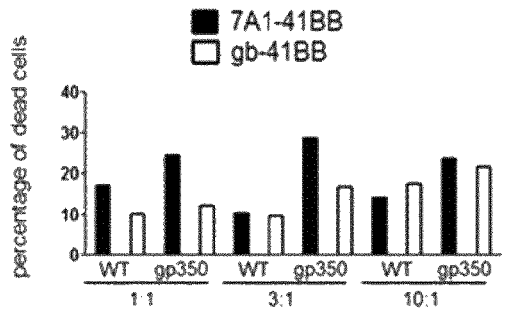
E Detection of dead 293T targets
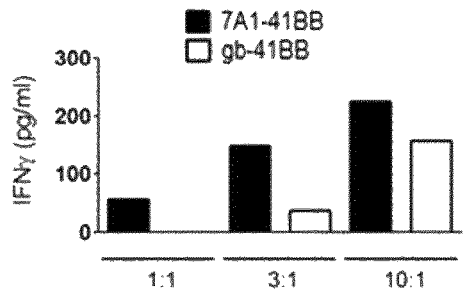
F Detection of IFN-γ after B95.8 co-culture Fig. 6
A Experimental scheme
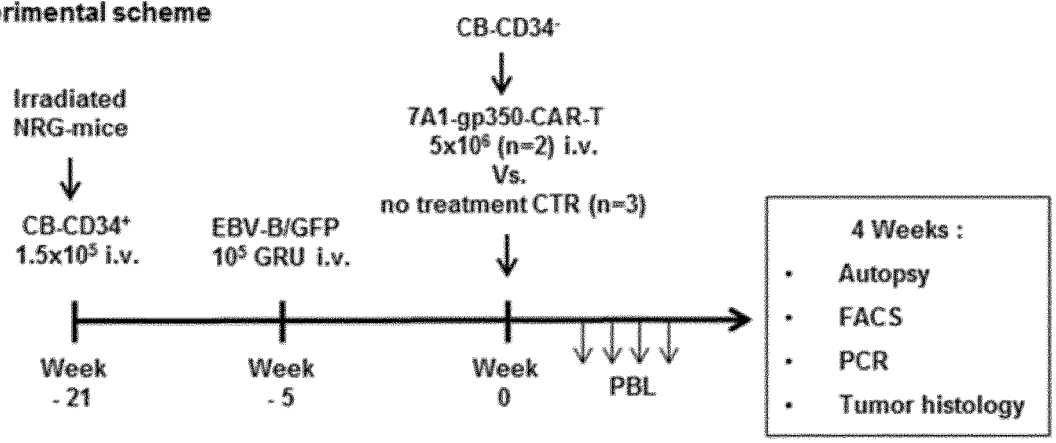
B CAR detection in blood
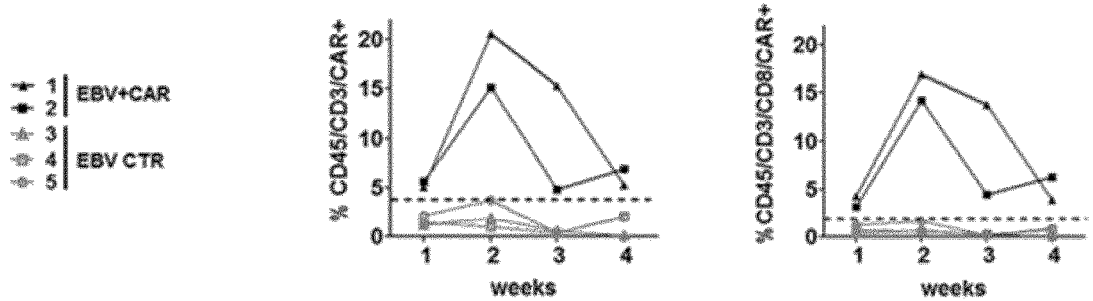
C CAR detection in spleen and tumors
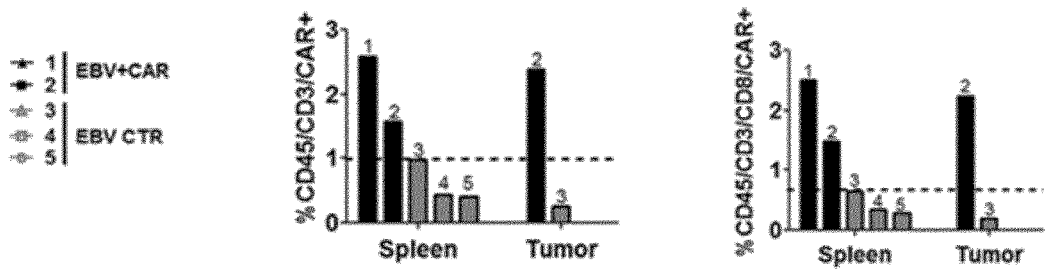
D EBV DNA copies in spleen and tumors
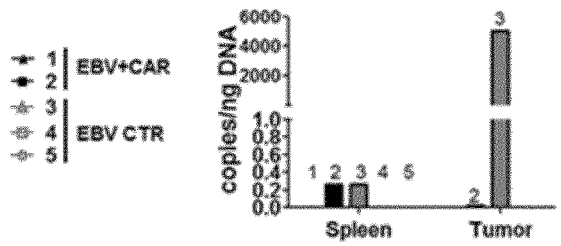
E EBER staining of splenic tumors
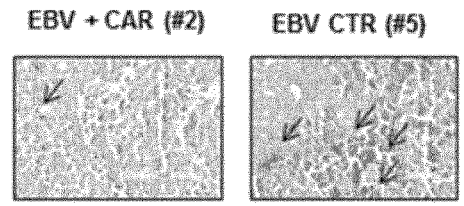

Fig. 7
A Experimental scheme
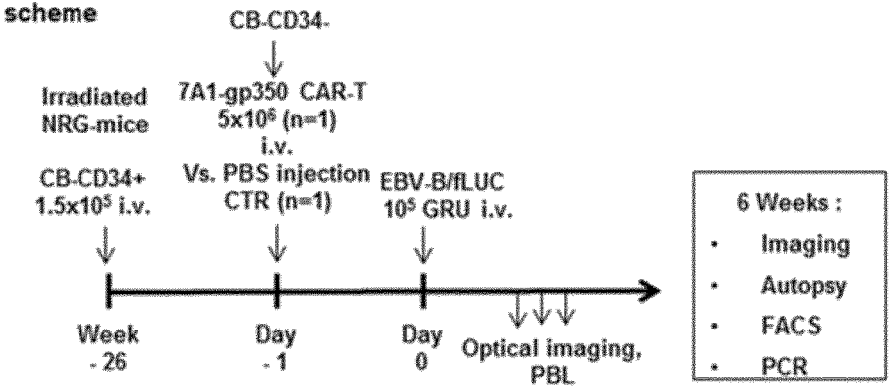
B Sequential bioluminescence optical imaging
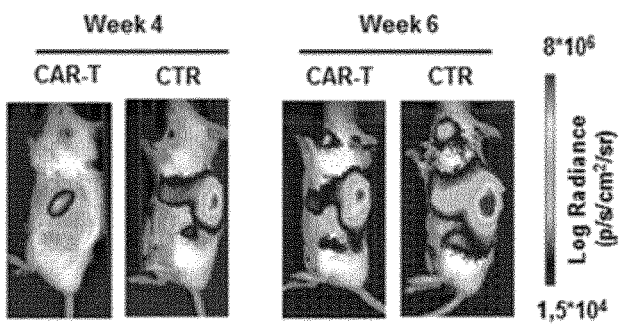
C Signal detection in spleen region over time
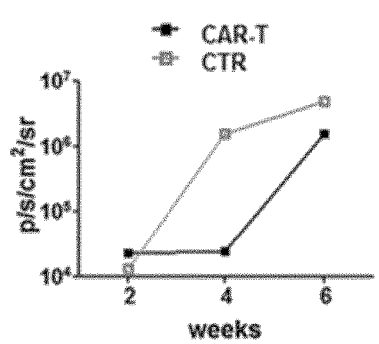
D Signal in liver and salivary glands
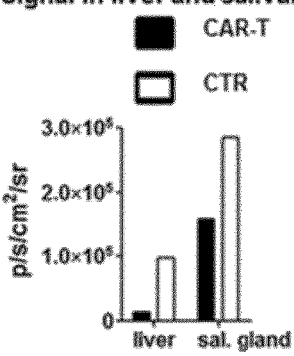
E Detection of CAR-T cells in blood
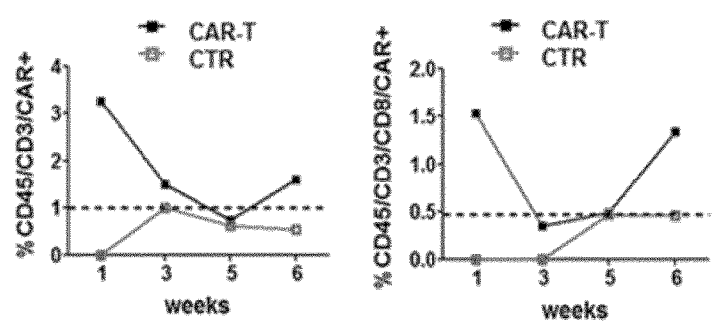
F Detection of CAR-T cells in spleen and bone marrow
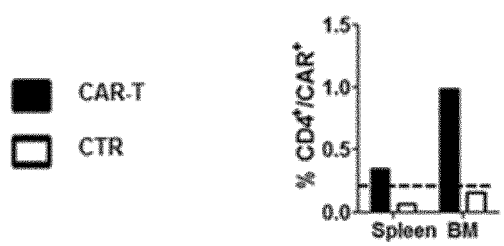

Fig. 8

| # | Name | Antibody origin | CAR | | | Vector Type | Tested in | |
|---|---|---|---|---|---|---|---|---|
| | | | scFv | Spacer | Signaling | | 293T | T cells |
| 1 | Gp350CAR6 B(S.28.z) | 6G4 | IgHL-VH-G4S-VL | IgG Fc $C_H3$ | CD28 – CD3ζ | RV, LV | x x | x x |
| 2 | Gp350CAR6 H(S.28.z) | 6G4 | pelB-VH-Linker-VL-Tag | IgG Fc $C_H3$ | CD28 – CD3ζ | RV | x x | |
| 3 | Gp350CAR7 B(S.28.z) | 7A1 | IgHL-VH-G4S-VL | IgG Fc $C_H3$ | CD28 – CD3ζ | RV, LV | x x | x x |
| 4 | Gp350CAR7 H(S.28.z) | 7A1 | pelB-VH-Linker-VL-Tag | IgG Fc $C_H3$ | CD28 – CD3ζ | RV | x | |
| 5 | Gp350CAR6 B(L.28.z) | 6G4 | IgHL-VH-G4S-VL | IgG Fc $C_H3$-$C_H2$ | CD28 – CD3ζ | RV | x | |
| 6 | Gp350CAR6 H(L.28.z) | 6G4 | pelB-VH-Linker-VL-Tag | IgG Fc $C_H3$-$C_H2$ | CD28 – CD3ζ | RV | x | |
| 7 | Gp350CAR7 B(L.28.z) | 7A1 | IgHL-VH-G4S-VL | IgG Fc $C_H3$-$C_H2$ | CD28 – CD3ζ | RV | x | |
| 8 | Gp350CAR7 H(L.28.z) | 7A1 | pelB-VH-Linker-VL-Tag | IgG Fc $C_H3$-$C_H2$ | CD28 – CD3ζ | RV | x | |
| 9 | Gp350CAR6 B(L.BB.z) | 6G4 | IgHL-VH-G4S-VL | IgG Fc $C_H3$-$C_H2$ | 4-1BB – CD3ζ | RV, LV | x x | x |
| 10 | Gp350CAR6 H(L.BB.z) | 6G4 | pelB-VH-Linker-VL-Tag | IgG Fc $C_H3$-$C_H2$ | 4-1BB – CD3ζ | RV | x | |
| 11 | Gp350CAR7 B(L.BB.z) | 7A1 | IgHL-VH-G4S-VL | IgG Fc $C_H3$-$C_H2$ | 4-1BB – CD3ζ | RV, LV | x x | x |
| 12 | Gp350CAR7 H(L.BB.z) | 7A1 | pelB-VH-Linker-VL-Tag | IgG Fc $C_H3$-$C_H2$ | 4-1BB – CD3ζ | RV | x | |

Fig. 9
A. Experimental Scheme
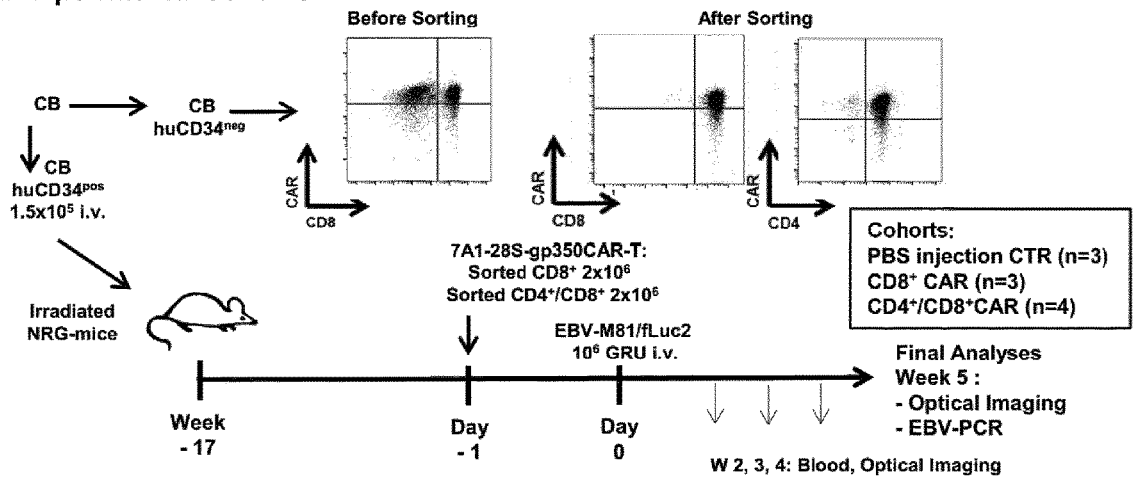
B. Human CD45+ cells in blood
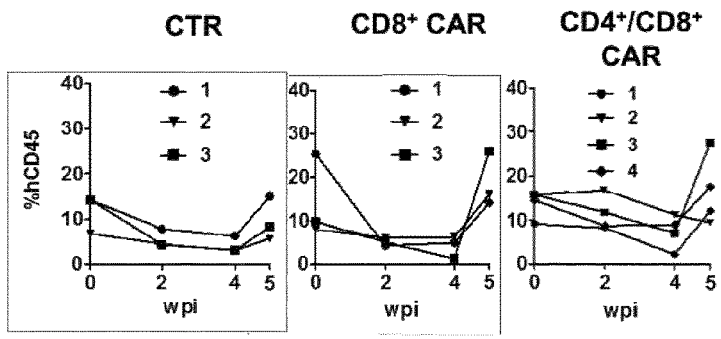
C. Human CD8+ cells in blood
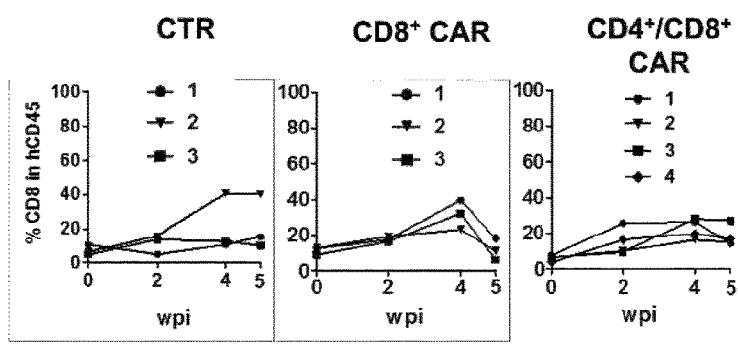

Fig. 9 (cont.)
D. Live optical imaging left view
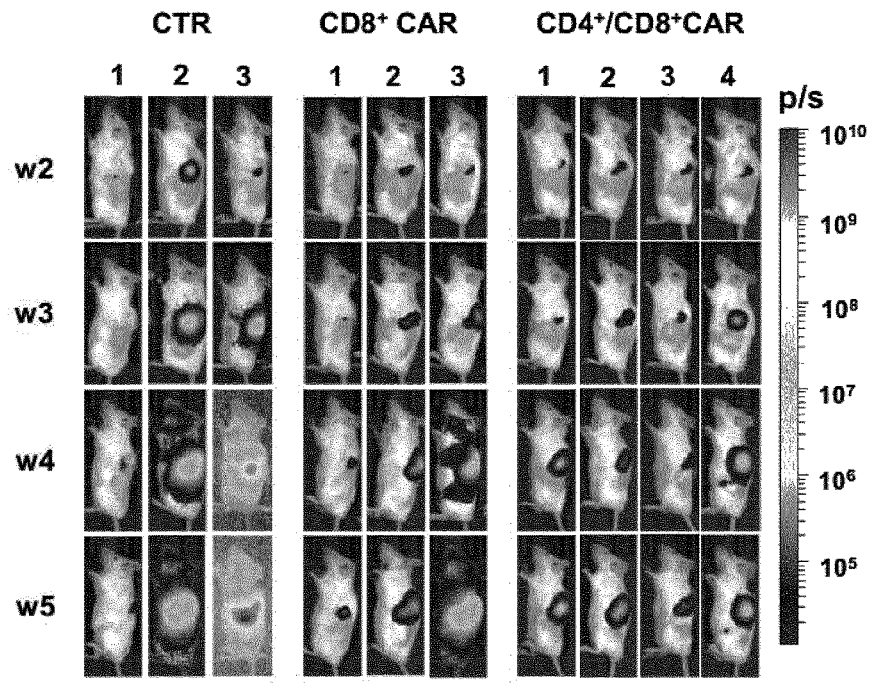
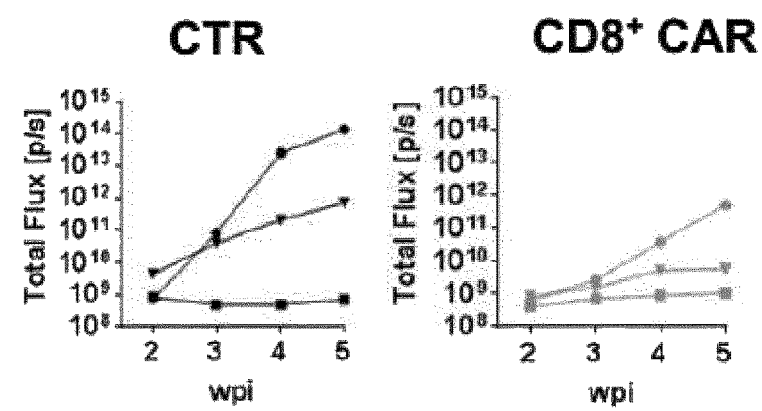
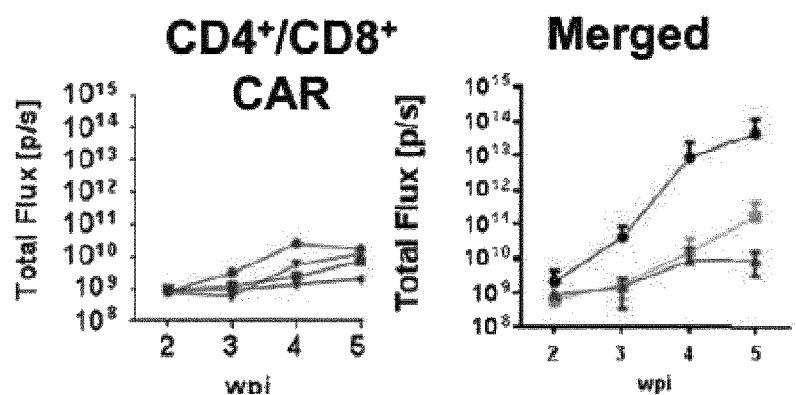

Fig. 9 (cont.)
E. EBV-PCR
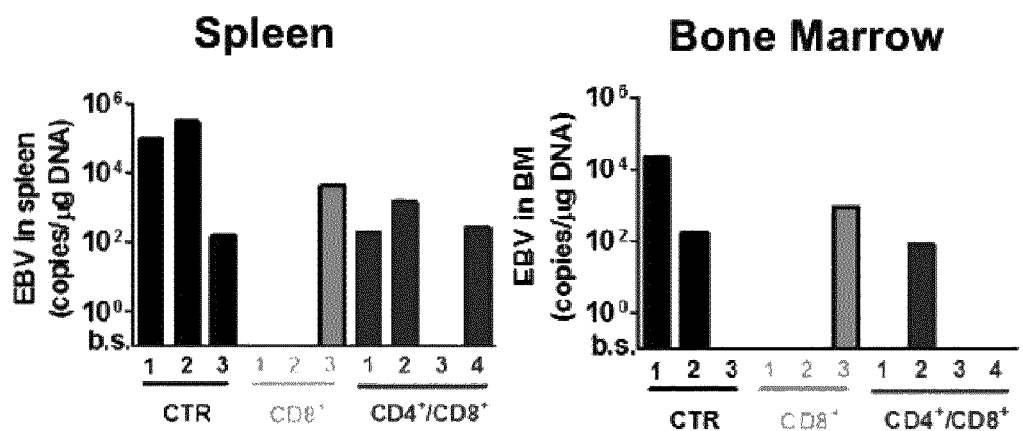
F. Flux and PCR correlation analyses
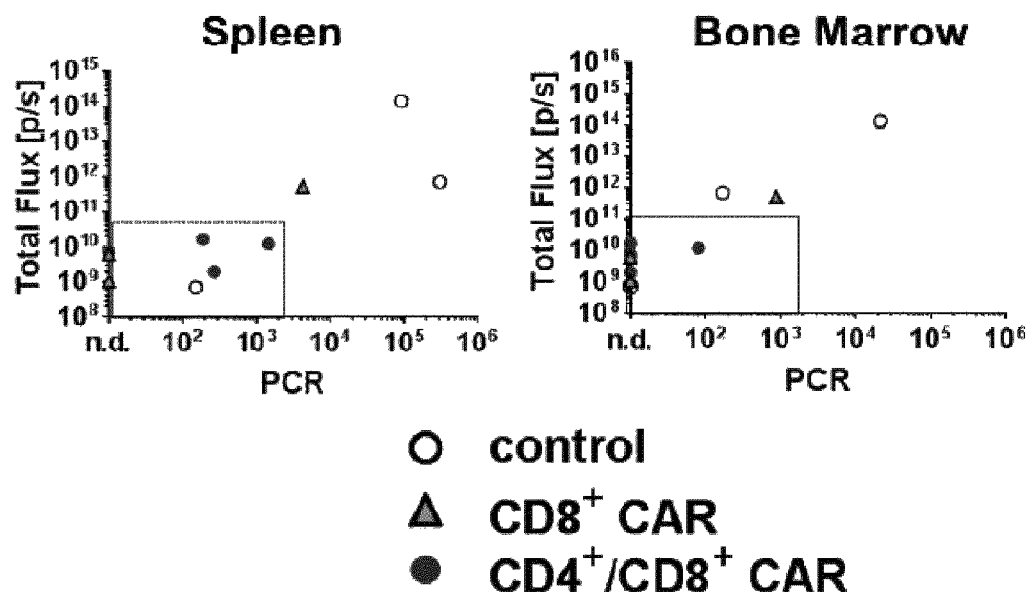
○ control
▲ CD8$^+$ CAR
● CD4$^+$/CD8$^+$ CAR Fig. 10
A. Experimental Scheme
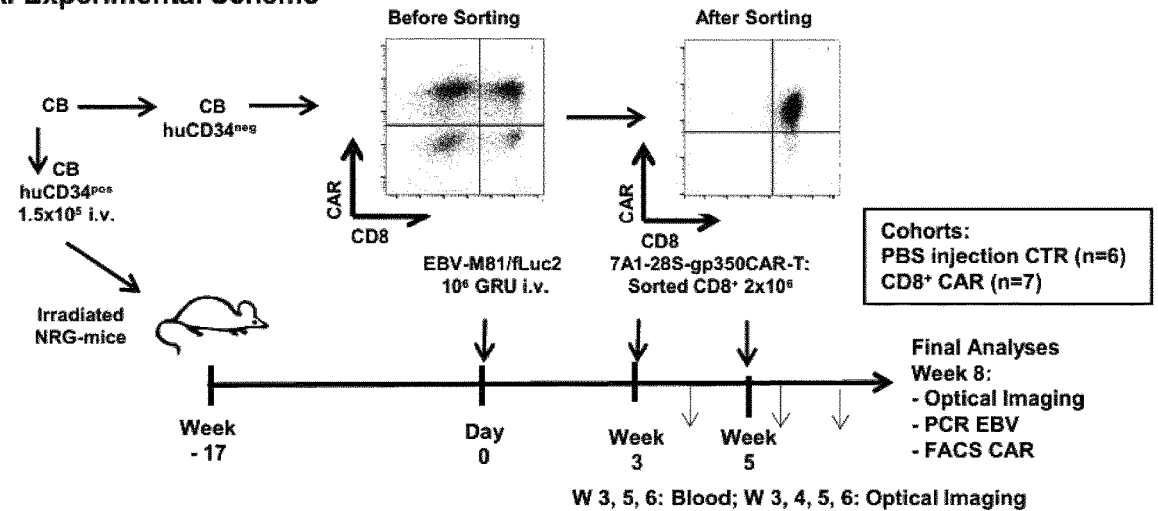
B. Human CD45⁺ cells in blood
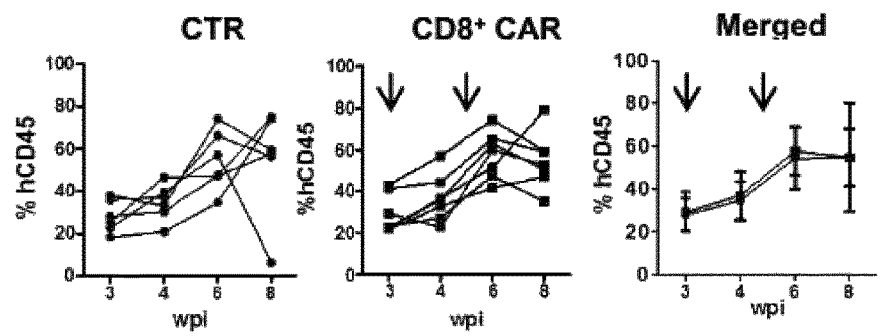
C. Human CD8⁺ cells in blood
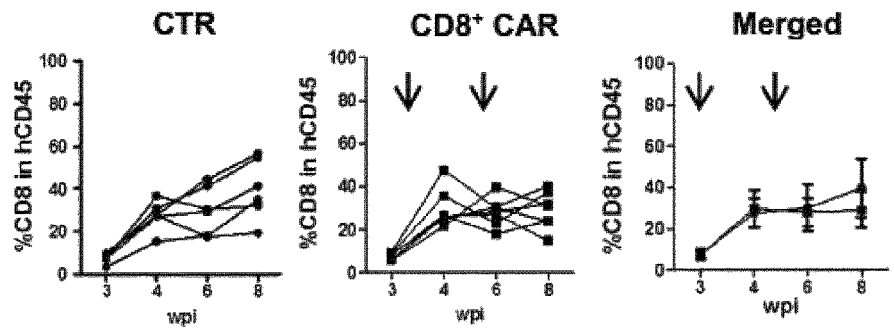

Fig. 10 (cont.)
D. Live Optical Imaging
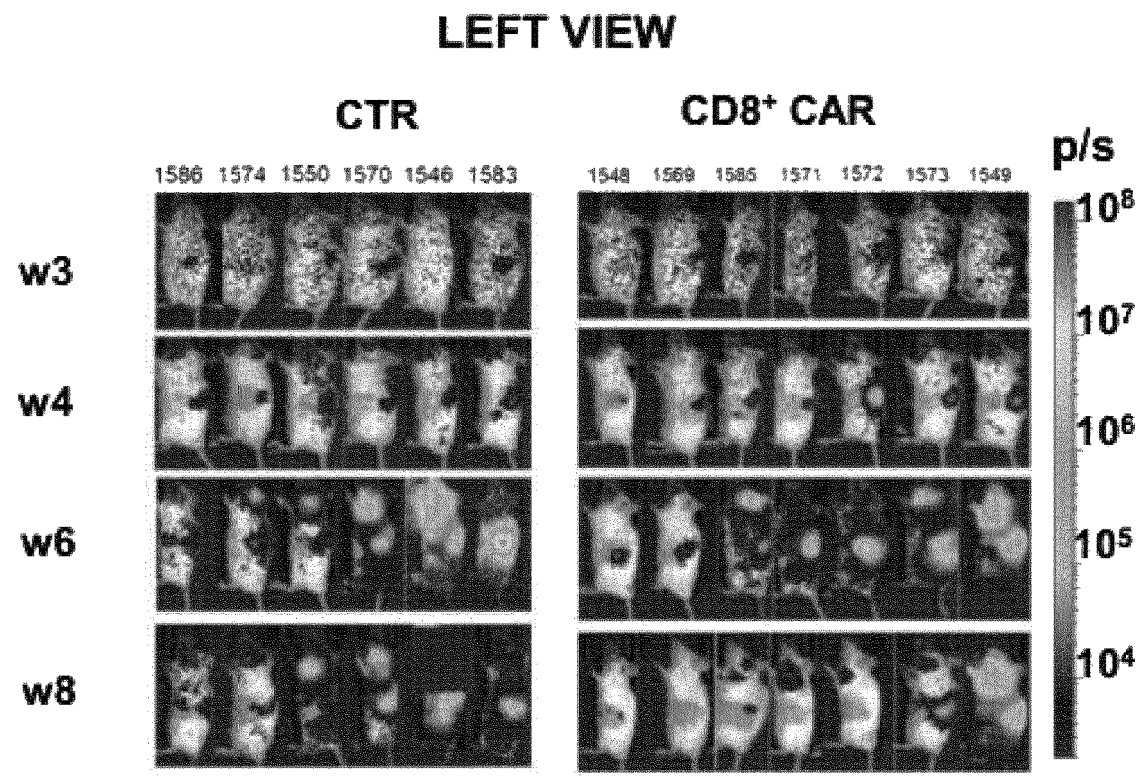
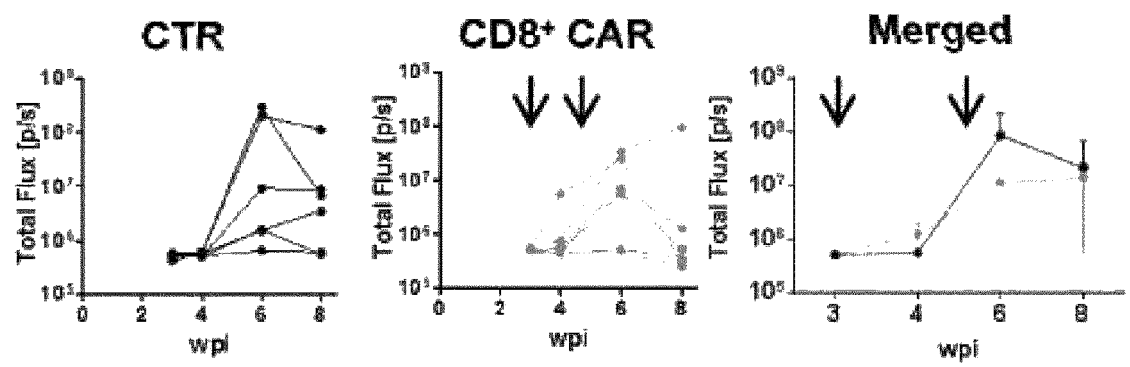

Fig. 10 (cont.)
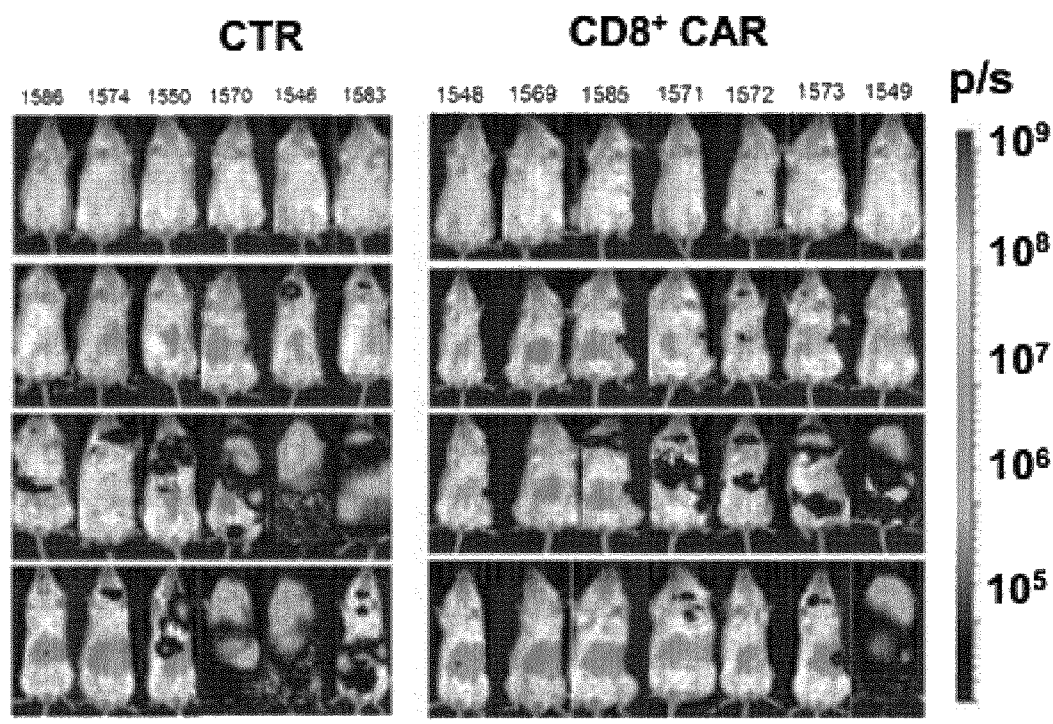
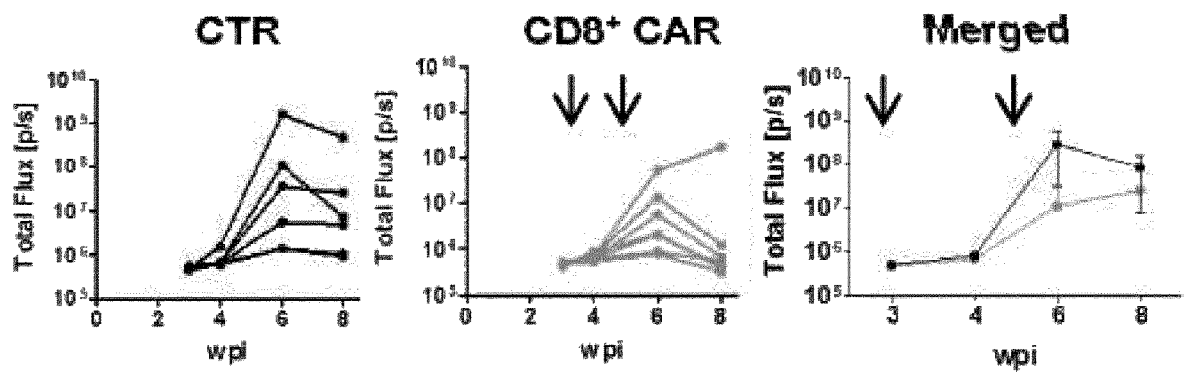

Fig. 10 (cont.)
E. EBV-PCR / Spleen
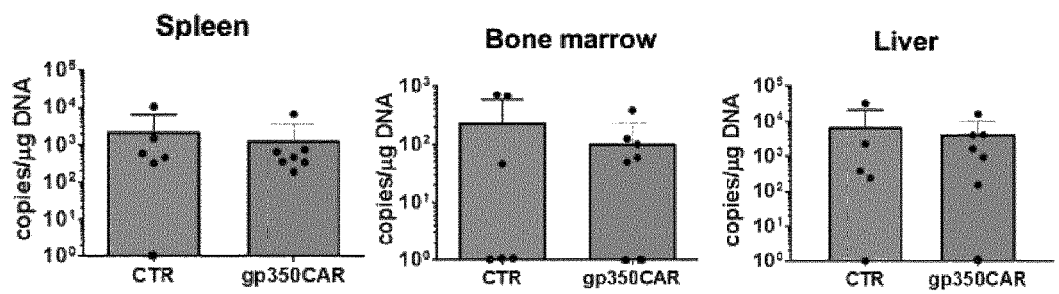
F. Flux and PCR correlation analyses
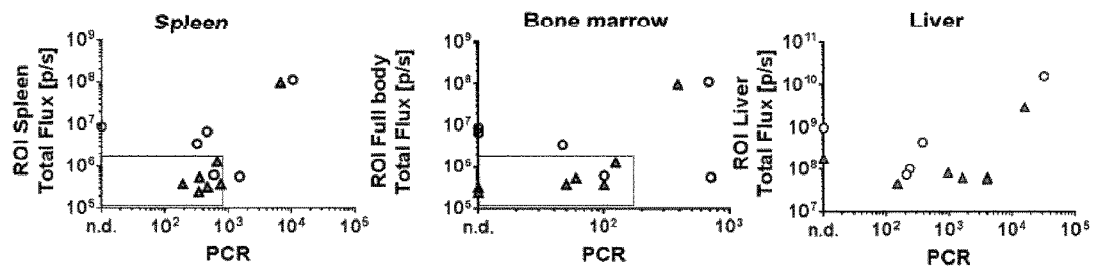
G. Optical Imaging of isolated tissues
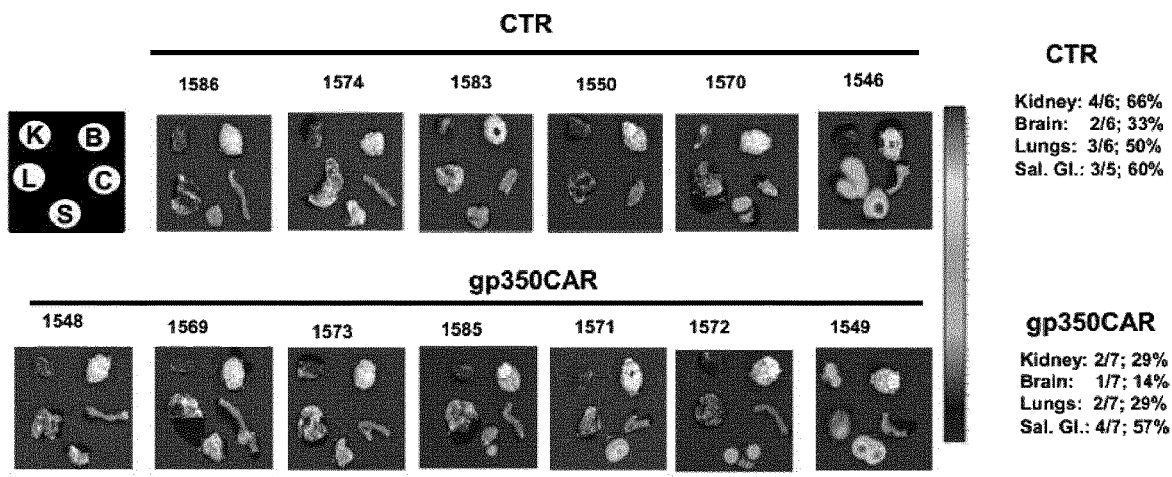

SEQUENCE LISTING

```
<160> NUMBER OF SEQ ID NOS: 37

<210> SEQ ID NO 1
<211> LENGTH: 7
<212> TYPE: PRT
<213> ORGANISM: Artificial Sequence
<220> FEATURE:
<223> OTHER INFORMATION: antibody

<400> SEQUENCE: 1

Gly Leu Ser Leu Thr Ser Asn
1               5

<210> SEQ ID NO 2
<211> LENGTH: 5
<212> TYPE: PRT
<213> ORGANISM: Artificial Sequence
<220> FEATURE:
<223> OTHER INFORMATION: antibody component

<400> SEQUENCE: 2

Trp Ser Asn Gly Gly
```

-continued

```
1               5

<210> SEQ ID NO 3
<211> LENGTH: 11
<212> TYPE: PRT
<213> ORGANISM: Artificial Sequence
<220> FEATURE:
<223> OTHER INFORMATION: antibody component

<400> SEQUENCE: 3

Pro Arg Tyr Asn Ser Gly Tyr Phe Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: antibody component

<400> SEQUENCE: 4

Lys Ala Ser Glu Ser Val Ser Thr Arg Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: antibody component

<400> SEQUENCE: 5

Lys Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: antibody component

<400> SEQUENCE: 6

Gln Gln Ser Trp Asn Gly Pro Leu Thr
1               5

<210> SEQ ID NO 7
<211> LENGTH: 7
<212> TYPE: PRT
<213> ORGANISM: Artificial Sequence
<220> FEATURE:
<223> OTHER INFORMATION: antibody component

<400> SEQUENCE: 7

Gly Phe Ser Leu Thr Ser Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: antibody component

<400> SEQUENCE: 8

Trp Ser Asp Gly Asp
1               5
```

```
<210> SEQ ID NO 9
<211> LENGTH: 29
<212> TYPE: PRT
<213> ORGANISM: Artificial Sequence
<220> FEATURE:
<223> OTHER INFORMATION: antibody component

<400> SEQUENCE: 9

Leu Gln Ser Glu Asp Thr Ala Thr Tyr Tyr Cys Ala Arg Leu Gln Val
 1               5                  10                  15

Phe Gly Tyr Pro Gly Ile Arg Asp Tyr Val Met Asp Ala
            20                  25

<210> SEQ ID NO 10
<211> LENGTH: 17
<212> TYPE: PRT
<213> ORGANISM: Artificial Sequence
<220> FEATURE:
<223> OTHER INFORMATION: antibody component

<400> SEQUENCE: 10

Lys Ser Ser Gln Ser Leu Leu Ser Ser Arg His Gln Lys Asn Phe Leu
 1               5                  10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: antibody component

<400> SEQUENCE: 11

His Ala Ser Thr Arg Gln Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: antibody component

<400> SEQUENCE: 12

Leu Gln His Tyr Thr Ser Pro Tyr Thr
 1               5

<210> SEQ ID NO 13
<211> LENGTH: 124
<212> TYPE: PRT
<213> ORGANISM: Artificial Sequence
<220> FEATURE:
<223> OTHER INFORMATION: antibody component
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
```

-continued

```
<222> LOCATION: (37)..(37)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (98)..(102)
<223> OTHER INFORMATION: Xaa can be any naturally occurring amino acid
<220> FEATURE:
<221> NAME/KEY: misc_feature
<222> LOCATION: (104)..(108)
<223> OTHER INFORMATION: Xaa can be any naturally occurring amino acid
<220> FEATURE:
<221> NAME/KEY: misc_feature
<222> LOCATION: (110)..(111)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (118)..(119)
<223> OTHER INFORMATION: Xaa can be any naturally occurring amino acid

<400> SEQUENCE: 13

Gln Val Gln Leu Lys Glu Ser Gly Pro Gly Leu Val Gln Pro Ser Gln
1               5                   10                  15
```

```
Thr Leu Ser Leu Thr Cys Thr Val Ser Gly Xaa Ser Leu Thr Ser Xaa
             20                  25                  30

Xaa Val Xaa Trp Xaa Arg Gln Pro Pro Gly Lys Gly Leu Glu Trp Xaa
         35                  40                  45

Gly Val Xaa Trp Ser Xaa Gly Xaa Thr Xaa Tyr Asn Ser Ala Xaa Lys
     50                  55                  60

Ser Arg Leu Ser Xaa Ser Arg Asp Thr Ser Lys Ser Gln Val Xaa Leu
 65                  70                  75                  80

Xaa Met Xaa Ser Leu Gln Xaa Glu Asp Thr Ala Xaa Tyr Xaa Cys Ala
             85                  90                  95

Arg Xaa Xaa Xaa Xaa Xaa Tyr Xaa Xaa Xaa Xaa Tyr Xaa Xaa Asp
             100                 105                 110

Xaa Trp Gly Gln Gly Xaa Xaa Val Thr Val Ser Ser
             115                 120
```

<210> SEQ ID NO 14
<211> LENGTH: 114
<212> TYPE: PRT
<213> ORGANISM: Artificial Sequence
<220> FEATURE:
<223> OTHER INFORMATION: antibody component
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: misc_feature
<222> LOCATION: (35)..(40)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature

```
<222> LOCATION: (59)..(61)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(100)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid

<400> SEQUENCE: 14

Asp Xaa Val Xaa Thr Gln Ser Pro Xaa Xaa Leu Ala Val Ser Xaa Gly
1               5                   10                  15

Glu Xaa Val Thr Ile Xaa Cys Lys Xaa Ser Xaa Ser Xaa Xaa Xaa Xaa
            20                  25                  30

Xaa His Xaa Xaa Xaa Xaa Xaa Xaa Trp Tyr Arg Gln Lys Pro Gly Gln
        35                  40                  45

Xaa Pro Lys Leu Leu Ile Tyr Xaa Xaa Ser Xaa Xaa Xaa Ser Gly Val
    50                  55                  60

Pro Xaa Arg Phe Xaa Gly Ser Gly Ser Gly Thr Asp Phe Thr Leu Thr
65                  70                  75                  80

Ile Xaa Xaa Val Xaa Ala Xaa Asp Xaa Ala Xaa Tyr Xaa Cys Xaa Gln
            85                  90                  95

Xaa Xaa Xaa Xaa Pro Xaa Thr Phe Gly Xaa Gly Thr Lys Leu Glu Xaa
            100                 105                 110

Lys Arg
```

<210> SEQ ID NO 15
<211> LENGTH: 119
<212> TYPE: PRT
<213> ORGANISM: Artificial Sequence
<220> FEATURE:
<223> OTHER INFORMATION: antibody component

<400> SEQUENCE: 15

Gln Val Gln Leu Lys Glu Ser Gly Pro Gly Leu Val Gln Pro Ser Gln
1               5                   10                  15

Thr Leu Ser Leu Thr Cys Thr Val Ser Gly Leu Ser Leu Thr Ser Asn
            20                  25                  30

Gly Val Ser Trp Ile Arg Gln Pro Pro Gly Lys Gly Leu Glu Trp Leu
        35                  40                  45

Gly Val Ile Trp Ser Asn Gly Thr Asp Tyr Asn Ser Ala Ile Lys
    50                  55                  60

Ser Arg Leu Ser Phe Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

Arg Pro Arg Tyr Asn Ser Gly Tyr Phe Phe Asp Tyr Trp Gly Gln Gly
            100                 105                 110

Val Met Val Thr Val Ser Ser
        115

<210> SEQ ID NO 16
<211> LENGTH: 107
<212> TYPE: PRT
<213> ORGANISM: Artificial Sequence
<220> FEATURE:
<223> OTHER INFORMATION: antibody component

<400> SEQUENCE: 16

Asp Thr Val Leu Thr Gln Ser Pro Ala Leu Ala Val Ser Pro Gly Glu
1               5                   10                  15

Arg Val Thr Ile Ser Cys Lys Ala Ser Glu Ser Val Ser Thr Arg Met
            20                  25                  30

His Trp Tyr Arg Gln Lys Pro Gly Gln Gln Pro Lys Leu Leu Ile Tyr
        35                  40                  45

Lys Thr Ser Asn Leu Ala Ser Gly Val Pro Ala Arg Phe Ser Gly Ser
    50                  55                  60

Gly Ser Gly Thr Asp Phe Thr Leu Thr Ile Asp Pro Val Glu Ala Asp
65                  70                  75                  80

Asp Thr Ala Thr Tyr Phe Cys Gln Gln Ser Trp Asn Gly Pro Leu Thr
                85                  90                  95

Phe Gly Ser Gly Thr Lys Leu Glu Ile Lys Arg
            100                 105

<210> SEQ ID NO 17
<211> LENGTH: 124
<212> TYPE: PRT
<213> ORGANISM: Artificial Sequence
<220> FEATURE:
<223> OTHER INFORMATION: antibody component

<400> SEQUENCE: 17

Gln Val Gln Leu Lys Glu Ser Gly Pro Gly Leu Val Gln Pro Ser Gln
1               5                   10                  15

```
Thr Leu Ser Leu Thr Cys Thr Val Ser Gly Phe Ser Leu Thr Ser Tyr
            20                  25                  30

His Val His Trp Val Arg Gln Pro Pro Gly Lys Gly Leu Glu Trp Met
        35                  40                  45

Gly Val Met Trp Ser Asp Gly Asp Thr Leu Tyr Asn Ser Ala Leu Lys
    50                  55                  60

Ser Arg Leu Ser Ile Ser Arg Asp Thr Ser Lys Ser Gln Val Leu Leu
65                  70                  75                  80

Gln Met Asp Ser Leu Gln Ser Glu Asp Thr Ala Thr Tyr Tyr Cys Ala
                85                  90                  95

Arg Leu Gln Val Phe Gly Tyr Pro Gly Ile Arg Asp Tyr Val Met Asp
            100                 105                 110

Ala Trp Gly Gln Gly Ala Ser Val Thr Val Ser Ser
        115                 120
```

<210> SEQ ID NO 18
<211> LENGTH: 114
<212> TYPE: PRT
<213> ORGANISM: Artificial Sequence
<220> FEATURE:
<223> OTHER INFORMATION: antibody component

<400> SEQUENCE: 18

```
Asp Leu Val Met Thr Gln Ser Pro Phe Ser Leu Ala Val Ser Glu Gly
1               5                   10                  15

Glu Met Val Thr Ile Lys Cys Lys Ser Ser Gln Ser Leu Leu Ser Ser
            20                  25                  30

Arg His Gln Lys Asn Phe Leu Ala Trp Tyr Arg Gln Lys Pro Gly Gln
        35                  40                  45

Ser Pro Lys Leu Leu Ile Tyr His Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Asp Val Gln Ala Glu Asp Leu Ala Asp Tyr Tyr Cys Leu Gln
                85                  90                  95

His Tyr Thr Ser Pro Tyr Thr Phe Gly Ala Gly Thr Lys Leu Glu Leu
            100                 105                 110

Lys Arg
```

<210> SEQ ID NO 19
<211> LENGTH: 19
<212> TYPE: PRT
<213> ORGANISM: Artificial Sequence
<220> FEATURE:
<223> OTHER INFORMATION: chimeric antigen receptor component

<400> SEQUENCE: 19

```
Met Glu Phe Gly Leu Ser Trp Leu Phe Leu Val Ala Ile Leu Lys Gly
1               5                   10                  15

Val Gln Cys
```

<210> SEQ ID NO 20
<211> LENGTH: 16
<212> TYPE: PRT
<213> ORGANISM: Artificial Sequence
<220> FEATURE:
<223> OTHER INFORMATION: chimeric antigen receptor component

<400> SEQUENCE: 20

```
Ser Gly Gly Gly Gly Ser Gly Gly Gly Gly Ser Gly Gly Gly Gly Ser
1               5                   10                  15
```

<210> SEQ ID NO 21
<211> LENGTH: 238
<212> TYPE: PRT
<213> ORGANISM: Artificial Sequence
<220> FEATURE:
<223> OTHER INFORMATION: chimeric antigen receptor component

<400> SEQUENCE: 21

```
Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Arg Asp Glu Leu Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Lys Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
            100                 105                 110

Leu Ser Leu Ser Pro Gly Lys Glu Ser Lys Tyr Gly Pro Pro Cys Pro
        115                 120                 125

Pro Cys Pro Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

<210> SEQ ID NO 22
<211> LENGTH: 232
<212> TYPE: PRT
<213> ORGANISM: Artificial Sequence
<220> FEATURE:
<223> OTHER INFORMATION: chimeric antigen receptor component

<400> SEQUENCE: 22

```
Glu Pro Lys Ser Pro Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60
```

```
Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
             85                   90                   95

Asp Trp Leu Asn Gly Lys Glu Tyr Lys Cys Lys Val Ser Asn Lys Ala
             100                 105                 110

Leu Pro Ala Pro Ile Glu Lys Thr Ile Ser Lys Ala Lys Gly Gln Pro
         115                 120                 125

Arg Glu Pro Gln Val Tyr Thr Leu Pro Pro Ser Arg Asp Glu Leu Thr
     130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
             165                 170                 175

Lys Thr Thr Pro Pro Val Leu Asp Ser Asp Gly Ser Phe Phe Leu Tyr
             180                 185                 190

Ser Lys Leu Thr Val Asp Lys Ser Arg Trp Gln Gln Gly Asn Val Phe
         195                 200                 205

Ser Cys Ser Val Met His Glu Ala Leu His Asn His Tyr Thr Gln Lys
     210                 215                 220

Ser Leu Ser Leu Ser Pro Gly Lys
225                 230
```

<210> SEQ ID NO 23
<211> LENGTH: 29
<212> TYPE: PRT
<213> ORGANISM: Artificial Sequence
<220> FEATURE:
<223> OTHER INFORMATION: chimeric antigen receptor component

<400> SEQUENCE: 23

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser
            20                  25
```

<210> SEQ ID NO 24
<211> LENGTH: 29
<212> TYPE: PRT
<213> ORGANISM: Artificial Sequence
<220> FEATURE:
<223> OTHER INFORMATION: chimeric antigen receptor component

<400> SEQUENCE: 24

```
Val Ile Ser Thr Ser Gly Arg Pro Trp Pro Gly Leu Val Gly Ser Phe
1               5                   10                  15

Ser Cys His Trp Leu Ser Pro Phe Thr Ala Thr Thr Gly
            20                  25
```

<210> SEQ ID NO 25
<211> LENGTH: 39
<212> TYPE: PRT
<213> ORGANISM: Artificial Sequence
<220> FEATURE:
<223> OTHER INFORMATION: chimeric antigen receptor component

<400> SEQUENCE: 25

```
Lys Arg Ser Arg Leu Leu His Ser Asp Tyr Met Asn Met Thr Pro Arg
1               5                   10                  15
```

```
Arg Pro Gly Pro Thr Arg Lys His Tyr Gln Pro Tyr Ala Pro Pro Arg
            20                  25                  30

Asp Phe Ala Ala Tyr Arg Ser
            35
```

<210> SEQ ID NO 26
<211> LENGTH: 42
<212> TYPE: PRT
<213> ORGANISM: Artificial Sequence
<220> FEATURE:
<223> OTHER INFORMATION: chimeric antigen receptor component

<400> SEQUENCE: 26

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

<210> SEQ ID NO 27
<211> LENGTH: 111
<212> TYPE: PRT
<213> ORGANISM: Artificial Sequence
<220> FEATURE:
<223> OTHER INFORMATION: chimeric antigen receptor component

<400> SEQUENCE: 27

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Pro Thr Thr Pro Phe Thr Cys Arg Pro Cys Pro Leu
            100                 105                 110
```

<210> SEQ ID NO 28
<211> LENGTH: 4
<212> TYPE: PRT
<213> ORGANISM: Artificial Sequence
<220> FEATURE:
<223> OTHER INFORMATION: chimeric antigen receptor component

<400> SEQUENCE: 28

```
Gly Asp Pro Ala
1
```

<210> SEQ ID NO 29
<211> LENGTH: 4
<212> TYPE: PRT
<213> ORGANISM: Artificial Sequence
<220> FEATURE:
<223> OTHER INFORMATION: chimeric antigen receptor component

<400> SEQUENCE: 29

Lys Asp Pro Lys
1

<210> SEQ ID NO 30
<211> LENGTH: 567
<212> TYPE: PRT
<213> ORGANISM: Artificial Sequence
<220> FEATURE:
<223> OTHER INFORMATION: chimeric antigen receptor component

<400> SEQUENCE: 30

```
Met Glu Phe Gly Leu Ser Trp Leu Phe Leu Val Ala Ile Leu Lys Gly
1               5                   10                  15

Val Gln Cys Gln Val Gln Leu Lys Glu Ser Gly Pro Gly Leu Val Gln
            20                  25                  30

Pro Ser Gln Thr Leu Ser Leu Thr Cys Thr Val Ser Gly Leu Ser Leu
        35                  40                  45

Thr Ser Asn Gly Val Ser Trp Ile Arg Gln Pro Pro Gly Lys Gly Leu
    50                  55                  60

Glu Trp Leu Gly Val Ile Trp Ser Asn Gly Thr Asp Tyr Asn Ser
65                  70                  75                  80

Ala Ile Lys Ser Arg Leu Ser Phe Ser Arg Asp Thr Ser Lys Ser Gln
                85                  90                  95

Val Phe Leu Lys Met Asn Ser Leu Gln Thr Glu Asp Thr Ala Met Tyr
            100                 105                 110

Phe Cys Ala Arg Pro Arg Tyr Asn Ser Gly Tyr Phe Asp Tyr Trp
        115                 120                 125

Gly Gln Gly Val Met Val Thr Val Ser Ser Gly Gly Gly Gly Ser
    130                 135                 140

Gly Gly Gly Gly Ser Gly Gly Gly Ser Asp Thr Val Leu Thr Gln
145                 150                 155                 160

Ser Pro Ala Leu Ala Val Ser Pro Gly Glu Arg Val Thr Ile Ser Cys
                165                 170                 175

Lys Ala Ser Glu Ser Val Ser Thr Arg Met His Trp Tyr Arg Gln Lys
            180                 185                 190

Pro Gly Gln Gln Pro Lys Leu Leu Ile Tyr Lys Thr Ser Asn Leu Ala
        195                 200                 205

Ser Gly Val Pro Ala Arg Phe Ser Gly Ser Gly Ser Gly Thr Asp Phe
    210                 215                 220

Thr Leu Thr Ile Asp Pro Val Glu Ala Asp Asp Thr Ala Thr Tyr Phe
225                 230                 235                 240

Cys Gln Gln Ser Trp Asn Gly Pro Leu Thr Phe Gly Ser Gly Thr Lys
                245                 250                 255

Leu Glu Ile Lys Gly Asp Pro Ala Glu Ser Lys Tyr Gly Pro Pro Cys
            260                 265                 270

Pro Pro Cys Pro Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350
```

-continued

```
Trp Gln Gln Gly Asn Val Phe Ser Cys Ser Val Met His Glu Ala Leu
            355                 360                 365
His Asn His Tyr Thr Gln Lys Ser Leu Ser Leu Ser Pro Gly Lys Lys
    370                 375                 380
Asp Pro Lys Phe Trp Val Leu Val Val Gly Gly Val Leu Ala Cys
385                 390                 395                 400
Tyr Ser Leu Leu Val Thr Val Ala Phe Ile Ile Phe Trp Val Arg Ser
                405                 410                 415
Lys Arg Ser Arg Leu Leu His Ser Asp Tyr Met Asn Met Thr Pro Arg
            420                 425                 430
Arg Pro Gly Pro Thr Arg Lys His Tyr Gln Pro Tyr Ala Pro Pro Arg
            435                 440                 445
Asp Phe Ala Ala Tyr Arg Ser Arg Val Lys Phe Ser Arg Ser Ala Asp
    450                 455                 460
Ala Pro Ala Tyr Gln Gln Gly Gln Asn Gln Leu Tyr Asn Glu Leu Asn
465                 470                 475                 480
Leu Gly Arg Arg Glu Glu Tyr Asp Val Leu Asp Lys Arg Arg Gly Arg
                485                 490                 495
Asp Pro Glu Met Gly Gly Lys Pro Arg Arg Lys Asn Pro Gln Glu Gly
            500                 505                 510
Leu Tyr Asn Glu Leu Gln Lys Asp Lys Met Ala Glu Ala Tyr Ser Glu
            515                 520                 525
Ile Gly Met Lys Gly Glu Arg Arg Arg Gly Lys Gly His Asp Gly Leu
            530                 535                 540
Tyr Gln Gly Leu Ser Thr Ala Thr Lys Asp Thr Tyr Asp Ala Leu His
545                 550                 555                 560
Met Gln Ala Leu Pro Pro Arg
                565

<210> SEQ ID NO 31
<211> LENGTH: 578
<212> TYPE: PRT
<213> ORGANISM: Artificial Sequence
<220> FEATURE:
<223> OTHER INFORMATION: chimeric antigen receptor component

<400> SEQUENCE: 31

Met Glu Phe Gly Leu Ser Trp Leu Phe Leu Val Ala Ile Leu Lys Gly
1               5                   10                  15
Val Gln Cys Gln Val Gln Leu Lys Glu Ser Gly Pro Gly Leu Val Gln
            20                  25                  30
Pro Ser Gln Thr Leu Ser Leu Thr Cys Thr Val Ser Gly Phe Ser Leu
        35                  40                  45
Thr Ser Tyr His Val His Trp Val Arg Gln Pro Pro Gly Lys Gly Leu
    50                  55                  60
Glu Trp Met Gly Val Met Trp Ser Asp Gly Asp Thr Leu Tyr Asn Ser
65                  70                  75                  80
Ala Leu Lys Ser Arg Leu Ser Ile Ser Arg Asp Thr Ser Lys Ser Gln
                85                  90                  95
Val Leu Leu Gln Met Asp Ser Leu Gln Ser Glu Asp Thr Ala Thr Tyr
            100                 105                 110
Tyr Cys Ala Arg Leu Gln Val Phe Gly Tyr Pro Gly Ile Arg Asp Tyr
            115                 120                 125
Val Met Asp Ala Trp Gly Gln Gly Ala Ser Val Thr Val Ser Ser Ser
        130                 135                 140
```

-continued

Gly Gly Gly Gly Ser Gly Gly Gly Ser Gly Gly Gly Ser Asp
145                 150                 155                 160

Leu Val Met Thr Gln Ser Pro Phe Ser Leu Ala Val Ser Glu Gly Glu
            165                 170                 175

Met Val Thr Ile Lys Cys Lys Ser Ser Gln Ser Leu Leu Ser Ser Arg
            180                 185                 190

His Gln Lys Asn Phe Leu Ala Trp Tyr Arg Gln Lys Pro Gly Gln Ser
            195                 200                 205

Pro Lys Leu Leu Ile Tyr His Ala Ser Thr Arg Gln Ser Gly Val Pro
210                 215                 220

Asp Arg Phe Ile Gly Ser Gly Ser Gly Thr Asp Phe Thr Leu Thr Ile
225                 230                 235                 240

Ser Asp Val Gln Ala Glu Asp Leu Ala Asp Tyr Tyr Cys Leu Gln His
            245                 250                 255

Tyr Thr Ser Pro Tyr Thr Phe Gly Ala Gly Thr Lys Leu Glu Leu Lys
            260                 265                 270

Gly Asp Pro Ala Glu Ser Lys Tyr Gly Pro Pro Cys Pro Pro Cys Pro
            275                 280                 285

Gly Gln Pro Arg Glu Pro Gln Val Tyr Thr Leu Pro Pro Ser Arg Asp
290                 295                 300

Glu Leu Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
            325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
            355                 360                 365

Asn Val Phe Ser Cys Ser Val Met His Glu Ala Leu His Asn His Tyr
            370                 375                 380

Thr Gln Lys Ser Leu Ser Leu Ser Pro Gly Lys Lys Asp Pro Lys Phe
385                 390                 395                 400

Trp Val Leu Val Val Val Gly Gly Val Leu Ala Cys Tyr Ser Leu Leu
            405                 410                 415

Val Thr Val Ala Phe Ile Ile Phe Trp Val Arg Ser Lys Arg Ser Arg
            420                 425                 430

Leu Leu His Ser Asp Tyr Met Asn Met Thr Pro Arg Arg Pro Gly Pro
            435                 440                 445

Thr Arg Lys His Tyr Gln Pro Tyr Ala Pro Pro Arg Asp Phe Ala Ala
            450                 455                 460

Tyr Arg Ser Arg Val Lys Phe Ser Arg Ser Ala Asp Ala Pro Ala Tyr
465                 470                 475                 480

Gln Gln Gly Gln Asn Gln Leu Tyr Asn Glu Leu Asn Leu Gly Arg Arg
            485                 490                 495

Glu Glu Tyr Asp Val Leu Asp Lys Arg Gly Arg Asp Pro Glu Met
            500                 505                 510

Gly Gly Lys Pro Arg Arg Lys Asn Pro Gln Glu Gly Leu Tyr Asn Glu
            515                 520                 525

Leu Gln Lys Asp Lys Met Ala Glu Ala Tyr Ser Glu Ile Gly Met Lys
            530                 535                 540

Gly Glu Arg Arg Arg Gly Lys Gly His Asp Gly Leu Tyr Gln Gly Leu
545                 550                 555                 560

Ser Thr Ala Thr Lys Asp Pro Thr Thr Pro Phe Thr Cys Arg Pro Cys

-continued

```
                565                 570                 575

Pro Leu

<210> SEQ ID NO 32
<211> LENGTH: 685
<212> TYPE: PRT
<213> ORGANISM: Artificial Sequence
<220> FEATURE:
<223> OTHER INFORMATION: chimeric antigen receptor component

<400> SEQUENCE: 32

Met Glu Phe Gly Leu Ser Trp Leu Phe Leu Val Ala Ile Leu Lys Gly
1               5                   10                  15

Val Gln Cys Gln Val Gln Leu Lys Glu Ser Gly Pro Gly Leu Val Gln
            20                  25                  30

Pro Ser Gln Thr Leu Ser Leu Thr Cys Thr Val Ser Gly Leu Ser Leu
        35                  40                  45

Thr Ser Asn Gly Val Ser Trp Ile Arg Gln Pro Pro Gly Lys Gly Leu
    50                  55                  60

Glu Trp Leu Gly Val Ile Trp Ser Asn Gly Gly Thr Asp Tyr Asn Ser
65                  70                  75                  80

Ala Ile Lys Ser Arg Leu Ser Phe Ser Arg Asp Thr Ser Lys Ser Gln
                85                  90                  95

Val Phe Leu Lys Met Asn Ser Leu Gln Thr Glu Asp Thr Ala Met Tyr
            100                 105                 110

Phe Cys Ala Arg Pro Arg Tyr Asn Ser Gly Tyr Phe Phe Asp Tyr Trp
        115                 120                 125

Gly Gln Gly Val Met Val Thr Val Ser Ser Gly Gly Gly Gly Ser
    130                 135                 140

Gly Gly Gly Gly Ser Gly Gly Gly Ser Asp Thr Val Leu Thr Gln
145                 150                 155                 160

Ser Pro Ala Leu Ala Val Ser Pro Gly Glu Arg Val Thr Ile Ser Cys
                165                 170                 175

Lys Ala Ser Glu Ser Val Ser Thr Arg Met His Trp Tyr Arg Gln Lys
            180                 185                 190

Pro Gly Gln Gln Pro Lys Leu Leu Ile Tyr Lys Thr Ser Asn Leu Ala
        195                 200                 205

Ser Gly Val Pro Ala Arg Phe Ser Gly Ser Gly Ser Gly Thr Asp Phe
    210                 215                 220

Thr Leu Thr Ile Asp Pro Val Glu Ala Asp Asp Thr Ala Thr Tyr Phe
225                 230                 235                 240

Cys Gln Gln Ser Trp Asn Gly Pro Leu Thr Phe Gly Ser Gly Thr Lys
                245                 250                 255

Leu Glu Ile Lys Gly Asp Pro Ala Glu Pro Lys Ser Pro Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350
```

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Lys Asp Pro Lys Phe Trp Val Leu Val Val Val Gly Gly Val Leu Ala
            500                 505                 510

Gly Leu Val Gly Ser Phe Ser Cys His Trp Leu Ser Pro Phe Thr Ala
        515                 520                 525

Thr Thr Gly Lys Arg Gly Arg Lys Lys Leu Leu Tyr Ile Phe Lys Gln
    530                 535                 540

Pro Phe Met Arg Pro Val Gln Thr Thr Gln Glu Glu Asp Gly Cys Ser
545                 550                 555                 560

Cys Arg Phe Pro Glu Glu Glu Glu Gly Gly Cys Glu Leu Arg Val Lys
                565                 570                 575

Phe Ser Arg Ser Ala Asp Ala Pro Ala Tyr Gln Gln Gly Gln Asn Gln
            580                 585                 590

Leu Tyr Asn Glu Leu Asn Leu Gly Arg Arg Glu Glu Tyr Asp Val Leu
        595                 600                 605

Asp Lys Arg Arg Gly Arg Asp Pro Glu Met Gly Gly Lys Pro Arg Arg
    610                 615                 620

Lys Asn Pro Gln Glu Gly Leu Tyr Asn Glu Leu Gln Lys Asp Lys Met
625                 630                 635                 640

Ala Glu Ala Tyr Ser Glu Ile Gly Met Lys Gly Glu Arg Arg Arg Gly
                645                 650                 655

Lys Gly His Asp Gly Leu Tyr Gln Gly Leu Ser Thr Ala Thr Lys Asp
            660                 665                 670

Thr Tyr Asp Ala Leu His Met Gln Ala Leu Pro Pro Arg
        675                 680                 685

<210> SEQ ID NO 33
<211> LENGTH: 674
<212> TYPE: PRT
<213> ORGANISM: Artificial Sequence
<220> FEATURE:
<223> OTHER INFORMATION: chimeric antigen receptor component

<400> SEQUENCE: 33

Met Glu Phe Gly Leu Ser Trp Leu Phe Leu Val Ala Ile Leu Lys Gly
1               5                   10                  15

Val Gln Cys Gln Val Gln Leu Lys Glu Ser Gly Pro Gly Leu Val Gln
            20                  25                  30

```
Pro Ser Gln Thr Leu Ser Leu Thr Cys Thr Val Ser Gly Phe Ser Leu
        35                  40                  45

Thr Ser Tyr His Val His Trp Val Arg Gln Pro Pro Gly Lys Gly Leu
    50                  55                  60

Glu Trp Met Gly Val Met Trp Ser Asp Gly Asp Thr Leu Tyr Asn Ser
65                  70                  75                  80

Ala Leu Lys Ser Arg Leu Ser Ile Ser Arg Asp Thr Ser Lys Ser Gln
                85                  90                  95

Val Leu Leu Gln Met Asp Ser Leu Gln Ser Glu Asp Thr Ala Thr Tyr
            100                 105                 110

Tyr Cys Ala Arg Leu Gln Val Phe Gly Tyr Pro Gly Ile Arg Asp Tyr
            115                 120                 125

Val Met Asp Ala Trp Gly Gln Gly Ala Ser Val Thr Val Ser Ser Ser
        130                 135                 140

Gly Gly Gly Gly Ser Gly Gly Gly Ser Gly Gly Gly Gly Ser Asp
145                 150                 155                 160

Leu Val Met Thr Gln Ser Pro Phe Ser Leu Ala Val Ser Glu Gly Glu
                165                 170                 175

Met Val Thr Ile Lys Cys Lys Ser Ser Gln Ser Leu Leu Ser Ser Arg
            180                 185                 190

His Gln Lys Asn Phe Leu Ala Trp Tyr Arg Gln Lys Pro Gly Gln Ser
        195                 200                 205

Pro Lys Leu Leu Ile Tyr His Ala Ser Thr Arg Gln Ser Gly Val Pro
    210                 215                 220

Asp Arg Phe Ile Gly Ser Gly Ser Gly Thr Asp Phe Thr Leu Thr Ile
225                 230                 235                 240

Ser Asp Val Gln Ala Glu Asp Leu Ala Asp Tyr Tyr Cys Leu Gln His
                245                 250                 255

Tyr Thr Ser Pro Tyr Thr Phe Gly Ala Gly Thr Lys Leu Glu Leu Lys
            260                 265                 270

Gly Asp Pro Ala Glu Pro Lys Ser Pro Asp Lys Thr His Thr Cys Pro
        275                 280                 285

Pro Cys Pro Ala Pro Glu Leu Leu Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

Arg Glu Glu Gln Tyr Asn Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Asp Glu Leu Thr Lys Asn Gln Val Ser Leu Thr Cys Leu Val Lys Gly
            420                 425                 430

Phe Tyr Pro Ser Asp Ile Ala Val Glu Trp Glu Ser Asn Gly Gln Pro
        435                 440                 445
```

```
Glu Asn Asn Tyr Lys Thr Thr Pro Pro Val Leu Asp Ser Asp Gly Ser
            450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys Lys Asp Pro Lys
            500                 505                 510

Phe Trp Val Ile Ser Thr Ser Gly Arg Pro Trp Pro Gly Leu Val Gly
            515                 520                 525

Ser Phe Ser Cys His Trp Leu Ser Pro Phe Thr Ala Thr Thr Gly Lys
530                 535                 540

Arg Gly Arg Lys Lys Leu Leu Tyr Ile Phe Lys Gln Pro Phe Met Arg
545                 550                 555                 560

Pro Val Gln Thr Thr Gln Glu Glu Asp Gly Cys Ser Cys Arg Phe Pro
                565                 570                 575

Glu Glu Glu Glu Gly Gly Cys Glu Arg Val Lys Phe Ser Arg Ser Ala
                580                 585                 590

Asp Ala Pro Ala Tyr Gln Gln Gly Gln Asn Gln Leu Tyr Asn Glu Leu
            595                 600                 605

Asn Leu Gly Arg Arg Glu Glu Tyr Asp Val Leu Asp Lys Arg Gly
            610                 615                 620

Arg Asp Pro Glu Met Gly Gly Lys Pro Arg Arg Lys Asn Pro Gln Glu
625                 630                 635                 640

Gly Leu Tyr Asn Glu Leu Gln Lys Asp Lys Met Ala Glu Ala Tyr Ser
                645                 650                 655

Glu Ile Gly Met Lys Gly Glu Arg Arg Arg Gly Lys Gly His Asp Gly
            660                 665                 670

Leu Tyr
```

<210> SEQ ID NO 34
<211> LENGTH: 1701
<212> TYPE: DNA
<213> ORGANISM: Artificial Sequence
<220> FEATURE:
<223> OTHER INFORMATION: chimeric antigen receptor component

<400> SEQUENCE: 34

```
atggagtttg gcctgagctg ctgtttctg gtggccattc tgaagggcgt gcagtgccag      60
gtgcagctga agaatctgg acctggcctg gtgcagccta gccagacact gtctctgaca     120
tgtacagtgt ccggcctgag cctgacaagc aacggcgtta gctggatcag acagcctcct    180
ggcaaaggcc tggaatggct gggcgttatc tggtccaatg cggcaccga ctacaacagc     240
gccatcaaga gcagactgag cttcagcaga gacaccagca gagccaggt gttcctgaag    300
atgaacagcc tgcagaccga ggacaccgcc atgtactttt gcgccagacc tcggtacaac    360
tccggctact tcttcgatta ttggggccag ggcgtgatgg tcacagtgtc atctagcgga    420
ggcggaggaa gtggtggcgg aggttctggc ggcggaggat ctgatacagt gctgacacaa    480
agccccgctc tggctgtgtc tcctggcgag agagtgacaa tcagctgcaa ggccagcgag    540
agcgtgtcca ccagaatgca ctggtacaga cagaagcccg ccagcagcc aaagctgctg    600
atctacaaga ccagcaatct ggccagcggc gtgccagcca gatttttctgg ttctggctct    660
ggcaccgatt tcaccctgac catcgatccc gtggaagccg acgataccgc cacctacttt    720
tgtcagcaga gctggaacgg ccctctgacc tttggcagcg gcaccaagct ggaaatcaaa    780
```

```
ggggatcccg ccgagtctaa atatggccca ccttgcccac cgtgcccagg gcagcccga      840 gaaccacagg tgtacaccct gcccccatcc cgggatgagc tgaccaagaa ccaggtcagc      900
ctgacctgcc tggtcaaagg cttctatccc agcgacatcg ccgtggagtg ggagagcaat      960
gggcaaccgg agaacaacta caagaccacg cctcccgtgc tggactccga cggctccttc     1020
ttcctctaca gcaagctcac cgtggacaag agcaggtggc agcaggggaa cgtcttctca     1080
tgctccgtga tgcatgaggc tctgcacaac cactacacgc agaagagcct ctccctgtct     1140
ccgggtaaaa aagatcccaa attttgggtg ctggtggtgg ttggtggagt cctggcttgc     1200
tatagcttgc tagtaacagt ggcctttatt attttctggg tgaggagtaa gaggagcagg     1260
ctcctgcaca gtgactacat gaacatgact ccccgccgcc ccgggcccac ccgcaagcat     1320
taccagccct atgccccacc acgcgacttc gcagcctatc gctccagagt gaagttcagc     1380
aggagcgcag acgccccgc gtaccagcag gccagaacc agctctataa cgagctcaat     1440
ctaggacgaa gagaggagta cgatgttttg gacaagagac gtggccggga ccctgagatg     1500
gggggaaagc cgagaaggaa gaaccctcag gaaggcctgt acaatgaact gcagaaagat     1560
aagatggcgg aggcctacag tgagattggg atgaaaggcg agcgccggag gggcaagggg     1620
cacgatggcc tttaccaggg tctcagtaca gccaccaagg acacctacga cgcccttcac     1680
atgcaggccc tgccccctcg c                                                1701

<210> SEQ ID NO 35
<211> LENGTH: 1737
<212> TYPE: DNA
<213> ORGANISM: Artificial Sequence
<220> FEATURE:
<223> OTHER INFORMATION: chimeric antigen receptor component

<400> SEQUENCE: 35
atggagtttg gcctgagctg gctgtttctg gtggccattc tgaagggcgt gcagtgccag       60
gtgcagctga agaatctgg acctggcctg gtgcagccta gccagacact gtctctgaca      120
tgcaccgtgt ccggcttcag cctgacaagc taccatgtgc actgggtccg acagccacct      180
ggcaaaggac tggaatggat gggcgttatg tggtccgacg gcgacacact gtacaacagc      240
gccctgaagt cccggctgag catcagcaga gataccagca agtctcaggt gctgctgcag      300
atggatagcc tgcagagcga ggataccgcc acctactatt gtgccagact ccaggtgttc      360
ggctaccccg gcatcagaga ttacgtgatg gatgcttggg gacagggcgc ctctgtgaca      420
gtttcttcta gcggaggcgg aggaagtggt ggcggaggtt ctggcggcgg aggatctgat      480
ctggttatga cacagagccc tttcagcctg gccgtgtctg agggcgagat ggtcacaatc      540
aagtgcaaga gcagccagag cctgctgagc agccggcacc agaaaaactt ctggcttgg      600 tacagacaga agcccggaca gagccccaag ctgctgatct accatgccag cacaagacag      660
agcggcgtgc ccgatagatt catcggatct ggcagcggca ccgacttcac actgacaatt      720
tctgatgtgc aggccgagga tctggccgac tactactgtc tgcagcacta caagccccc      780 tacaccttcg gagccggcac aaagctggaa ctgaaagggg atcccgccga gtctaaatat      840 ggcccaccttt gccaccgtg cccagggcag ccccgagaac cacaggtgta cacccctgccc      900 ccatcccggg atgagctgac caagaaccag gtcagcctga cctgctggt caaaggcttc      960 tatcccagcg acatcgccgt ggagtgggag agcaatgggc aaccgagaa caactacaag     1020 accacgcctc ccgtgctgga ctccgacggc tccttcttcc tctacagcaa gctcaccgtg     1080
```

```
gacaagagca ggtggcagca ggggaacgtc ttctcatgct ccgtgatgca tgaggctctg   1140
cacaaccact acacgcagaa gagcctctcc ctgtctccgg gtaaaaaaga tcccaaattt   1200
tgggtgctgg tggtggttgg tggagtcctg gcttgctata gcttgctagt aacagtggcc   1260
tttattattt tctgggtgag gagtaagagg agcaggctcc tgcacagtga ctacatgaac   1320
atgactcccc gccgccccgg gcccacccgc aagcattacc agccctatgc cccaccacgc   1380
gacttcgcag cctatcgctc cagagtgaag ttcagcagga gcgcagacgc cccgcgtac    1440 cagcagggcc agaaccagct ctataacgag ctcaatctag gacgaagaga ggagtacgat   1500
gttttggaca gagacgtgg ccgggaccct gagatggggg gaaagccgag aaggaagaac    1560
cctcaggaag gcctgtacaa tgaactgcag aaagataaga tggcggaggc ctacagtgag   1620
attgggatga aggcgagcg ccggaggggc aaggggcacg atggccttta ccagggtctc    1680
agtacagcca ccaaggacac ctacgacgcc cttcacatgc aggccctgcc ccctcgc      1737
```

<210> SEQ ID NO 36
<211> LENGTH: 2058
<212> TYPE: DNA
<213> ORGANISM: Artificial Sequence
<220> FEATURE:
<223> OTHER INFORMATION: chimeric antigen receptor component

<400> SEQUENCE: 36

```
atggagtttg gcctgagctg gctgtttctg gtggccattc tgaagggcgt gcagtgccag     60
gtgcagctga agaatctgg acctggcctg gtgcagccta ccagacact gtctctgaca     120 tgtacagtgt ccggcctgag cctgacaagc aacggcgtta gctggatcag acagcctcct   180
ggcaaaggcc tggaatggct gggcgttatc tggtccaatg gcggcaccga ctacaacagc   240
gccatcaaga gcagactgag cttcagcaga gacaccagca gagccaggt gttcctgaag    300 atgaacagcc tgcagaccga ggacaccgcc atgtacttt gcgccagacc tcggtacaac    360
tccggctact tcttcgatta ttggggccag ggcgtgatgg tcacagtgtc atctagcgga   420
ggcggaggaa gtggtggcgg aggttctggc ggcggaggat ctgatacagt gctgacacaa   480
agccccgctc tggctgtgtc tcctggcgag agagtgacaa tcagctgcaa ggccagcgag   540
agcgtgtcca ccagaatgca ctggtacaga cagaagcccg ccagcagcc aaagctgctg   600 atctacaaga ccagcaatct ggccagcggc gtgccagcca gatttctgg ttctggctct    660 ggcaccgatt tcaccctgac catcgatccc gtggaagccg acgataccgc cacctacttt   720
tgtcagcaga gctggaacgg ccctctgacc tttggcagcg gcaccaagct ggaaatcaaa   780
ggggatcccg ccgagcccaa atctcctgac aaaactcaca catgcccacc gtgcccagca   840
cctgaactcc tggggggacc gtcagtcttc ctcttccccc caaaacccaa ggacaccctc   900
atgatctccc ggacccctga ggtcacatgc gtggtggtgg acgtgagcca cgaagaccct   960
gaggtcaagt tcaactggta cgtggacggc gtggaggtgc ataatgccaa gacaaagccg   1020
cgggaggagc agtacaacag cacgtaccgt gtggtcagc tcctcaccgt cctgcaccag   1080
gactggctga atggcaagga gtacaagtgc aaggtctcca acaaagccct cccagccccc   1140
atcgagaaaa ccatctccaa agccaaaggg cagccccgag aaccacaggt gtacaccctg   1200
cccccatccc gggatgagct gaccaagaac caggtcagcc tgacctgcct ggtcaaaggc   1260
ttctatccca gcgacatcgc cgtggagtgg gagagcaatg ggcaaccgga gaacaactac   1320
aagaccacgc ctcccgtgct ggactccgac ggctccttct tcctctacag caagctcacc   1380
gtggacaaga gcaggtggca gcaggggaac gtcttctcat gctccgtgat gcatgaggct   1440
```

```
ctgcacaacc actacacgca gaagagcctc tccctgtctc cgggtaaaaa agatcccaaa      1500
ttttggtgtg atatctacat ctgggcgccc ttggccggga cttgtggggt ccttctcctg      1560
tcactggtta tcacccttta ctgcaaccac aggaacaaac ggggcagaaa gaaactcctg      1620
tatatattca acaaccatt tatgagacca gtacaaacta ctcaagagga gatggctgt       1680 agctgccgat ttccagaaga agaagaagga ggatgtgaac tgagagtgaa gttcagcagg      1740
agcgcagacg cccccgcgta ccagcagggc cagaaccagc tctataacga gctcaatcta      1800
ggacgaagag aggagtacga tgttttggac aagagacgtg gccgggaccc tgagatgggg      1860
ggaaagccga gaaggaagaa ccctcaggaa ggcctgtaca atgaactgca gaaagataag      1920
atggcggagg cctacagtga gattgggatg aaaggcgagc gccggagggg caaggggcac      1980
gatggccttt accagggtct cagtacagcc accaaggaca cctacgacgc ccttcacatg      2040
caggccctgc cccctcgc                                                     2058
```

<210> SEQ ID NO 37
<211> LENGTH: 2094
<212> TYPE: DNA
<213> ORGANISM: Artificial Sequence
<220> FEATURE:
<223> OTHER INFORMATION: chimeric antigen receptor component

<400> SEQUENCE: 37

```
atggagtttg gcctgagctg ctgtttctg gtggccattc tgaagggcgt gcagtgccag         60
gtgcagctga agaatctgg acctggcctg gtgcagccta gccagacact gtctctgaca        120
tgcaccgtgt ccggcttcag cctgacaagc taccatgtgc actgggtccg acagccacct       180
ggcaaaggac tggaatggat gggcgttatg tggtccgacg cgacacact gtacaacagc        240 gccctgaagt cccggctgag catcagcaga gataccagca gtctcaggt gctgctgcag       300 atggatagcc tgcagagcga ggataccgcc acctactatt gtgccagact ccaggtgttc       360
ggctaccccg gcatcagaga ttacgtgatg gatgcttggg gacagggcgc ctctgtgaca       420
gtttcttcta gcggaggcgg aggaagtggt ggcggaggtt ctggcggcgg aggatctgat       480
ctggttatga cacagagccc tttcagcctg gccgtgtctg agggcgagat ggtcacaatc       540
aagtgcaaga gcagccagag cctgctgagc agccggcacc agaaaaactt tctggcttgg       600
tacagacaga agcccggaca gagccccaag ctgctgatct accatgccag cacaagacag       660
agcggcgtgc ccgatagatt catcggatct ggcagcggca ccgacttcac actgacaatt       720
tctgatgtgc aggccgagga tctggccgac tactactgtc tgcagcacta caagcccc       780 tacaccttcg gagccggcac aaagctggaa ctgaagggg atcccgccga gcccaaatct       840
cctgacaaaa ctcacacatg cccaccgtgc ccagcacctg aactcctggg gggaccgtca       900
gtcttcctct tccccccaaa acccaaggac accctcatga tctcccggac ccctgaggtc       960
acatgcgtgt ggtggacgt gagccacgaa gaccctgagg tcaagttcaa ctggtacgtg      1020
gacggcgtgg aggtgcataa tgccaagaca aagccgcggg aggagcagta caacagcacg      1080
taccgtgtgg tcagcgtcct caccgtcctg caccaggact ggctgaatgg caaggagtac      1140
aagtgcaagg tctccaacaa agccctccca gcccccatcg agaaaaccat ctccaaagcc      1200
aaagggcagc cccgagaacc acaggtgtac accctgcccc catcccggga tgagctgacc      1260
aagaaccagg tcagcctgac ctgcctggtc aaaggcttct atcccagcga catcgccgtg      1320
gagtgggaga gcaatgggca accggagaac aactacaaga ccacgcctcc cgtgctggac      1380
```

```
tccgacggct ccttcttcct ctacagcaag ctcaccgtgg acaagagcag gtggcagcag    1440
gggaacgtct tctcatgctc cgtgatgcat gaggctctgc acaaccacta cacgcagaag    1500
agcctctccc tgtctccggg taaaaaagat cccaaatttt ggtgtgatat ctacatctgg    1560
gcgcccttgg ccgggacttg tggggtcctt ctcctgtcac tggttatcac cctttactgc    1620
aaccacagga acaaacgggg cagaaagaaa ctcctgtata tattcaaaca accatttatg    1680
agaccagtac aaactactca agaggaagat ggctgtagct gccgatttcc agaagaagaa    1740
gaaggaggat gtgaactgag agtgaagttc agcaggagcg cagacgcccc cgcgtaccag    1800
cagggccaga accagctcta taacgagctc aatctaggac gaagagagga gtacgatgtt    1860
ttggacaaga gacgtggccg ggaccctgag atgggggggaa agccgagaag gaagaaccct    1920
caggaaggcc tgtacaatga actgcagaaa gataagatgg cggaggccta cagtgagatt    1980
gggatgaaag gcgagcgccg gaggggcaag gggcacgatg gcctttacca gggtctcagt    2040
acagccacca aggacaccta cgacgccctt cacatgcagg ccctgccccc tcgc          2094
```

CHIMERIC ANTIGEN RECEPTOR AND CAR-T CELLS THAT BIND A HERPES VIRUS ANTIGEN

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 33718675_1.txt, the date of creation of the ASCII text file is Oct. 19, 2020, and the size of the ASCII text file is 53.6 KB.

The invention relates to an isolated chimeric antigen receptor (CAR) polypeptide, wherein the CAR comprises an extracellular antigen-binding domain, comprising an antibody or antibody fragment that binds to a protein encoded by a herpes virus, or to a protein complex comprising said protein (herpes virus antigen), wherein said herpes virus antigen is present on the surface of a human cell that is latently infected with said herpes virus and supports the lytic phase of viral replication. The invention further relates to a nucleic acid molecule encoding the CAR of the invention, a genetically modified immune cell, preferably a T cell, expressing the CAR of the invention and the use of said cell in the treatment of a medical disorder associated with human herpesvirus, such as herpes virus-associated cancers, chronic active herpes virus infections or primary herpes virus infections. In preferred embodiments the herpes virus is Epstein-Barr virus (EBV) and a preferred herpes virus antigen target of the CAR is the EBV glycoprotein 350/220 (gp350/gp220).

BACKGROUND OF THE INVENTION

Epstein-Barr virus (EBV) is a human herpesvirus associated with lymphoproliferative disease (LPD) in immuno-compromised hosts and with a variety of different types of human B-cell lymphomas, such as endemic Burkitt lymphoma (BL), Hodgkin lymphoma (HL), and a subset of diffuse large B cell lymphomas (DLBCLs).

EBV can infect cells in either latent or lytic forms. During latent EBV infection, the virus persists as a nuclear episome and is replicated once per cell cycle. Expression of 9 latent viral proteins in EBV-infected cells with type III latency is sufficient to transform primary B cells in vitro. EBV-infected tumors are composed primarily of cells latent forms of EBV infection and therefore the latent viral proteins have been widely explored as antigens to activate and expand adoptive cytotoxic T lymphocytes (CTLs) used as a cell therapy to treat PTLDs or EBV-lymphomas (Papadopoulou, Gerdemann et al. 2014).

Limitations of current methods for generation of adoptive T cells include the long time and complexity of standard-operating procedures for T cell manipulation. These methods rely on the presence of high affinity T cell receptors (TCRs) on the cell membrane of memory T cells, which upon signalling induce T cell expansion, cytokine production (particularly through CD4+ T helper cells) and effector functions to kill EBV latently infected cells (particularly through CD8+ T cytotoxic cells). T cells obtained from cord blood or from EBV seronegative donors lack expression of high-affinity TCRs and memory T cells against EBV and are inefficiently expanded in vitro with EBV antigens (in the form of proteins or peptides). Use of clinical grade CTLs is available only in selected centers and a challenge is to produce T cells in a timely manner for every patient in need. Therefore, new approaches are warranted.

CTLs can be genetically engineered and redirected to recognize and kill cells by means of specific CARs (Dotti, Gottschalk et al., 2014). CARs consist of transmembrane fusion proteins containing a variable antigen binding domain in the ectodomain fused to a spacer and an intracellular domain that triggers T cell stimulation (typically CD28/CD34ζ or "CD28.zeta"; 4-1BB/CD34ζ or "4-1BB.zeta").

The single chain variable fragments (scFv) fused to CARs recognize cell lineage antigens or receptors expressed on the surface of target cells. scFv binding with high affinity to the cell surface are required for effective CAR cytotoxic functions. The most clinically successful CAR-T cells are targeted against B cell malignancies through recognition of CD19.

Previously, CARs against herpes virus proteins have been disclosed (WO2015136001), including those expressed in the latent phase (WO2016201124, Tang et al., 2014), such as LMP-1/2. No herpes virus antigens are disclosed as targets of a CAR that are present on the surface of a cell latently infected with a herpes virus, and that support the lytic phase of viral replication.

WO2017172981 discloses various CAR constructs and modified cells for use in the treatment of cancer, the modified cells comprising CARs and K13-vFLIP signalling proteins, and the CARs comprising an immunoreceptor tyrosine-based activation motif located at the C-terminus of the CAR. No data or therapeutic effects are disclosed for CAR constructs targeting herpes virus antigens.

Von Laer et al (Handbook of Experimental Pharmacology, vol. 189, 2009, 265-297) review antiviral gene therapy and discuss the use of adoptive T cell therapy in the treatment of EBV-associated lymphoma and chronically active EBV infection. The use of receptor-modified, retargeted T cells, for example by means of an artificial chimeric T cell receptor directed against HIV antigens, is mentioned. No mention is made of targeting herpes virus antigens using chimeric antigen receptor technology.

Although a number of potential alternatives for targeting herpes virus antigens by immunotherapy are in development, a significant need remains for providing effective means for addressing medical disorders associated with human herpesvirus.

SUMMARY OF THE INVENTION

In light of the prior art the technical problem underlying the invention was the provision of alternative or improved means for treating and/or preventing diseases associated with human herpesvirus.

This problem is solved by the features of the independent claims. Preferred embodiments of the present invention are provided by the dependent claims.

Therefore, the invention relates to a chimeric antigen receptor polypeptide (CAR), comprising:
  i. an extracellular antigen-binding domain, comprising an antibody or antibody fragment that binds to a protein encoded by a herpes virus or to a protein complex comprising said protein (herpes virus antigen), wherein said herpes virus antigen is present on the surface of a human cell that is latently infected with said herpes virus and supports the lytic phase of viral replication,
  ii. a transmembrane domain, and
  iii. an intracellular signaling domain.

The invention is therefore characterized essentially as a CAR targeted to one of a sub-set of herpes virus antigens that are presented on the surface of latently infected cells, such that the antigen is accessible to CAR targeting, and that are involved in and/or support the lytic phase of viral replication. This unique subset represents a novel group of herpes antigen targets not previously suggested in the art that enables an alternative approach towards directing cytolytic activity of immune cells in a targeted manner to herpes virus infected cells.

Although latent phase herpes proteins have been identified previously as immunotherapy targets (Papadopoulou, Gerdemann et al., 2014, Tang et al., 2014), proteins presented on the cell surface of infected cells during latency but involved in the lytic phase of viral replication have not previously been proposed. This subgroup of target antigens enables targeting of herpes infected cells during latent infection, but represents a novel class of target antigens that appear to be present in sufficient numbers on the cell surface of a latently infected cell, thereby surprisingly enabling effective cytolytic activity upon targeting with a CAR T or other correspondingly modified immune cell. No suggestion exists in the art that herpes virus proteins associated with lytic replication are also presented on the cell surface of latently infected cells in sufficient amounts to enable the cytotoxicity of a CAR modified immune cell as described herein.

In one embodiment, the CAR polypeptide of the present invention is characterized in that the herpes virus antigen is involved in the virus binding to a receptor on a target human cell (herpes virus receptor binding protein). This functional characterization presents a further preferred definition of a sub-group of target antigens of the present invention.

The "herpes virus receptor binding proteins" are those involved in direct recognition and binding between a virus particle and a receptor on the surface of a cell to be infected. Typically, herpes virus infection is initiated when a viral particle contacts a cell with specific types of receptor molecules on the cell surface. Following binding of herpes virus receptor binding proteins (such as envelope glycoproteins) to cell membrane receptors, the virion is internalized and dismantled, allowing viral DNA to migrate to the cell nucleus. The herpes virus proteins involved in this receptor binding and infection of a host cell are preferred targets of the CAR of the present invention.

This strategy enables the targeting of a subset of herpes viral proteins presented on the surface of infected cells during latency, but which are also involved in cell surface receptor binding. No suggestion exists in the art that herpes virus proteins associated with lytic replication, and also involved in host cell receptor binding during infection, are also presented on the cell surface of latently infected cells in sufficient amounts to enable the cytotoxicity of a CAR modified immune cell as described herein.

Multiple herpes virus proteins are known that exhibit the above defined functional features. Preferred targets are therefore those described in Table 1 or Table 2.

TABLE 1

Human herpes virus proteins involved in cell surface and membrane of infected cells and/or viral particles. HSV-2 and HHV-7 are not included, since their nomenclatures are the same as those for HSV-1 and HHV-6, respectively (modified from Human Herpesviruses: Biology, Therapy, and Immunoprophylaxis, 2007).

| HSV-1 | VZV | HCMV | HHV-6 | EBV | HHV-8 | Function/ alternative nomenclature |
|---|---|---|---|---|---|---|
| UL11 | 49 | UL99 | U71 | BBLF1 | 38 | Role in virion egress and secondary envelopment in the cytoplasm; myristylated and palmitylated protein; interacts with UL16 protein |
| UL27 | 31 | UL55 | U39 | BALF4 | 8 | gB |
| UL1 | 60 | UL115 | U82 | BKRF2 | 47 | gL; complexed with gH |
| UL22 | 37 | UL75 | U48 | BXLF2 | 22 | gH; complexed with gL |
| UL10 | 50 | UL100 | U72 | BBRF3 | 39 | gM; complexed with gN |
| UL49A | 9A | UL73 | U46 | BLRF1 | 53 | gN; complexed with gM; not glycosylated in some herpesviruses |

Further herpes virus antigens present on the surface of a human cell latently infected with said herpes virus and supporting the lytic phase of viral replication are:

From EBV gB, gH, gL, or BILF1,

From HCMV gB (UL55), UL73, UL74 (gO), UL75 (gH), UL115 (gL), US27, UL100, UL132, RL10;

In addition to US20, UL148D, UL78, UL119, UL16, UL40, US6, UL136, US14, RL12, US28, RL11, US9, UL33, UL144, UL141 (Weekes et al., 2014).

Recently, methods have been established (Weekes et al., 2014) enabling the identification of cell surface presented herpes viral antigens, and the role of these proteins in the latent and/or lytic viral replication cycle has been interrogated previously, thereby enabling a skilled person in the identification of the sub-group of viral target antigens described herein.

A skilled person is capable of determining whether a herpes virus antigen is involved in and/or support the lytic phase of viral replication, for example by determining expression of the antigen during the lytic phase.

In a preferred embodiment the CAR polypeptide of the present invention is characterized in that the herpes virus antigen is an EBV antigen. In preferred embodiments the invention is focused on targeting EBV-antigens and treating EBV-associated medical conditions. In a preferred embodiment the herpes viral antigen is the EBV glycoprotein 350/220 (gp350/gp220).

In a preferred embodiment the CAR polypeptide of the present invention is characterized in that the EBV antigen is present on the surface of EBV-infected cells.

In a preferred embodiment the CAR polypeptide of the present invention is characterized in that the EBV antigen is present on the surface of EBV-infected cancer cells, EBV-infected B cells or EBV-infected epithelial cells.

Using the methods described herein, and cited methods already established in the field, the viral antigens (in addition to those specific antigens described herein) to be targeted can be identified by a skilled person without undue effort.

A sub-group of antigens present on the surface of EBV-infected cells, and potentially on latently infected malignant cells, consists of: gp350/gp220, LMP1, LMP2, BILF1, BALF4 (gB), BKRF2 (gL), BXLF2 (gH), BBRF3 (gM), BLRF1 (gN). Of these, in particular, gp350/gp220, BILF1, BALF4 (gB), BKRF2 (gL), BXLF2 (gH), BBRF3 (gM), BLRF1 (gN) are preferred and considered to support the lytic phase of viral replication.

In a preferred embodiment the CAR polypeptide of the present invention is characterized in that the EBV antigen is an EBV virion envelope protein or a protein of the EBV envelope complex.

In a preferred embodiment the CAR polypeptide of the present invention is characterized in that the EBV antigen is the EBV gp350/gp220. In other words, the invention is preferably characterized in that the extracellular antigen-binding domain, comprising an antibody or antibody fragment, binds the EBV gp350/gp220.

In preferred embodiments the invention therefore relates to gp350/gp220-CARs.

Further preferred protein targets are therefore gB, gL or gH. Additionally, other EBV glycoproteins are known to be involved in the lytic phase of replication, in the EBV virion envelope protein and/or a protein of the EBV envelope complex (Table 2, Hutt-Fletcher, 2015).

TABLE 2

Summary of EBV glycoproteins (modified from Hutt-Fletcher, 2015)

| Gene | Protein | Type | Expression | Function |
|---|---|---|---|---|
| BLLF1 | gp350/220 | Single pass type 1 membrane | Late lytic/ structural | Attachment |
| BALF4 | gB | Single pass type 1 membrane | Late lytic/ structural | Fusion |
| BXLF2 | gH | Single pass type 1 membrane | Late lytic/ structural | Regulation and triggering of fusion |
| BKRF2 | gL | Soluble associated with gH | Late lytic/ structural | Regulation and triggering of fusion |
| BZLF2 | gp42 | Single pass type 2 membrane/soluble | Late lytic/ structural | Triggering of fusion/ immune evasion |
| BBRF3 | gM | Multispanning membrane | Late lytic/ structural | Assembly and release |
| BLRF2 | gN | Single pass type 1 membrane | Late lytic/ structural | Assembly and release |
| BMRF2 | BMRF2 | Multispanning membrane | Late lytic/ structural | Epithelial cell attachment and spread |
| BDLF2 | BDLF2 | Single pass type 2 membrane | Late lytic/ structural | Epithelial spread? |
| BDLF3 | BDLF3 | Single pass type 1 membrane | Late lytic/ structural | Unknown |
| BILF2 | BILF2 | Single pass type 1 membrane | Late lytic/ structural | Unknown |
| BILF1 | BILF1 | Multispanning membrane | Immediate early/early | G-protein-coupled receptor/immune evasion |
| BARF1 | BARF1 | Secreted | Latent and early lytic | CSF1 receptor/ immune evasion |

The CAR polypeptide of the present invention comprises therefore an extracellular antigen-binding domain, comprising an antibody or antibody fragment that binds to a protein encoded by a herpes virus or to a protein complex comprising said protein (herpes virus antigen), wherein said herpes virus antigen is present on the surface of a human cell that is latently infected with said herpes virus and supports the lytic phase of viral replication. The herpes virus protein antigens of Tables 1 and 2, in addition to those identified by Weekes et al., 2014, may be employed as targets for CAR-binding. Nomenclature for the definition of a herpes virus antigen based on one specific herpes virus, for example those in Table 1, also includes using such a corresponding homologous target from other herpes known viruses. The term "supports the lytic phase of viral replication" in preferred embodiments corresponds to one or more of expression during the lytic phase of viral replication (for example increased expression during the lytic phase compared to the latent phase), and/or performing a function essential to and/or primarily associated with lytic phase of viral replication.

In a preferred embodiment the herpes virus antigen is the EBV antigen gp350/gp220.

Preferred embodiments therefore relate to CARs and CAR T cells against an EBV lytic antigen target, preferably the glycoprotein 350 (gp350), which is required for binding of the EBV virus to B cells (through binding CD21 on the surface of human cells). The gp350 protein is also present in a shorter form (gp220). The protein gp350/gp220 is abundantly expressed in infected cells during EBV lytic reactivation, but its role in EBV latency has not been previously described. As such, the targeting of gp350/gp220 (as a lytic protein expressed on the surface of infected cells during latency) represents an entirely new approach towards targeting herpes virus infection using directed immunotherapy. Surprisingly, although cytotoxic $CD4^+$ T cells can be found (Adhikary, Behrends et al., 2006), $CD8^+$ T cells CTL responses directed against gp350/gp220, are rarely found in humans.

A clinical problem to be solved by the invention is therefore protecting patients (such as immune compromised patients) against herpes virus, such as EBV and EBV-associated malignancies. The technical problem is addressed by an immune cell therapy, preferably a T cell therapy, against herpes virus (preferably EBV) infected cells by inserting high-affinity single-chain antibody sequences into CARs to target herpes viral antigens (preferably EBV antigens) on the cell surface. T cells or other immune cells expressing these CARs will be activated by infected cells and result into potent and persistent anti-viral responses.

Adoptive T cells expanded ex vivo with EBV have relied so far on viral antigens that are presented through HLA to TCR on T cells for activation of cellular responses. The problems with this approach are: 1. EBV infection dysregulates the T cell activation and is associated with T cell exhaustion; and 2. HLA/TCR matching is required.

Compared with older methods to expand EBV-reactive T cells in vitro, the target recognition of the present invention is not mediated by HLA. Thus, CAR-T cells or other CAR-engineered immune cells targeted against EBV open the perspective for universal "off-the-shelf" cell therapies for immune compromised patients at high-risk of EBV infection, reactivation, infectious mononucleosis, PTLD or developing EBV-related malignancies.

In other preferred embodiments, the inventive CAR-engineered immune cells can be produced in a shorter period of time than HLA-binding antigen-expanded T cells. In some embodiments, CAR-engineered immune cells can be edited for deletion of TCRs to avoid GVHD reactions. In some embodiments, CAR-engineered immune cells can be edited for deletion of HLA to avoid allogeneic rejection and become "universal CAR-T cells". The advantages of the present approach therefore relate to increased specificity against viral antigens, no need for HLA matching and no need of memory T cells, as the inventive cells can in some embodiments be produced with naïve T cells from seronegative donors or from cord blood.

A further aspect of the invention therefore relates to a genetically modified immune cell comprising a nucleic acid molecule encoding and/or expressing a CAR of the present invention. The exemplary sequences provided below therefore may be present in immune cells, and represent preferred but non-limiting embodiments of the genetically modified immune cells of the present invention.

In preferred embodiments the immune cell is preferably a T lymphocyte, an NK cell, a macrophage or a dendritic cell. These immune cells are known in the field to exhibit cytotoxic and/or other beneficial activity in response to unwanted agents, cells or pathogens. By directing the activity of these cells to particular immunogenic targets, namely the herpes viral antigens described herein, infected pathogenic cells can be eliminated by the corresponding activity of the immune cell described herein.

In a preferred embodiment, the immune cell is a T lymphocyte, preferably a cytotoxic T lymphocyte or a T helper cell.

In some embodiments, the CAR-engineered immune cell could be engineered to additionally co-express cytokines (such as IL-15, IL-12, IFN-gamma, IFN-alpha, GM-CSF, FLT3L, IL-21, IL-23) or co-stimulatory ligands (CD80, CD86, CD40L) to improve the immune therapeutic effects.

In some embodiments, the CAR-engineered immune cell could be engineered to additionally co-express siRNAs or shRNAs or miRNAs to down-regulate, or could be genetically edited with CRISPR/Cas, to knock-out expression of the T cell receptor and the major histocompatibility complex, such that these cells can be used as allogeneic cell therapies.

In some embodiments, the CAR-engineered immune cell could be engineered to additionally co-express siRNAs or shRNAs or miRNAs to down-regulate, or genetically edited with the CRISPR/Cas, to knock-out expression of check point molecules on the T cell surface (PD1, Tim3, LAG, etc. . . . ).

Combined approaches employing down-regulation of the major histocompatibility complex or check point molecules on the T cell surface lead to additional, potentially synergistic effects, in optimizing the local immune environment to enhance the cytolytic effect of the CAR-engineered immune cells of the invention.

In some embodiments, the CAR-engineered immune cell could be engineered to additionally co-express additional CARs targeting particular cell lineages.

In some embodiments, naïve T cells from EBV seronegative donors or from cord blood could be efficiently and rapidly converted into gp350/gp220-CAR-T cells for use in the medical treatments described herein. Further guidance on the production of immune cells engineered to express the inventive CARs is presented below.

A further aspect of the invention relates therefore to an immune cell as described herein for use in the treatment or prevention of a medical condition associated with herpes virus infection. The invention therefore also encompasses methods for treating or preventing a medical condition associated with herpes virus infection, comprising the administration of an immune cell as described herein (comprising/expressing a CAR of the present invention) to a subject in need thereof.

In some embodiments, the immune cell for use as a medicament, or corresponding methods of treatment, are therefore preferably employed in the treatment of herpes virus-associated cancers, chronic active herpes virus infections or primary herpes virus infections.

In preferred embodiments the medical condition to be treated may be defined by the presence of a target on pathogenic cells associated with the condition. For example, the invention encompasses the immune cell for use as a medicament as described herein, wherein the medical condition associated with herpes virus infection is a herpes virus-associated cancer in which herpes virus-antigens are present on the surface of cancer cells.

Methods for identifying such antigens are known to a skilled person, thereby enabling a skilled person to identify the medical condition for treatment or prevention using such methods. For example, the methods as described in Weekes et al, 2014, show how cell surface presentation of herpes viral antigens can be identified. Any given cancer may therefore be assessed in order to determine whether a herpes viral antigen is present on the cell surface of a cancerous cell. The identification of cancer types using such methods will enable a skilled person to identify treatable conditions using the CARs and immune cells of the present invention.

A sub-group of antigens present on the surface of EBV-infected cells, and potentially on latently infected malignant cells, consists of: gp350/gp220, LMP1, LMP2, BILF1, BALF4 (gB), BKRF2 (gL), BXLF2 (gH), BBRF3 (gM), BLRF1 (gN). Of these, in particular gp350/gp220, BILF1, BALF4 (gB), BKRF2 (gL), BXLF2 (gH), BBRF3 (gM), BLRF1 (gN) are preferred and considered to support the lytic phase of viral replication.

In a preferred embodiment the immune cell for use as a medicament (or corresponding methods of treatment) as described herein are intended for treating medical conditions associated with infection with EBV.

In a preferred embodiment, the immune cell for use as a medicament (or corresponding methods of treatment) as described herein, is characterized in that the medical condition is an EBV-associated cancer, selected preferably from a lymphoproliferative disorder (LPD), such as B-cell lymphoma, including Burkitt lymphoma (BL), Hodgkin lymphoma (HL), a diffuse large B cell lymphoma (DLBCL), or a post-transplant lymphoproliferative disorder (PTLD), or an epithelial carcinoma (nasopharyngeal, lung, breast), a lymphoepithelioma, a carcinoma with lymphoid stroma (GCLS, e.g. gastric carcinoma) or a glioma. A skilled person is aware that cancer types such as these are known to be associated with EBV infection. Targeting an immune cell using the CARs of the present invention against these cancer types therefore represents a promising therapeutic option.

In other embodiments the immune cell for use as a medicament (or corresponding methods of treatment) as described herein, is characterized in that the medical condition associated with EBV infection is chronic active EBV infection (CAEBV) or primary EBV infection (e.g. mononucleosis).

In other embodiments the immune cell for use as a medicament (or corresponding methods of treatment) as described herein, is intended for the treatment of immune deficient or immune compromised patients after chemotherapy, radiation, immune suppression or transplantation.

As described herein, multiple antibodies (or fragments thereof) may be employed as the antigen binding domain. In preferred embodiments, particular antibody fragments as described herein are employed. In preferred embodiments, single chain variable fragments comprising variable heavy chain (VH) and variable light chain (VL) domains as described herein are employed. In the following, two antigen binding fragments are employed, for which the nomenclature "7A1" and "6G4", each representing unique antigen binding fragments, is used.

Novel antibodies reactive against gp350 were generated. The properties of two antibodies neutralizing EBV infection of Raji cells in vitro, 7A1 and 6G4, have not been previously disclosed in the art. The inventors have demonstrated proof-of-concept for function of T cells expressing chimeric antigen receptors (CAR-T cells) incorporating the 7A1 and 6G4 single chain antibodies (see examples below). As targets, cell lines genetically modified for gp350/gp220 expression and a marmoset B cell line latently infected with EBV (B95.8) were used. The inventors show in vitro that gp350-CAR-T cells strongly reacted against the B95.8 latently infected cell line resulting in production of IFN-gamma, B95.8 cell death, selection of cells negative for gp350 expression and reduction of the number of episomal EBV DNA after killing. B cells immortalized with the EBV laboratory strain M81 were also recognized by gp350-CAR-T cells, which produced IFN gamma, expanded and showed reduction of gp350 expression.

In a preferred embodiment the CAR polypeptide of the invention is characterized in that the antigen-binding domain (7A1) comprises a variable heavy chain (VH), said VH comprising:

heavy chain complementary determining regions H-CDR1 according to SEQ ID NO: 1 (GLSLTSN), H-CDR2 according to SEQ ID NO: 2 (WSNGG), and H-CDR3 according to SEQ ID NO: 3 (PRYNSGYFFDY), or one or more corresponding CDR sequences of at least 80% sequence identity to SEQ ID NOs 1 to 3;

and a variable light chain (VL), said VL comprising:

light chain complementary determining regions L-CDR1 according to SEQ ID NO: 4 (KASESVSTRMH), L-CDR2 according to SEQ ID NO: 5 (KTSNLAS), and L-CDR3 according to SEQ ID NO: 6 (QQSWNGPLT), or one or more corresponding CDR sequences of at least 80% sequence identity to SEQ ID NOs 4 to 6.

In a preferred embodiment the CAR polypeptide of the invention is characterized in that the antigen-binding domain (6G4) comprises a variable heavy chain (VH), said VH comprising:

heavy chain complementary determining regions H-CDR1 according to SEQ ID NO: 7 (GFSLTSY), H-CDR2 according to SEQ ID NO: 8 (WSDGD), and H-CDR3 according to SEQ ID NO: 9 (LQSEDTATYY-CARLQVFGYPGIRDYVMDA), or one or more corresponding CDR sequences of at least 80% sequence identity to SEQ ID NOs 7 to 9;

and a variable light chain (VL), said VL comprising:

light chain complementary determining regions L-CDR1 according to SEQ ID NO: 10 (KSSQSLLSSRHQKN-FLA), L-CDR2 according to SEQ ID NO: 11 (HAS-TRQS), and L-CDR3 according to SEQ ID NO: 12 (LQHYTSPYT), or a sequence of at least 80% sequence identity to SEQ ID NOs 10 to 12.

In a preferred embodiment the CAR polypeptide of the invention is characterized in that the extracellular antigen-binding domain comprises:

a VH domain that comprises CDR sequences of SEQ ID NO: 1, SEQ ID NO: 2, and SEQ ID NO: 3, and a VL domain that comprises CDR sequences of SEQ ID NO: 4; SEQ ID NO: 5, and SEQ ID NO: 6 (7A1), or a VH domain that comprises CDR sequences of SEQ ID NO: 7, SEQ ID NO: 8, and SEQ ID NO: 9, and a VL domain that comprises CDR sequences of SEQ ID NO: 10, SEQ ID NO: 11, and SEQ ID NO: 12 (6G4).

In one embodiment the CAR polypeptide comprises a VH domain with at least 80% sequence identity, preferably at least 85%, 90%, 95% or with 100% sequence identity, to SEQ ID NO: 13:

QVQLKESGPGLVQPSQTLSLTCTVSGX1SLTSX2X3VX4WX5RQPPGK

GLEWX6GVX7WSX8GX9TX10YNSAX11KSRLSX12SRDTSKSQVX13

LX14MX15SLQX16EDTAX17YX18CARX19X20X21X22X23YX24

X25X26X27X28YX29X30DX31WGQGX32X33VTVSS, wherein X1: L or F; X2: N or Y; X3: G or H; X4: S or H; X5: I or V; X&: L or M; X7: I or M, X8: N or D; X9: G or D; X10: D or L; X11: I or L; X12: F or I; X13: F or L; X14: K or Q; X15: N or D; X16: T or S; X17: M or T; X18: F or Y; X19: P or L; X20: R or Q; X21: no AA or V; X22: no AA or F; X23: no AA or G; X24: N or P; X25: S or G; X26: no AA or I; X27: no AA or R; X28: G or D; X29: F or V; X30: F or M; X31: Y or A; X32: V or A; X33: M or S (wherein "no AA" means "no amino acid");

and a VL domain with at least 80% sequence identity, preferably at least 85%, 90%, 95% or with 100% sequence identity, to SEQ ID NO: 14:

DX1VX2TQSPX3X4LAVSX5GEX6VTIX7CKX8SX9SX10X11X12X13

X14HX15X16X17X18X19X20WYRQKPGQX21PKLLIYX22X23SX24

X25X26SGVPX27RFX28GSGSGTDFTLTIX29X30VX31AX32DX33A

X34YX35CX36QX37X38X39X40PX41TFGX42GTKLEX43KR, wherein X1: T or L; X2: L or M; X3: no AA or F; X4: A or S; X5: P or E; X6: R or M; X7: S or K; X8: A or S; X9: E or Q; X10: V or L; X11: S or L; X12: T or S; X13: R or S; X14: M or R; X15: no AA or Q; X16: no AA or K; X17: no AA or N; X18: no AA or F; X19: no AA or L; X20: no AA or A; X21: Q or S; X22: K or H; X23: T or A; X24: N or T; X25: L or R; X26: A or Q; X27: A or D; X28: S or I; X29: D or S; X30: P or D; X31: E or Q; X32: D or E; X33: T or L; X34: T or D; X35: F or Y; X36: Q or L; X37: S or H; X:38: W or Y; X39: N or T; X40: G or S; X41: L or Y; X42: S or A; X43: I or L (wherein "no AA" means "no amino acid").

The above-mentioned sequences according to SEQ ID NOs 13 and 14 represent unified representations of the antigen binding fragment VL and VH sequences, showing amino acids common to both 7A1 and 6G4, as specific amino acids in the recited sequence, and showing amino acids, which may vary according to either of 7A1 and 6G4, named as an "X" with the corresponding options listed for each "X" beneath the sequence. The 7A1 and 6G4 antigen binding fragments of the present invention represent therefore unitary subject matter, each of which is capable of binding EBV gp350 and enabling the beneficial efficacy of the CAR of the present invention. Common structural elements with respect to their sequences are evident.

In one embodiment the CAR polypeptide of the present invention comprises a VH domain according to:

SEQ ID NO 15: (7A1)
(QVQLKESGPGLVQPSQTLSLTCTVSGLSLTSNGVSWIRQPPGKGLEWL

GVIWSNGGTDYNSAIKSRLSFSRDTSKSQVFLKMNSLQTEDTAMYFCAR

PRYNSGYFFDYWGQGVMVTVSS)

and a VL domain according to:

SEQ ID NO: 16 (7A1)
(DTVLTQSPALAVSPGERVTISCKASESVSTRMHWYRQKPGQQPKLLIY

KTSNLASGVPARFSGSGSGTDFTLTIDPVEADDTATYFCQQSWNGPLTF

GSGTKLEIKR), or
a VH domain according to:

SEQ ID NO: 17 (6G4)
(QVQLKESGPGLVQPSQTLSLTCTVSGFSLTSYHVHWVRQPPGKGLEWM

GVMWSDGDTLYNSALKSRLSISRDTSKSQVLLQMDSLQSEDTATYYCAR

LQVFGYPGIRDYVMDAWGQGASVTVSS)

and a VL domain according to:

SEQ ID NO: 18 (6G4)
(DLVMTQSPFSLAVSEGEMVTIKCKSSQSLLSSRHQKNFLAWYRQKPGQ

SPKLLIYHASTRQSGVPDRFIGSGSGTDFTLTISDVQAEDLADYYCLQH

YTSPYTFGAGTKLELKR).

In further embodiments of the invention particular CAR constructs are employed, using for example specific leader polypeptides, linker polypeptides positioned between the VH and VL domains, spacer polypeptides positioned between the extracellular antigen-binding domain and the trans-membrane domain, transmembrane domains, intracellular domains, and/or linker polypeptides positioned between the VH and VL domains and the spacer, and/or between the spacer and the transmembrane domain.

The embodiments described below represent preferred but non-limiting embodiments of the CAR constructs developed by the inventors. Variation in the particular domains described below is contemplated and encompassed within the scope of the invention.

In one embodiment the CAR polypeptide of the present invention comprises a leader polypeptide positioned N-terminally of the VH and VL domains, wherein said leader polypeptide is preferably an IgHL leader.

In one embodiment the leader polypeptide is preferably an IgHL leader according to SEQ ID NO: 19 (MEFGLSWLFLVAILKGVQC), or a leader with at least 80% sequence identity to SEQ ID NO: 19.

In one embodiment the CAR polypeptide of the present invention is characterized in that the extracellular antigen-binding domain comprises a linker polypeptide positioned between the VH and VL domains, wherein said linker is preferably a G4S linker.

In one embodiment the linker is preferably a G4S linker according to SEQ ID NO: 20 (SGGGGSGGGGSGGGGS) linker, or a linker with at least 80% sequence identity to SEQ ID NO: 20.

In one embodiment the CAR polypeptide of the present invention comprises additionally a spacer polypeptide positioned between the extracellular antigen-binding domain and the transmembrane domain, wherein said spacer is preferably an IgG1 CH3 or an IgG1 CH2-CH3 spacer.

In one embodiment the spacer is preferably an IgG1 CH3 spacer according to SEQ ID NO: 21 (ESKY-GPPCPPCPGQPREPQVYTLPPSRDELTKNQVSLT-CLVKGFYPSDIAVEWESNGQPENNYKT TPPVLDSDGSFFLYSK-LTVDKSRWQQGNVFSCSVMHEALHNHYTQKSLSL-SPGKESKYGPPCPPC PGQPREPQVYTLPPSRDELT-KNQVSLTCLVKGFYPSDIAVEWESNGQPENNYKTTPP VLDSDGSFF LYSK-LTVDKSRWQQGNVFSCSVMHEALHNHYTQKSLSL-SPGK), or a spacer with at least 80% sequence identity to SEQ ID NO: 21.

In one embodiment the spacer is preferably an IgG1 CH2 CH3 spacer according to SEQ ID NO: 22 (EPKSPDKTH-TCPPCPAPELLGGPSVFLFPPKPKDTLMISRTPE-VTCVVVDVSHEDPEVKFNWYVDG VEVHNAKTKPREEQYN-STYRVVSVLTVLHQDWLNGKEYKCKVSNKALPA-PIEKTISKAKGQPREPQ VYTLPPSRDELTKNQVSLT-CLVKGFYPSDIAVEWESNGQPENNYKTTPPVLDSDGS FFLYSKLTVDK SRWQQGNVFSCSVMHEALHN-HYTQKSLSLSPGK), or a spacer with at least 80% sequence identity to SEQ ID NO: 22.

In one embodiment the CAR polypeptide of the present invention is characterized in that the transmembrane domain is a CD28 or a CD8 alpha transmembrane domain.

In one embodiment the transmembrane domain is a CD28 transmembrane domain, preferably according to SEQ ID NO: 23 (FWVLVVVGGVLACYSLLVTVAFIIFWVRS), or a transmembrane domain with at least 80% sequence identity to SEQ ID NO: 23.

In one embodiment the transmembrane domain is a CD8 alpha transmembrane domain, preferably according to SEQ ID NO: 24 (VISTSGRPWPGLVGSFSCHWLSPFTATTG), or a transmembrane domain with at least 80% sequence identity to SEQ ID NO: 24.

In one embodiment the CAR polypeptide of the present invention is characterized in that the intracellular domain comprises a CD28 or a 4-1BB co-stimulatory domain.

In one embodiment intracellular domain comprises a CD28 co-stimulatory domain, preferably according to SEQ ID NO: 25 (KRSRLLHSDYMNMTPRRPGPTRKHYQPY-APPRDFAAYRS), or a co-stimulatory domain with at least 80% sequence identity to SEQ ID NO: 25.

In one embodiment intracellular domain comprises a 4-1BB co-stimulatory domain, preferably according to SEQ ID NO: 26 (KRGRKKLLY-IFKQPFMRPVQTTQEEDGCSCRFPEEEEGGCEL), or a co-stimulatory domain with at least 80% sequence identity to SEQ ID NO: 26.

In one embodiment the CAR polypeptide of the present invention is characterized in that the intracellular domain comprises a CD3 zeta chain signaling domain.

In one embodiment the CD3 zeta chain signaling domain is preferably according to SEQ ID NO: 27 (RVKFSRSADA-PAYQQGQNQLYNELNLGRREEYDVLDKRR-GRDPEMGGKPRRKNPQEGLYNELQ KDKMAEAYSEI-GMKGERRRGKGHDGLYQGLSTATKDPTTPFTCRPCPL), or a signaling domain with at least 80% sequence identity to SEQ ID NO: 27.

In one embodiment the CAR polypeptide of the present invention is characterized in that the CAR comprises one or more linker polypeptides positioned between the VH and VL domains and the spacer, and/or between the spacer and the transmembrane domain.

In one embodiment the one or more linker polypeptides positioned between the VH and VL domains and the spacer, and/or between the spacer and the transmembrane domain, is preferably selected from a sequence according to SEQ ID NO: 28 (GDPA) or SEQ ID NO: 29 (KDPK).

In preferred embodiments, the invention relates to a CAR polypeptide as described herein, comprising or consisting of a sequence according to:

SEQ ID NO: 30 (7A1 CAR.CD28.z)
MEFGLSWLFLVAILKGVQCQVQLKESGPGLVQPSQTLSLTCTVSGLSLT
SNGVSWIRQPPGKGLEWLGVIWSNGGTDYNSAIKSRLSFSRDTSKSQVF
LKMNSLQTEDTAMYFCARPRYNSGYFFDYWGQGVMVTVSSSGGGGSGG
GSGGGGSDTVLTQSPALAVSPGERVTISCKASESVSTRMHWYRQKPGQQ
PKLLIYKTSNLASGVPARFSGSGSGTDFTLTIDPVEADDTATYFCQQSW
NGPLTFGSGTKLEIKGDPAESKYGPPCPPCPGQPREPQVYTLPPSRDEL
TKNQVSLTCLVKGFYPSDIAVEWESNGQPENNYKTTPPVLDSDGSFFLY
SKLTVDKSRWQQGNVFSCSVMHEALHNHYTQKSLSLSPGKKDPKFWVLV
VVGGVLACYSLLVTVAFIIFWVRSKRSRLLHSDYMNMTPRRPGPTRKHY
QPYAPPRDFAAYRSRVKFSRSADAPAYQQGQNQLYNELNLGRREEYDVL
DKRRGRDPEMGGKPRRKNPQEGLYNELQKDKMAEAYSEIGMKGERRRGK
GHDGLYQGLSTATKDTYDALHMQALPPR, or

SEQ ID NO: 31 (6G4 CAR.CD28.z)
MEFGLSWLFLVAILKGVQCQVQLKESGPGLVQPSQTLSLTCTVSGFSLT
SYHVHWVRQPPGKGLEWMGVMWSDGDTLYNSALKSRLSISRDTSKSQVL
LQMDSLQSEDTATYYCARLQVFGYPGIRDYVMDAWGQGASVTVSSSGGG
GSGGGGSGGGGSDLVMTQSPFSLAVSEGEMVTIKCKSSQSLLSSRHQKN
FLAWYRQKPGQSPKLLIYHASTRQSGVPDRFIGSGSGTDFTLTISDVQA
EDLADYYCLQHYTSPYTFGAGTKLELKGDPAESKYGPPCPPCPGQPREP
QVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLS
PGKKDPKFWVLVVVGGVLACYSLLVTVAFIIFWVRSKRSRLLHSDYMNM
TPRRPGPTRKHYQPYAPPRDFAAYRSRVKFSRSADAPAYQQGQNQLYNE
LNLGRREEYDVLDKRRGRDPEMGGKPRRKNPQEGLYNELQKDKMAEAYS
EIGMKGERRRGKGHDGLYQGLSTATKDPTTPFTCRPCPL, or

SEQ ID NO: 32 (7A1 CAR.41BB.z)
MEFGLSWLFLVAILKGVQCQVQLKESGPGLVQPSQTLSLTCTVSGLSLT
SNGVSWIRQPPGKGLEWLGVIWSNGGTDYNSAIKSRLSFSRDTSKSQVF
LKMNSLQTEDTAMYFCARPRYNSGYFFDYWGQGVMVTVSSSGGGGSGGG
GSGGGGSDTVLTQSPALAVSPGERVTISCKASESVSTRMHWYRQKPGQQ
PKLLIYKTSNLASGVPARFSGSGSGTDFTLTIDPVEADDTATYFCQQSW
NGPLTFGSGTKLEIKGDPAEPKSPDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSL
SLSPGKKDPKFWVISTSGRPWPGLVGSFSCHWLSPFTATTGKRGRKKLL
YIFKQPFMRPVQTTQEEDGCSCRFPEEEEGGCELRVKFSRSADAPAYQQ
GQNQLYNELNLGRREEYDVLDKRRGRDPEMGGKPRRKNPQEGLYNELQK
DKMAEAYSEIGMKGERRRGKGHDGLYQGLSTATKDTYDALHMQALPPR,
or

SEQ ID NO: 33 (6G4 CAR.41BB.z)
MEFGLSWLFLVAILKGVQCQVQLKESGPGLVQPSQTLSLTCTVSGFSLT
SYHVHWVRQPPGKGLEWMGVMWSDGDTLYNSALKSRLSISRDTSKSQVL
LQMDSLQSEDTATYYCARLQVFGYPGIRDYVMDAWGQGASVTVSSSGGG
GSGGGGSGGGGSDLVMTQSPFSLAVSEGEMVTIKCKSSQSLLSSRHQKN
FLAWYRQKPGQSPKLLIYHASTRQSGVPDRFIGSGSGTDFTLTISDVQA
EDLADYYCLQHYTSPYTFGAGTKLELKGDPAEPKSPDKTHTCPPCPAPE
LLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMH
EALHNHYTQKSLSLSPGKKDPKFWVISTSGRPWPGLVGSFSCHWLSPFT
ATTGKRGRKKLLYIFKQPFMRPVQTTQEEDGCSCRFPEEEEGGCERVKF
SRSADAPAYQQGQNQLYNELNLGRREEYDVLDKRRGRDPEMGGKPRRKN
PQEGLYNELQKDKMAEAYSEIGMKGERRRGKGHDGLY.

In further embodiments, the CAR of the present invention is characterized in that the extracellular antigen-binding domain is an antibody selected from a full-length antibody, a single-chain antibody, an Fab fragment, an Fab' fragment, an (Fab')2 fragment, an Fv fragment, and a divalent single chain antibody or a diabody.

In further embodiments, the CAR of the present invention is characterized in that the co-stimulatory domain (transmembrane and intracellular signaling domain) comprises a signaling domain from any one or more of CD28, CD137 (4-1BB), CD134 (OX40), DaplO, CD27, CD2, CD5, ICAM-1, LFA-1, Lck, TNFR-J, TNFR-II, Fas, CD30, CD40 and combinations thereof.

In further embodiments, the CAR of the present invention is characterized in that the transmembrane domain is selected from an artificial hydrophobic sequence and transmembrane domains of a Type I transmembrane protein, an alpha, beta or zeta chain of a T cell receptor, CD28, CD3 epsilon, CD45, CD4, CD5, CD8, CD9, CD16, CD22, CD33, CD37, CD64, CD80, CD86, CD134, CD137, and CD154.

In further embodiments, the CAR of the present invention is characterized in that the intracellular signaling domain comprises a signaling domain of one or more of a human CD3 zeta chain, FcγRIII, FcεRI, a cytoplasmic tail of a Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d, and combinations thereof.

A further aspect of the invention relates to an isolated nucleic acid molecule, preferably in the form of an isolated vector, such as an isolated viral vector, comprising a nucleotide sequence which encodes a CAR polypeptide according to any one of the preceding claims.

In a preferred embodiment, the invention relates to an isolated nucleic acid molecule, preferably in the form of an isolated vector, such as an isolated viral vector, selected from the group consisting of:

a) a nucleic acid molecule comprising a nucleotide sequence
   which encodes a CAR polypeptide as described herein,
   which encodes an extracellular antigen-binding domain or part thereof comprising one or more of SEQ ID NOs 13-18,
   which encodes a CAR polypeptide according to SEQ ID NOs 30-33;
   according to one or more of SEQ ID NOs 34-37, b) a nucleic acid molecule which is complementary to a nucleotide sequence in accordance with a);

c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 80%;

d) a nucleic acid molecule which, as a consequence of the genetic code, is degenerated into a nucleotide sequence according to a) through c); and/or e) a nucleic acid molecule according to a nucleotide sequence of a) through d) which is modified by deletions, additions, substitutions, translocations, inversions and/or insertions and is functionally analogous/equivalent to a nucleotide sequence according to a) through d).

An additional and surprising aspect of the invention is an improved stability of the CAR as disclosed herein. The CAR polypeptide can readily be stored for extended periods under appropriate conditions without any loss of binding affinity.

Preferred amino acid and nucleotide sequences of the present invention:

| SEQ ID NO | Sequence | Description |
|---|---|---|
| 1 | GLSLTSN | 7A1 H-CDR1 |
| 2 | WSNGG | 7A1 H-CDR2 |
| 3 | PRYNSGYFFDY | 7A1 H-CDR3 |
| 4 | KASESVSTRMH | 7A1 L-CDR1 |
| 5 | KTSNLAS | 7A1 L-CDR2 |
| 6 | QQSWNGPLT | 7A1 L-CDR3 |
| 7 | GFSLTSY | 6G4 H-CDR1 |
| 8 | WSDGD | 6G4 H-CDR2 |
| 9 | LQSEDTATYYCARLQVFGYPGIRDYVMDA | 6G4 H-CDR3 |
| 10 | KSSQSLLSSRHQKNFLA | 6G4 L-CDR1 |
| 11 | HASTRQS | 6G4 L-CDR2 |
| 12 | LQHYTSPYT | 6G4 L-CDR3 |
| 13 | QVQLKESGPGLVQPSQTLSLTCTVSGX1SLTSX2X3VX4WX5RQPPGKGLEWX6GVX7WSX8GX9TX10YNSAX11KSRLSX12SRDTSKSQVX13LX14MX15SLQX16EDTAX17YX18CARX19X20X21X22X23YX24X25X26X27X28YX29X30DX31WGQGX32X33VTVSS wherein preferably X1: L or F; X2: N or Y; X3: G or H; X4: S or H; X5: I or V; X&: L or M; X7: I or M, X8: N or D; X9: G or D; X10: D or L; X11: 1 or L; X12: F or I; X13: F or L; X14: K or Q; X15: N or D; X16: T or S; X17: M or T; X18: F or Y; X19: P or L; X20: R or Q; X21: no AA or V; X22: no AA or F; X23: no AA or G; X24: N or P; X25: S or G; X26: no AA or I; X27: no AA or R; X28: G or D; X29: F or V; X30: F or M; X31: Y or A; X32: V or A; X33: M or S (wherein "no AA" means "no amino acid") | Unitary VH 7A1 and 6G4 |
| 13 | QVQLKESGPGLVQPSQTLSLTCTVSGXSLTSXXVXWXRQPPGKGLEWXGVXWSXGXTXYNSAXKSRLSXSRDTSKSQVXLXMXSLQXEDTAXYXCARXXXXXXXXXXXXYXXDXWGQGXXVTVSS | Without specific X designations, wherein X may be any amino acid |
| 14 | DX1VX2TQSPX3X4LAVSX5GEX6VTIX7CKX8SX9SX10X11X12X13X14HX15X16X17X18X19X20WYRQKPGQX21PKLLIYX22X23SX24X25X26SGVPX27RFX28GSGSGTDFTLTIX29X30VX31AX32DX33AX34YX35CX36QX37X38X39X40PX41TFGX42GTKLEX43KR wherein preferably X1: T or L; X2: L or M; X3: no AA or F; X4: A or S; X5: P or E; X6: R or M; X7: S or K; X8: A or S; X9: E or Q; X10: V or L; X11: S or L; X12: T or S; X13: R or S; X14: M or R; X15: no AA or Q; X16: no AA or K; X17: no AA or N; X18: no AA or F; X19: no AA or L; X20: no AA or A; X21: Q or S; X22: K or H; X23: T or A; X24: N or T; X25: L or R; X26: A or Q; X27: A or D; X28: S or I; X29: D or S; X30: P or D; X31: E or Q; X32: D or E; X33: T or L; X34: T or D; X35: F or Y; X36: Q or L; X37: S or H; X:38: W or Y; X39: N or T; X40: G or S; X41: L or Y; X42: S or A; X43: I or L (wherein "no AA" means "no amino acid") | Unitary VL 7A1 and 6G4 |
| 14 | DXVXTQSPXXLAVSXGEXVTIXCKXSXSXXXXXXHXXXXXXWYRQKPGQX21PKLLIYXXSXXXSGVPXRFXGSGSGTDFTLTIXXVXAXDXAXYXCXQXXXXPXTFGXGTKLEXKR | Without specific X designations, wherein X may be any amino acid |
| 15 | QVQLKESGPGLVQPSQTLSLTCTVSGLSLTSNGVSWIRQPPGKGLEWLGVIWSNGGTDYNSAIKSRLSFSRDTSKSQVFLKMNSLQTEDTAMYFCARPRYNSGYFFDYWGQGVMVTVSS | 7A1 VH |
| 16 | DTVLTQSPALAVSPGERVTISCKASESVSTRMHWYRQKPGQQPKLLIYKTSNLASGVPARFSGSGSGTDFTLTIDPVEADDTATYFCQQSWNGPLTFGSGTKLEIKR | 7A1 VL |
| 17 | QVQLKESGPGLVQPSQTLSLTCTVSGFSLTSYHVHWVRQPPGKGLEWMGVMWSDGDTLYNSALKSRLSISRDTSKSQVLLQMDSLQSEDTATYYCARLQVFGYPGIRDYVMDAWGQGASVTVSS | 6G4 VH |

| SEQ ID NO | Sequence | Description |
|---|---|---|
| 18 | DLVMTQSPFSLAVSEGEMVTIKCKSSQSLLSSRHQKNFLAWYRQK PGQSPKLLIYHASTRQSGVPDRFIGSGSGTDFTLTISDVQAEDLADY YCLQHYTSPYTFGAGTKLELKR | 6G4 VL |
| 19 | MEFGLSWLFLVAILKGVQC | IgHL leader |
| 20 | SGGGGSGGGGSGGGGS | G4S linker |
| 21 | ESKYGPPCPPCPGQPREPQVYTLPPSRDELTKNQVSLTCLVKGFY PSDIAVEWESNGQPENNYKTTPPVLDSDGSFFLYSKLTVDKSRWQ QGNVFSCSVMHEALHNHYTQKSLSLSPGKESKYGPPCPPCPGQP REPQVYTLPPSRDELTKNQVSLTCLVKGFYPSDIAVEWESNGQPE NNYKTTPPVLDSDGSFFLYSKLTVDKSRWQQGNVFSCSVMHEALH NHYTQKSLSLSPGK | IgG1 CH3 spacer |
| 22 | EPKSPDKTHTCPPCPAPELLGGPSVFLFPPKPKDTLMISRTPEVTC VVVDVSHEDPEVKFNWYVDGVEVHNAKTKPREEQYNSTYRVVSVL TVLHQDWLNGKEYKCKVSNKALPAPIEKTISKAKGQPREPQVYTLP PSRDELTKNQVSLTCLVKGFYPSDIAVEWESNGQPENNYKTTPPVL DSDGSFFLYSKLTVDKSRWQQGNVFSCSVMHEALHNHYTQKSLSL SPGK | IgG1 CH2 CH3 spacer |
| 23 | FWVLVVVGGVLACYSLLVTVAFIIFWVRS | CD28 transmembrane domain |
| 24 | VISTSGRPWPGLVGSFSCHWLSPFTATTG | CD8 alpha transmembrane domain |
| 25 | KRSRLLHSDYMNMTPRRPGPTRKHYQPYAPPRDFAAYRS | CD28 co-stimulatory domain |
| 26 | KRGRKKLLYIFKQPFMRPVQTTQEEDGCSCRFPEEEEGGCEL | 4-1BB co-stimulatory domain |
| 27 | RVKFSRSADAPAYQQGQNQLYNELNLGRREEYDVLDKRRGRDPE MGGKPRRKNPQEGLYNELQKDKMAEAYSEIGMKGERRRGKGHD GLYQGLSTATKDPTTPFTCRPCPL | CD3 zeta chain signaling domain |
| 28 | GDPA | Spacer |
| 29 | KDPK | Spacer |
| 30 | MEFGLSWLFLVAILKGVQCQVQLKESGPGLVQPSQTLSLTCTVSGL SLTSNGVSWIRQPPGKGLEWLGVIWSNGGTDYNSAIKSRLSFSRD TSKSQVFLKMNSLQTEDTAMYFCARPRYNSGYFFDYWGQGVMVT VSSSGGGGSGGGGSGGGGSDTVLTQSPALAVSPGERVTISCKAS ESVSTRMHWYRQKPGQQPKLLIYKTSNLASGVPARFSGSGSGTDF TLTIDPVEADDTATYFCQQSWNGPLTFGSGTKLEIKGDPAESKYGP PCPPCPGQPREPQVYTLPPSRDELTKNQVSLTCLVKGFYPSDIAVE WESNGQPENNYKTTPPVLDSDGSFFLYSKLTVDKSRWQQGNVFS CSVMHEALHNHYTQKSLSLSPGKKDPKFWVLVVVGGVLACYSLLV TVAFIIFWVRSKRSRLLHSDYMNMTPRRPGPTRKHYQPYAPPRDF AAYRSRVKFSRSADAPAYQQGQNQLYNELNLGRREEYDVLDKRR GRDPEMGGKPRRKNPQEGLYNELQKDKMAEAYSEIGMKGERRRG KGHDGLYQGLSTATKDTYDALHMQALPPR | 7A1 CAR.CD28.z |
| 31 | MEFGLSWLFLVAILKGVQCQVQLKESGPGLVQPSQTLSLTCTVSGF SLTSYHVHWVRQPPGKGLEWMGVMWSDGDTLYNSALKSRLSISR DTSKSQVLLQMDSLQSEDTATYYCARLQVFGYPGIRDYVMDAWG QGASVTVSSSGGGGSGGGGSGGGGSDLVMTQSPFSLAVSEGEM VTIKCKSSQSLLSSRHQKNFLAWYRQKPGQSPKLLIYHASTRQSGV PDRFIGSGSGTDFTLTISDVQAEDLADYYCLQHYTSPYTFGAGTKL ELKGDPAESKYGPPCPPCPGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGKKDPKFWVLV VVGGVLACYSLLVTVAFIIFWVRSKRSRLLHSDYMNMTPRRPGPTR KHYQPYAPPRDFAAYRSRVKFSRSADAPAYQQGQNQLYNELNLG RREEYDVLDKRRGRDPEMGGKPRRKNPQEGLYNELQKDKMAEAY SEIGMKGERRRGKGHDGLYQGLSTATKDPTTPFTCRPCPL | 6G4 CAR.CD28.z |

| SEQ ID NO | Sequence | Description |
|---|---|---|
| 32 | MEFGLSWLFLVAILKGVQCQVQLKESGPGLVQPSQTLSLTCTVSGL<br>SLTSNGVSWIRQPPGKGLEWLGVIWSNGGTDYNSAIKSRLSFSRD<br>TSKSQVFLKMNSLQTEDTAMYFCARPRYNSGYFFDYWGQGVMVT<br>VSSSGGGGSGGGGSGGGGSDTVLTQSPALAVSPGERVTISCKAS<br>ESVSTRMHWYRQKPGQQPKLLIYKTSNLASGVPARFSGSGSGTDF<br>TLTIDPVEADDTATYFCQQSWNGPLTFGSGTKLEIKGDPAEPKSPD<br>KTHTCPPCPAPELLGGPSVFLFPPKPKDTLMISRTPEVTCVVVDVS<br>HEDPEVKFNWYVDGVEVHNAKTKPREEQYNSTYRVVSVLTVLHQD<br>WLNGKEYKCKVSNKALPAPIEKTISKAKGQPREPQVYTLPPSRDEL<br>TKNQVSLTCLVKGFYPSDIAVEWESNGQPENNYKTTPPVLDSDGS<br>FFLYSKLTVDKSRWQQGNVFSCSVMHEALHNHYTQKSLSLSPGKK<br>DPKFWVISTSGRPWPGLVGSFSCHWLSPFTATTGKRGRKKLLYIFK<br>QPFMRPVQTTQEEDGCSCRFPEEEEGGCELRVKFSRSADAPAYQ<br>QGQNQLYNELNLGRREEYDVLDKRRGRDPEMGGKPRRKNPQEG<br>LYNELQKDKMAEAYSEIGMKGERRRGKGHDGLYQGLSTATKDTYD<br>ALHMQALPPR | 7A1 CAR.41BB.z |
| 33 | MEFGLSWLFLVAILKGVQCQVQLKESGPGLVQPSQTLSLTCTVSGF<br>SLTSYHVHWVRQPPGKGLEWMGVMWSDGDTLYNSALKSRLSISR<br>DTSKSQVLLQMDSLQSEDTATYYCARLQVFGYPGIRDYVMDAWG<br>QGASVTVSSSGGGGSGGGGSGGGGSDLVMTQSPFSLAVSEGEM<br>VTIKCKSSQSLLSSRHQKNFLAWYRQKPGQSPKLLIYHASTRQSGV<br>PDRFIGSGSGTDFTLTISDVQAEDLADYYCLQHYTSPYTFGAGTKL<br>ELKGDPAEPKSPDKTHTCPPCPAPELLGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPAPIEKTISKAKGQPR<br>EPQVYTLPPSRDELTKNQVSLTCLVKGFYPSDIAVEWESNGQPEN<br>NYKTTPPVLDSDGSFFLYSKLTVDKSRWQQGNVFSCSVMHEALHN<br>HYTQKSLSLSPGKKDPKFWVISTSGRPWPGLVGSFSCHWLSPFTA<br>TTGKRGRKKLLYIFKQPFMRPVQTTQEEDGCSCRFPEEEEGGCER<br>VKFSRSADAPAYQQGQNQLYNELNLGRREEYDVLDKRRGRDPEM<br>GGKPRRKNPQEGLYNELQKDKMAEAYSEIGMKGERRRGKGHDGL<br>Y | 6G4 CAR.41BB.z |
| 34 | ATGGAGTTTGGCCTGAGCTGGCTGTTTCTGGTGGCCATTCTGAA<br>GGGCGTGCAGTGCCAGGTGCAGCTGAAAGAATCTGGACCTGGC<br>CTGGTGCAGCCTAGCCAGACACTGTCTCTGACATGTACAGTGTC<br>CGGCCTGAGCCTGACAAGCAACGGCGTTAGCTGGATCAGACAG<br>CCTCCTGGCAAAGGCCTGGAATGGCTGGGCGTTATCTGGTCCA<br>ATGGCGGCACCGACTACAACAGCGCCATCAAGAGCAGACTGAG<br>CTTCAGCAGAGACACCAGCAAGAGCCAGGTGTTCCTGAAGATG<br>AACAGCCTGCAGACCGAGGACACCGCCATGTACTTTTGCGCCA<br>GACCTCGGTACAACTCCGGCTACTTCTTCGATTATTGGGGCCAG<br>GGCGTGATGGTCACAGTGTCATCTAGCGGAGGCGGAGGAAGTG<br>GTGGCGGAGGTTCTGGCGGCGGAGGATCTGATACAGTGCTGAC<br>ACAAAGCCCCGCTCTGGCTGTGTCTCCTGGCGAGAGAGTGACA<br>ATCAGCTGCAAGGCCAGCGAGAGCGTGTCCACCAGAATGCACT<br>GGTACAGACAGAAGCCCGGCCAGCAGCCAAAGCTGCTGATCTA<br>CAAGACCAGCAATCTGGCCAGCGGCGTGCCAGCCAGATTTTCT<br>GGTTCTGGCTCTGGCACCGATTTCACCCTGACCATCGATCCCGT<br>GGAAGCCGACGATACCGCCACCTACTTTTGTCAGCAGAGCTGG<br>AACGGCCCTCTGACCTTTGGCAGCGGCACCAAGCTGGAAATCA<br>AAGGGGATCCCGCCGAGTCTAAATATGGCCCACCTTGCCCCACC<br>GTGCCCAGGGCAGCCCCGAGAACCACAGGTGTACACCCTGCCC<br>CCATCCCGGGATGAGCTGACCAAGAACCAGGTCAGCCTGACCT<br>GCCTGGTCAAAGGCTTCTATCCCAGCGACATCGCCGTGGAGTG<br>GGAGAGCAATGGGCAACCGGAGAACAACTACAAGACCACGCCT<br>CCCGTGCTGGACTCCGACGGCTCCTTCTTCCTCTACAGCAAGCT<br>CACCGTGGACAAGAGCAGGTGGCAGCAGGGGAACGTCTTCTCA<br>TGCTCCGTGATGCATGAGGCTCTGCACAACCACTACACGCAGAA<br>GAGCCTCTCCCTGTCTCCGGGTAAAAAAGATCCCAAATTTTGGG<br>TGCTGGTGGTGGTTGGTGGAGTCCTGGCTTGCTATAGCTTGCTA<br>GTAACAGTGGCCTTTATTATTTTCTGGGTGAGGAGTAAGAGGAG<br>CAGGCTCCTGCACAGTGACTACATGAACATGACTCCCCGCCGC<br>CCCGGGCCCACCCGCAAGCATTACCAGCCCTATGCCCCACCAC<br>GCGACTTCGCAGCCTATCGCTCCAGAGTGAAGTTCAGCAGGAG<br>CGCAGACGCCCCCGCGTACCAGCAGGGCCAGAACCAGCTCTAT<br>AACGAGCTCAATCTAGGACGAAGAGAGGAGTACGATGTTTTGGA<br>CAAGAGACGTGGCCGGGACCCTGAGATGGGGGGAAAGCCGAG<br>AAGGAAGAACCCTCAGGAAGGCCTGTACAATGAACTGCAGAAA<br>GATAAGATGGCGGAGGCCTACAGTGAGATTGGGATGAAAGGCG<br>AGCGCCGGAGGGGCAAGGGGCACGATGGCCTTTACCAGGGTC<br>TCAGTACAGCCACCAAGGACACCTACGACGCCCTTCACATGCA<br>GGCCCTGCCCCCTCGC | 7A1 CAR.CD28.z;<br>encodes SEQ ID<br>NO: 30 |

| SEQ ID NO | Sequence | Description |
|---|---|---|
| 35 | ATGGAGTTTGGCCTGAGCTGGCTGTTTCTGGTGGCCATTCTGAA<br>GGGCGTGCAGTGCCAGGTGCAGCTGAAAGAATCTGGACCTGGC<br>CTGGTGCAGCCTAGCCAGACACTGTCTCTGACATGCACCGTGT<br>CCGGCTTCAGCCTGACAAGCTACCATGTGCACTGGGTCCGACA<br>GCCACCTGGCAAAGGACTGGAATGGATGGGCGTTATGTGGTCC<br>GACGGCGACACACTGTACAACAGCGCCCTGAAGTCCCGGCTGA<br>GCATCAGCAGAGATACCAGCAAGTCTCAGGTGCTGCTGCAGAT<br>GGATAGCCTGCAGAGCGAGGATACCGCCACCTACTATTGTGCC<br>AGACTCCAGGTGTTCGGCTACCCCGGCATCAGAGATTACGTGAT<br>GGATGCTTGGGGACAGGGCGCCTCTGTGACAGTTTCTTCTAGC<br>GGAGGCGGAGGAAGTGGTGGCGGAGGTTCTGGCGGCGGAGGA<br>TCTGATCTGGTTATGACACAGAGCCCTTTCAGCCTGGCCGTGTC<br>TGAGGGCGAGATGGTCACAATCAAGTGCAAGAGCAGCCAGAGC<br>CTGCTGAGCAGCCGGCACCAGAAAAACTTTCTGGCTTGGTACA<br>GACAGAAGCCCGGACAGAGCCCCAAGCTGCTGATCTACCATGC<br>CAGCACAAGACAGAGCGGCGTGCCCGATAGATTCATCGGATCT<br>GGCAGCGGCACCGACTTCACACTGACAATTTCTGATGTGCAGG<br>CCGAGGATCTGGCCGACTACTACTGTCTGCAGCACTACACAAG<br>CCCCTACACCTTCGGAGCCGGCACAAAGCTGGAACTGAAAGGG<br>GATCCCGCCGAGTCTAAATATGGCCCACCTTGCCCACCGTGCC<br>CAGGGCAGCCCCGAGAACACAGGTGTACACCCTGCCCCCATC<br>CCGGGATGAGCTGACCAAGAACCAGGTCAGCCTGACCTGCCTG<br>GTCAAAGGCTTCTATCCCAGCGACATCGCCGTGGAGTGGGAGA<br>GCAATGGGCAACCGGAGAACAACTACAAGACCACGCCTCCCGT<br>GCTGGACTCCGACGGCTCCTTCTTCCTCTACAGCAAGCTCACCG<br>TGGACAAGAGCAGGTGGCAGCAGGGGAACGTCTTCTCATGCTC<br>CGTGATGCATGAGGCTCTGCACAACCACTACACGCAGAAGAGC<br>CTCTCCCTGTCTCCGGGTAAAAAAGATCCCAAATTTTGGGTGCT<br>GGTGGTGGTTGGTGGAGTCCTGGCTTGCTATAGCTTGCTAGTAA<br>CAGTGGCCTTTATTATTTTCTGGGTGAGGAGTAAGAGGAGCAGG<br>CTCCTGCACAGTGACTACATGAACATGACTCCCCGCCGCCCCG<br>GGCCCACCCGCAAGCATTACCAGCCCTATGCCCCACCACGCGA<br>CTTCGCAGCCTATCGCTCCAGAGTGAAGTTCAGCAGGAGCGCA<br>GACGCCCCGCGTACCAGCAGGGCCAGAACCAGCTCTATAACG<br>AGCTCAATCTAGGACGAAGAGAGGAGTACGATGTTTTGGACAAG<br>AGACGTGGCCGGGACCCTGAGATGGGGGGAAAGCCGAGAAGG<br>AAGAACCCTCAGGAAGGCCTGTACAATGAACTGCAGAAAGATAA<br>GATGGCGGAGGCCTACAGTGAGATTGGGATGAAAGGCGAGCG<br>CCGGAGGGGCAAGGGCACGATGGCCTTTACCAGGGTCTCAGT<br>ACAGCCACCAAGGACACCTACGACGCCCTTCACATGCAGGCCC<br>TGCCCCCTCGC | 6G4 CAR.CD28.z; encodes SEQ ID NO: 31 |
| 36 | ATGGAGTTTGGCCTGAGCTGGCTGTTTCTGGTGGCCATTCTGAA<br>GGGCGTGCAGTGCCAGGTGCAGCTGAAAGAATCTGGACCTGGC<br>CTGGTGCAGCCTAGCCAGACACTGTCTCTGACATGTACAGTGTC<br>CGGCCTGAGCCTGACAAGCAACGGCGTTAGCTGGATCAGACAG<br>CCTCCTGGCAAAGGCCTGGAATGGCTGGGCGTTATCTGGTCCA<br>ATGGCGGCACCGACTACAACAGCGCCATCAAGAGCAGACTGAG<br>CTTCAGCAGAGACACCAGCAAGAGCCAGGTGTTCCTGAAGATG<br>AACAGCCTGCAGACCGAGGACACCGCCATGTACTTTTGCGCCA<br>GACCTCGGTACAACTCCGGCTACTTCTTCGATTATTGGGGCCAG<br>GGCGTGATGGTCACAGTGTCATCGGAGGCGGAGGAAGTG<br>GTGGCGGAGGTTCTGGCGGCGGAGGATCTGATACAGTGCTGAC<br>ACAAAGCCCCGCTCTGGCTGTGTCTCCTGGCGAGAGAGTGACA<br>ATCAGCTGCAAGGCCAGCGAGAGCGTGTCCACCAGAATGCACT<br>GGTACAGACAGAAGCCCGGCCAGCAGCCAAAGCTGCTGATCTA<br>CAAGACCAGCAATCTGGCCAGCGGCGTGCCAGCCAGATTTTCT<br>GGTTCTGGCTCTGGCACCGATTTCACCCTGACCATCGATCCCGT<br>GGAAGCCGACGATACCGCCACCTACTTTTGTCAGCAGAGCTGG<br>AACGGCCCTCTGACCTTTGGCAGCGGCACCAAGCTGGAAATCA<br>AAGGGGATCCCGCCGAGCCCAAATCCTGACAAAACTCACAC<br>ATGCCCACCGTGCCCAGCACCTGAACTCCTGGGGGGACCGTCA<br>GTCTTCCTCTTCCCCCCAAAACCCAAGGACACCCTCATGATCTC<br>CCGGACCCCTGAGGTCACATGCGTGGTGGTGGACGTGAGCCAC<br>GAAGACCCTGAGGTCAAGTTCAACTGGTACGTGGACGGCGTGG<br>AGGTGCATAATGCCAAGACAAAGCCGCGGGAGGAGCAGTACAA<br>CAGCACGTACCGTGTGGTCAGCGTCCTCACCGTCCTGCACCAG<br>GACTGGCTGAATGGCAAGGAGTACAAGTGCAAGGTCTCCAACA<br>AAGCCCTCCCAGCCCCCATCGAGAAAACCATCTCCAAAGCCAAA<br>GGGCAGCCCCGAGAACCACAGGTGTACACCCTGCCCCCATCCC<br>GGGATGAGCTGACCAAGAACCAGGTCAGCCTGACCTGCCTGGT<br>CAAAGGCTTCTATCCCAGCGACATCGCCGTGGAGTGGGAGAGC<br>AATGGGCAACCGGAGAACAACTACAAGACCACGCCTCCCGTGC<br>TGGACTCCGACGGCTCCTTCTTCCTCTACAGCAAGCTCACCGTG | 7A1 CAR.41BB.z; encodes SEQ ID NO: 32 |

| SEQ ID NO | Sequence | Description |
|---|---|---|
| | GACAAGAGCAGGTGGCAGCAGGGGAACGTCTTCTCATGCTCCG<br>TGATGCATGAGGCTCTGCACAACCACTACACGCAGAAGAGCCT<br>CTCCCTGTCTCCGGGTAAAAAAGATCCCAAATTTTGGTGTGATAT<br>CTACATCTGGGCGCCCTTGGCCGGGACTTGTGGGGTCCTTCTC<br>CTGTCACTGGTTATCACCCTTTACTGCAACCACAGGAACAAACG<br>GGGCAGAAAGAAACTCCTGTATATATTCAAACAACCATTTATGAG<br>ACCAGTACAAACTACTCAAGAGGAAGATGGCTGTAGCTGCCGAT<br>TTCCAGAAGAAGAAGAAGGAGGATGTGAACTGAGAGTGAAGTTC<br>AGCAGGAGCGCAGACGCCCCCGCGTACCAGCAGGGCCAGAAC<br>CAGCTCTATAACGAGCTCAATCTAGGACGAAGAGAGGAGTACGA<br>TGTTTTGGACAAGAGACGTGGCCGGGACCCTGAGATGGGGGGA<br>AAGCCGAGAAGGAAGAACCCTCAGGAAGGCCTGTACAATGAAC<br>TGCAGAAAGATAAGATGGCGGAGGCCTACAGTGAGATTGGGAT<br>GAAAGGCGAGCGCCGGAGGGGCAAGGGGCACGATGGCCTTTA<br>CCAGGGTCTCAGTACAGCCACCAAGGACACCTACGACGCCCTT<br>CACATGCAGGCCCTGCCCCCTCGC | |
| 37 | ATGGAGTTTGGCCTGAGCTGGCTGTTTCTGGTGGCCATTCTGAA<br>GGGCGTGCAGTGCCAGGTGCAGCTGAAAGAATCTGGACCTGGC<br>CTGGTGCAGCCTAGCCAGACACTGTCTCTGACATGCACCGTGT<br>CCGGCTTCAGCCTGACAAGCTACCATGTGCACTGGGTCCGACA<br>GCCACCTGGCAAAGGACTGGAATGGATGGGCGTTATGGTGTCC<br>GACGGCGACACACTGTACAACAGCGCCCTGAAGTCCCGGCTGA<br>GCATCAGCAGAGATACCAGCAAGTCTCAGGTGCTGCTGCAGAT<br>GGATAGCCTGCAGAGCGAGGATACCGCCACCTACTATTGTGCC<br>AGACTCCAGGTGTTCGGCTACCCCGGCATCAGAGATTACGTGAT<br>GGATGCTTGGGGACAGGGCGCCTCTGTGACAGTTTCTTCTAGC<br>GGAGGCGGAGGAAGTGGTGGCGGAGGTTCTGGCGGCGGAGGA<br>TCTGATCTGGTTATGACACAGAGCCCTTTCAGCCTGGCCGTGTC<br>TGAGGGCGAGATGGTCACAATCAAGTGCAAGAGCAGCCAGAGC<br>CTGCTGAGCAGCCGGCACCAGAAAAAACTTTCTGGCTTGGTACA<br>GACAGAAGCCCGGACAGAGCCCCAAGCTGCTGATCTACCATGC<br>CAGCACAAGACAGAGCGGCGTGCCCGATAGATTCATCGGATCT<br>GGCAGCGGCACCGACTTCACACTGACAATTTCTGATGTGCAGG<br>CCGAGGATCTGGCCGACTACTACTGTCTGCAGCACTACACAAG<br>CCCCTACACCTTCGGAGCGGCACAAAGCTGGAACTGAAAGGG<br>GATCCCGCCGAGCCCAAATCCTGACAAAACTCACACATGCCC<br>ACCGTGCCCAGCACCTGAACTCCTGGGGGGACCGTCAGTCTTC<br>CTCTTCCCCCCAAAACCCAAGGACACCCTCATGATCTCCCGGAC<br>CCCTGAGGTCACATGCGTGGTGGTGGACGTGAGCCACGAAGAC<br>CCTGAGGTCAAGTTCAACTGGTACGTGGACGGCGTGGAGGTGC<br>ATAATGCCAAGACAAAGCCGCGGGAGGAGCAGTACAACAGCAC<br>GTACCGTGTGGTCAGCGTCCTCACCGTCCTGCACCAGGACTGG<br>CTGAATGGCAAGGAGTACAAGTGCAAGGTCTCCAACAAAGCCCT<br>CCCAGCCCCCATCGAGAAAACCATCTCCAAAGCCAAAGGGCAG<br>CCCCGAGAACCACAGGTGTACACCCTGCCCCCATCCCGGGATG<br>AGCTGACCAAGAACCAGGTCAGCCTGACCTGCCTGGTCAAAGG<br>CTTCTATCCCAGCGACATCGCCGTGGAGTGGGAGAGCAATGGG<br>CAACCGGAGAACAACTACAAGACCACGCCTCCCGTGCTGGACT<br>CCGACGGCTCCTTCTTCCTCTACAGCAAGCTCACCGTGGACAAG<br>AGCAGGTGGCAGCAGGGGAACGTCTTCTCATGCTCCGTGATGC<br>ATGAGGCTCTGCACAACCACTACACGCAGAAGAGCCTCTCCCT<br>GTCTCCGGGTAAAAAAGATCCCAAATTTTGGTGTGATATCTACAT<br>CTGGGCGCCCTTGGCCGGGACTTGTGGGGTCCTTCTCCTGTCA<br>CTGGTTATCACCCTTTACTGCAACCACAGGAACAAACGGGGCAG<br>AAAGAAACTCCTGTATATATTCAAACAACCATTTATGAGACCAGT<br>ACAAACTACTCAAGAGGAAGATGGCTGTAGCTGCCGATTTCCAG<br>AAGAAGAAGGAGGATGTGAACTGAGAGTGAAGTTCAGCAG<br>GAGCGCAGACGCCCCCGCGTACCAGCAGGGCCAGAACCAGCT<br>CTATAACGAGCTCAATCTAGGACGAAGAGAGGAGTACGATGTTT<br>TGGACAAGAGACGTGGCCGGGACCCTGAGATGGGGGAAAGC<br>CGAGAAGGAAGAACCCTCAGGAAGGCCTGTACAATGAACTGCA<br>GAAAGATAAGATGGCGGAGGCCTACAGTGAGATTGGGATGAAA<br>GGCGAGCGCCGGAGGGGCAAGGGGCACGATGGCCTTTACCAG<br>GGTCTCAGTACAGCCACCAAGGACACCTACGACGCCCTTCACAT<br>GCAGGCCCTGCCCCCTCGC | 6G4 CAR.41BB.z;<br>encodes SEQ ID<br>NO: 33 |

According to the invention, the embodiments of any given aspect are considered to apply to other aspects and embodiments, such that combinations of particular embodiments as disclosed herein are contemplated. For example, embodiments disclosed with respect to the medical treatment may be incorporated as functional features of the CARs, and vice versa.

DETAILED DESCRIPTION OF THE INVENTION

All cited documents of the patent and non-patent literature are hereby incorporated by reference in their entirety.

Herpes Virus

There are multiple herpesvirus types known to infect humans, those of primary relevance being herpes simplex viruses 1 and 2 (HSV-1 and HSV-2, also known as HHV1 and HHV2), varicella-zoster virus (VZV, also known as HHV-3), Epstein-Barr virus (EBV or HHV-4), human cytomegalovirus (HCMV or HHV-5), human herpesvirus 6A and 6B (HHV-6A and HHV-6B), human herpesvirus 7 (HHV-7), and Kaposi's sarcoma-associated herpesvirus (KSHV, also known as HHV-8). Herpes viruses share a common structure, being composed of relatively large double-stranded, linear DNA genomes encoding 100-200 genes encased within an icosahedral protein cage called the capsid, which is itself wrapped in a protein layer called the tegument, containing both viral proteins and viral mRNAs and a lipid bilayer membrane called the envelope. Infection is initiated when a viral particle contacts a cell with specific types of receptor molecules on the cell surface, for example CD21.

Following binding of viral envelope glycoproteins to cell membrane receptors, the virion is internalized and dismantled, allowing viral DNA to migrate to the cell nucleus. Within the nucleus, replication of viral DNA and transcription of viral genes occurs. During symptomatic infection, infected cells transcribe lytic viral genes. In some host cells, a small number of viral genes termed latency associated transcript (LAT) accumulate instead. In this fashion the virus can persist in the cell (and thus the host) indefinitely. While primary infection is often accompanied by a self-limited period of clinical illness, long-term latency is typically symptom-free. Reactivation of latent viruses has been implicated in a number of diseases. Following activation, transcription of viral genes transitions from LAT to multiple lytic genes; these lead to enhanced replication and virus production. Often, lytic activation leads to cell death. Clinically, lytic activation is often accompanied by emergence of non-specific symptoms such as low-grade fever, headache, sore throat, malaise, and rash as well as clinical signs such as swollen or tender lymph nodes and immunological findings.

EBV is a human herpesvirus that is carried by almost all of the adult population of the world. Many primary infections occur in childhood and are asymptomatic. Those occurring after the age of about 12- or 13-year-old are more likely to be accompanied by infectious mononucleosis, a self-limiting, but temporarily debilitating immunopathology. Regardless of whether or not infection is accompanied by disease, the virus persists. It establishes latency in long-lived memory B cells and reactivates sporadically to be amplified in epithelial cells, shed in saliva for oral transmission to a new host or returned to B cells to replenish the B-cell reservoir. The vast majority of people suffer no ill effects from persistence of EBV, but the virus is nevertheless associated, and probably causally associated, with a number of B cell and epithelial cell malignancies, including Burkitt and Hodgkin lymphoma, post-transplant lymphoproliferative disorders and immunoblastic lymphomas of the immunosuppressed, anaplastic nasopharyngeal carcinomas and a subset of gastric carcinomas. It is also linked with autoimmune diseases such as multiple sclerosis (Hutt-Fletcher, 2015).

Glycoproteins play an important role in virus particle formation and infection of host cells. The most abundant of the virion glycoproteins is gp350, which was identified as the protein responsible for attachment of virus to B lymphocytes. It is a 907-residue, type 1 membrane protein found in the virion as two splice variants, which, when fully glycosylated, have masses of approximately 350 and 220 kDa.

The splice maintains the reading frame and both forms of the protein retain the N-terminal attachment site, a glycan-free surface, which tethers the virus to CR2/CD21. Whether there is any functional significance to the maintenance of the splice variants is not clear. However, since both CR2 and gp350 have been modeled as extended proteins that initially position the virus at some distance from the cell surface, perhaps sequential binding to gp350 and gp220 is relevant to bringing the virus closer to the cell membrane.

Any references herein to gp350 relate therefore to gp350 or gp220, or vice versa. The antigen binding fragments disclosed herein bind to gp350 and/or gp220.

Following attachment to the B-cell surface, EBV, as an enveloped virus, enters the cell via fusion of its envelope with the cell membrane. Fusion, which occurs from within an endocytic vesicle, requires the action of four additional glycoproteins, gB, gH, gL and gp42 (Hutt-Fletcher, 2015). Glycoprotein B is a type I membrane protein expressed as a homotrimer. In all herpesviruses, gB is now generally agreed to be the final executor of fusion. Glycoproteins gH, gL and gp42 are viewed as being regulators of the process. Glycoprotein gp42 can be found in cells as a type 2 membrane protein, or as a soluble protein from which the signal sequence is cleaved. It interacts with gH, via a flexible segment in its N-terminal domain and with HLA class II, via a C-type lectin domain at its C-terminus.

EBV Associated Disease

The invention further relates to the treatment of herpes virus associated disease, preferably EBV associated disease. For example, such medical conditions encompass herpes virus-associated cancers or chronic active herpes virus infections or primary herpes virus infections.

Of particular relevance is the treatment of lymphoproliferative disorders (LPD), such as B-cell lymphoma, including Burkitt lymphoma (BL), Hodgkin lymphoma (HL), a diffuse large B cell lymphoma (DLBCL) using the CARs and immune cells described herein.

The B-cell lymphomas are types of lymphoma affecting B cells. Lymphomas are typically referred to as "blood cancers" in the lymph nodes. They develop more frequently in older adults and in immunocompromised individuals. B-cell lymphomas include both Hodgkin's lymphomas and most non-Hodgkin lymphomas.

DLBCL is a cancer of B cells. Typically, DLBCL arises from normal B cells, but it can also represent a malignant transformation of other types of lymphoma or leukemia. An underlying immunodeficiency is a significant risk factor and infection with Epstein-Barr virus has also been found to contribute to the development of DLBCL.

Burkitt lymphoma is a cancer of the lymphatic system, particularly B lymphocytes found in the germinal center. Burkitt lymphoma can be divided into three main clinical variants: the endemic, the sporadic, and the immunodeficiency-associated variants. EBV infection is found in nearly all endemic variants.

Also relevant is the treatment of a post-transplant lymphoproliferative disorder (PTLD), an epithelial carcinoma (nasopharyngeal, lung, breast), a lymphoepithelioma, a carcinoma with lymphoid stroma (GCLS, e.g. gastric carcinoma) or a glioma using the CARs and immune cells described herein.

PTLD is the name given to a B-cell proliferation due to therapeutic immunosuppression after organ transplantation. These patients may develop infectious mononucleosis-like lesions or polyclonal polymorphic B-cell hyperplasia. The invention therefore also relates to the treatment of immune deficient or immune compromised patients after chemotherapy, radiation, immune suppression or transplantation.

Nasopharynx cancer or nasopharyngeal carcinoma (NPC) is the most common cancer originating in the nasopharynx, most commonly in the postero-lateral nasopharynx or pharyngeal recess, accounting for 50% cases. NPC occurs in children and adults. The association between Epstein-Barr virus and nasopharyngeal carcinoma is unequivocal in World Health Organization (WHO) types II and III tumors. Lymphoepithelioma is a type of poorly differentiated nasopharyngeal carcinoma characterized by prominent infiltration of lymphocytes in the area involved by tumor. Lymphoepithelioma is also known as "class III nasopharyngeal carcinoma" in the WHO classification system.

Gastric carcinoma with lymphoid stroma (GCLS) is a distinct histologic subtype of gastric cancer that is characterized by undifferentiated carcinoma mixed with prominent lymphoid infiltration. More than 80% of GCLS cases are associated with EBV infection, but it is unclear if the virus affects disease progression.

A glioma is a type of tumor that starts in the glial cells of the brain or the spine. Gliomas comprise about 30 percent of all brain tumors and central nervous system tumors, and 80 percent of all malignant brain tumors. Studies have revealed that EBV is present in elevated frequencies in glioma patients, indicating potential targeting of EBV associated glioma using the present invention.

In further aspects of the invention, the medical condition associated with EBV infection to be treated is chronic active EBV infection (CAEBV) or primary EBV infection (e.g. mononucleosis).

CAEBV is a rare and often fatal complication of EBV infection that most often occurs in children or adolescents of Asian or South American lineage, although cases in Hispanics, Europeans and Africans have been reported. At present, the only known cure for CAEBV is allogenic haematopoietic stem cell transplant (HSCT), with all other treatment options (rituximab, cytotoxic chemotherapy and immunosuppressive therapy) appearing ultimately ineffective.

Infectious mononucleosis, also known as glandular fever, is an infection commonly caused by EBV. Most people are infected by the virus as children, when the disease produces little or no symptoms. In young adults, the disease often results in fever, sore throat, enlarged lymph nodes in the neck, and tiredness.

Chimeric Antigen Receptors:

According to the present invention, a CAR polypeptide comprises an extracellular antigen-binding domain, comprising an antibody or antibody fragment that binds a target antigen, a transmembrane domain, and an intracellular domain. CARs are typically described as comprising an extracellular ectodomain (antigen-binding domain) derived from an antibody and an endodomain comprising signaling modules derived from T cell signaling proteins.

In a preferred embodiment, the ectodomain preferably comprises variable regions from the heavy and light chains of an immunoglobulin configured as a single-chain variable fragment (scFv). The scFv is preferably attached to a hinge region that provides flexibility and transduces signals through an anchoring transmembrane moiety to an intracellular signaling domain. The transmembrane domains originate preferably from either CD8α or CD28. In the first generation of CARs the signaling domain consists of the zeta chain of the TCR complex. The term "generation" refers to the structure of the intracellular signaling domains. Second generation CARs are equipped with a single costimulatory domain originated from CD28 or 4-1BB. Third generation CARs already include two costimulatory domains, e.g. CD28, 4-1BB, ICOS or OX40, CD3 zeta. The present invention preferably relates to a second or third generation CAR, although the antigen binding fragments described herein may be employed in any given CAR format.

In various embodiments, genetically engineered receptors that redirect cytotoxicity of immune effector cells toward B cells are provided. These genetically engineered receptors referred to herein as CARs. CARs are molecules that combine antibody-based specificity for a desired antigen (e.g. gp350/gp220) with a T cell receptor-activating intracellular domain to generate a chimeric protein that exhibits a specific (e.g. anti-gp350/gp220) cellular immune activity. As used herein, the term, "chimeric," describes being composed of parts of different proteins or DNAs from different origins.

CARs contemplated herein, comprise an extracellular domain (also referred to as a binding domain or antigen-binding domain) that binds to a herpes viral antigen, preferably gp350/gp220, a transmembrane domain, and an intracellular domain, or intracellular signaling domain. Engagement of the antigen binding domain of the CAR with the target on the surface of a target cell results in clustering of the CAR and delivers an activation stimulus to the CAR-containing cell. The main characteristic of CARs are their ability to redirect immune effector cell specificity, thereby triggering the proliferation of antigen-specific effector T cells, cytokine production (such as IFN-γ), and production of molecules that can mediate death of the target cells expressing the surface antigen in a major histocompatibility complex (MHC) independent manner.

In various embodiments, a CAR comprises an extracellular binding domain that comprises a (optionally humanized) gp350/gp220-specific binding domain; a transmembrane domain; one or more intracellular signaling domains. In particular embodiments, a CAR comprises an extracellular binding domain that comprises a (optionally humanized) anti-gp350/gp220 antigen binding fragment thereof; one or more spacer domains; a transmembrane domain; one or more intracellular signaling domains.

The "extracellular antigen-binding domain" or "extracellular binding domain" are used interchangeably and provide a CAR with the ability to specifically bind to the target antigen of interest. The binding domain may be derived either from a natural, synthetic, semi-synthetic, or recombinant source. Preferred are scFv domains.

"Specific binding" is to be understood as via one skilled in the art, whereby the skilled person is clearly aware of various experimental procedures that can be used to test binding and binding specificity. Methods for determining equilibrium association or equilibrium dissociation constants are known in the art. Some cross-reaction or background binding may be inevitable in many protein-protein interactions; this is not to detract from the "specificity" of the binding between CAR and epitope. "Specific binding" describes binding of an anti-herpes virus antigen antibody or antigen binding fragment thereof (or a CAR comprising the same) to said herpes virus antigen at greater binding affinity than background binding. The term "directed against" is also applicable when considering the term "specificity" in understanding the interaction between antibody and epitope.

An "antigen (Ag)" refers to a compound, composition, or substance that can stimulate the production of antibodies or a T cell response in an animal. In particular embodiments, the target antigen is an epitope of an EBV gp350 and/or gp220 polypeptide. An "epitope" refers to the region of an antigen to which a binding agent binds. Epitopes can be formed both from contiguous amino acids or noncontiguous amino acids juxtaposed by tertiary folding of a protein.

"Single-chain Fv" or "scFv" antibody fragments comprise the VH and VL domains of an antibody, wherein these domains are present in a single polypeptide chain and in either orientation {e.g., VL-VH or VH-VL). Generally, the scFv polypeptide further comprises a polypeptide linker between the VH and VL domains which enables the scFv to form the desired structure for antigen binding. In preferred embodiments, a CAR contemplated herein comprises antigen-specific binding domain that is an scFv and may be a murine, human or humanized scFv. Single chain antibodies may be cloned form the V region genes of a hybridoma specific for a desired target. In particular embodiments, the antigen-specific binding domain is a humanized scFv that binds EBV gp350 and/or gp220 polypeptide.

An illustrative example of a variable heavy chain that is suitable for constructing anti-gp350/gp220 CARs contemplated herein include, but are not limited to the amino acid sequence set forth in SEQ ID NOs 15 or 17. An illustrative example of a variable light chain that is suitable for constructing anti-gp350/gp220 CARs contemplated herein include, but are not limited to the amino acid sequence set forth in SEQ ID NOs 16 or 18.

Antibodies and Antibody Fragments:

The CAR comprises an extracellular antigen-binding domain, comprising an antibody or antibody fragment that binds a target polypeptide as described herein. Antibodies or antibody fragments of the invention therefore include, but are not limited to polyclonal, monoclonal, bispecific, human, humanized or chimeric antibodies, single chain fragments (scFv), single variable fragments (ssFv), single domain antibodies (such as VHH fragments from nanobodies), Fab fragments, F(ab')2 fragments, fragments produced by a Fab expression library, anti-idiotypic antibodies and epitope-binding fragments or combinations thereof of any of the above, provided that they retain similar binding properties of the CAR described herein, preferably comprising the corresponding CDRs, or VH and VL regions as described herein. Also mini-antibodies and multivalent antibodies such as diabodies, triabodies, tetravalent antibodies and peptabodies can be used in a method of the invention. The immunoglobulin molecules of the invention can be of any class (i.e. IgG, IgE, IgM, IgD and IgA) or subclass of immunoglobulin molecules. Thus, the term antibody, as used herein, also includes antibodies and antibody fragments comprised by the CAR of the invention, either produced by the modification of whole antibodies or synthesized de novo using recombinant DNA methodologies.

As used herein, an "antibody" generally refers to a protein consisting of one or more polypeptides substantially encoded by immunoglobulin genes or fragments of immunoglobulin genes. Where the term "antibody" is used, the term "antibody fragment" may also be considered to be referred to. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (L) (about 25 kD) and one "heavy" (H) chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively. Optionally, the antibody or the immunological portion of the antibody, can be chemically conjugated to, or expressed as, a fusion protein with other proteins.

The CARs of the invention are intended to bind against mammalian, in particular human, protein targets. The use of protein names may correspond to either mouse or human versions of a protein.

Affinities of binding domain polypeptides and CAR proteins according to the present disclosure can be readily determined using conventional techniques, e.g., by competitive ELISA (enzyme-linked immunosorbent assay), or by binding association, or displacement assays using labeled ligands, or using a surface-plasmon resonance device such as the Biacore.

Humanized antibodies comprising one or more CDRs of antibodies of the invention or one or more CDRs derived from said antibodies can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807, 715; 5,866,692; 6,331,415; 5,530,101; 5,693,761; 5,693, 762; 5,585,089; 6,180,370; 5,225,539; 6,548,640.

The term humanized antibody means that at least a portion of the framework regions, and optionally a portion of CDR regions or other regions involved in binding, of an immunoglobulin is derived from or adjusted to human immunoglobulin sequences. The humanized, chimeric or partially humanized versions of the mouse monoclonal antibodies can, for example, be made by means of recombinant DNA technology, departing from the mouse and/or human genomic DNA sequences coding for H and L chains or from cDNA clones coding for H and L chains. Humanized forms of mouse antibodies can be generated by linking the CDR regions of non-human antibodies to human constant regions by recombinant DNA techniques (Queen et al., 1989; WO 90/07861). Alternatively, the monoclonal antibodies used in the method of the invention may be human monoclonal antibodies. Human antibodies can be obtained, for example, using phage-display methods (WO 91/17271; WO 92/01047).

As used herein, humanized antibodies refer also to forms of non-human (e.g. murine, camel, llama, shark) antibodies that are specific chimeric immunoglobulins, immunoglobulin chains, or fragments thereof (such as Fv, Fab, Fab', F(ab')₂ or other antigen-binding subsequences of antibodies) that contain minimal sequence derived from non-human immunoglobulin.

As used herein, human or humanized antibody or antibody fragment means an antibody having an amino acid sequence corresponding to that of an antibody produced by a human and/or has been made using any of the techniques for making human antibodies known in the art or disclosed herein. Human antibodies or fragments thereof can be selected by competitive binding experiments, or otherwise, to have the same epitope specificity as a particular mouse antibody. The humanized antibodies of the present invention surprisingly share the useful functional properties of the mouse antibodies to a large extent. Human polyclonal antibodies can also be provided in the form of serum from humans immunized with an immunogenic agent. Optionally, such polyclonal antibodies can be concentrated by affinity purification using amyloid fibrillar and/or non-fibrillar polypeptides or fragments thereof as an affinity reagent. Monoclonal antibodies can be obtained from serum according to the technique described in WO 99/60846.

Variable Regions and CDRs

A variable region of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies.

There are a number of techniques available for determining CDRs, such as an approach based on cross-species sequence variability (i.e., Kabat et al., Sequences of Proteins of Immunological Interest, (5th ed., 1991, National Institutes of Health, Bethesda Md.)); and an approach based on crystallographic studies of antigen-antibody complexes (Al-lazikani et al. (1997) J. Molec. Biol. 273:927-948). Alternative approaches include the IMGT international ImMunoGeneTics information system, (Marie-Paule Lefranc). The Kabat definition is based on sequence variability and is the most commonly used method. The Chothia definition is based on the location of the structural loop regions, wherein the AbM definition is a compromise between the two used by Oxford Molecular's AbM antibody modelling software (refer www.bioinf.org.uk: Dr. Andrew C. R. Martin's Group). As used herein, a CDR may refer to CDRs defined by one or more approach, or by a combination of these approaches.

In some embodiments, the invention provides an antibody or fragment thereof incorporated into a CAR, wherein said antibody or fragment thereof comprises at least one CDR, at least two, at least three, or more CDRs that are substantially identical to at least one CDR, at least two, at least three, or more CDRs of the antibody of the invention. Other embodiments include antibodies which have at least two, three, four, five, or six CDR(s) that are substantially identical to at least two, three, four, five or six CDRs of the antibodies of the invention or derived from the antibodies of the invention. In some embodiments, the at least one, two, three, four, five, or six CDR(s) are at least about 70%, 75%, 85%, 86%, 87%, 88%, 89%, 90%, 95%, 96%, 97%, 98%, or 99% identical to at least one, two or three CDRs of the antibody of the invention. It is understood that, for purposes of this invention, binding specificity and/or overall activity is generally retained, although the extent of activity may vary compared to said antibody (may be greater or lesser).

Additional Components of the CAR

In certain embodiments, the CARs contemplated herein may comprise linker residues between the various domains, added for appropriate spacing and conformation of the molecule, for example a linker comprising an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids.

Illustrative examples of linkers include glycine polymers; glycine-serine polymers; glycine-alanine polymers; alanine-serine polymers; and other flexible linkers known in the art, such as the Whitlow linker. Glycine and glycine-serine polymers are relatively unstructured, and therefore may be able to serve as a neutral tether between domains of fusion proteins such as the CARs described herein.

In particular embodiments, the binding domain of the CAR is followed by one or more "spacers" or "spacer polypeptides," which refers to the region that moves the antigen binding domain away from the effector cell surface to enable proper cell/cell contact, antigen binding and activation. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region. In one embodiment, the spacer domain comprises the CH2 and CH3 domains of IgG1 or IgG4.

The binding domain of the CAR may in some embodiments be followed by one or more "hinge domains," which play a role in positioning the antigen binding domain away from the effector cell surface to enable proper cell/cell contact, antigen binding and activation. A CAR may comprise one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8 alpha, CD4, CD28, PD1, CD 152, and CD7, which may be wild-type hinge regions from these molecules or may be altered. In another embodiment, the hinge domain comprises a PD1, CD 152, or CD8 alpha hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from the alpha, beta or zeta chain of the T-cell receptor, CD3ε, CD3ζ, CD4, CD5, CD8 alpha, CD9, CD 16, CD22, CD27, CD28, CD33, CD37, CD45, CD64, CD80, CD86, CD 134, CD 137, CD 152, CD 154, and PD1. In one embodiment, the CARs contemplated herein comprise a TM domain derived from CD8 alpha or CD28.

In particular embodiments, CARs contemplated herein comprise an intracellular signaling domain. An "intracellular signaling domain," refers to the part of a CAR that participates in transducing the message of effective CAR binding to a target polypeptide into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function.

CARs contemplated herein comprise one or more co-stimulatory signaling domains to enhance the efficacy, expansion and/or memory formation of T cells expressing CAR receptors. As used herein, the term, "co-stimulatory signaling domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen.

Polypeptides

"Peptide" "polypeptide", "polypeptide fragment" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring.

In various embodiments, the CAR polypeptides contemplated herein comprise a signal (or leader) sequence at the N-terminal end of the protein, which co-translationally or post-translationally directs transfer of the protein. Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Nucleic Acids

As used herein, the terms "polynucleotide" or "nucleic acid molecule" refers to messenger RNA (mRNA), RNA, genomic RNA (gRNA), plus strand RNA (RNA(+)), minus strand RNA (RNA(-)), genomic DNA (gDNA), complementary DNA (cDNA) or recombinant DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100%) sequence identity to any of the reference sequences described herein, typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

Polynucleotides can be prepared, manipulated and/or expressed using any of a variety of well-established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or MI 3 phage, and animal viruses. Examples of categories of animal viruses useful as vectors include, without limitation, retrovirus (including lentivirus), adenovirus, adeno-associated virus, herpesvirus {e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, the coding sequences of the chimeric proteins disclosed herein can be ligated into such expression vectors for the expression of the chimeric protein in mammalian cells. The "control elements" or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Vectors

In particular embodiments, a cell {e.g., an immune effector cell, such as a T cell) is transduced with a retroviral vector, e.g., gamma-retroviral or a lentiviral vector, encoding a CAR. For example, an immune effector cell is transduced with a vector encoding a CAR that comprises an anti-gp350/gp220 antibody or antigen binding fragment that binds a gp350 and/or gp220 polypeptide, with a transmembrane and intracellular signaling domain, such that these transduced cells can elicit a CAR-mediated cytotoxic response.

Retroviruses are a common tool for gene delivery. In particular embodiments, a retrovirus is used to deliver a polynucleotide encoding a CAR to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus.

In a preferred embodiment the invention therefore relates to a method for transfecting cells with an expression vector encoding a CAR. For example, in some embodiments, the vector comprises additional sequences, such as sequences that facilitate expression of the CAR, such a promoter, enhancer, poly-A signal, and/or one or more introns. In preferred embodiments, the CAR-coding sequence is flanked by transposon sequences, such that the presence of a transposase allows the coding sequence to integrate into the genome of the transfected cell.

In some embodiments, the genetically transformed cells are further transfected with a transposase that facilitates integration of a CAR coding sequence into the genome of the transfected cells. In some embodiments the transposase is provided as DNA expression vector. However, in preferred embodiments, the transposase is provided as an expressible RNA or a protein such that long-term expression of the transposase does not occur in the transgenic cells. For example, in some embodiments, the transposase is provided as an mRNA (e.g., an mRNA comprising a cap and poly-A tail). Any transposase system may be used in accordance with the embodiments of the present invention. However, in some embodiments, the transposase is salmonid-type Tel-like transposase (SB). For example, the transposase can be the so called "Sleeping beauty" transposase, see e.g., U.S. Pat. No. 6,489,458, incorporated herein by reference. In some embodiments, the transposase is an engineered enzyme with increased enzymatic activity. Some specific examples of transposases include, without limitation, SB 10, SB 11 or SB 100X transposase (see, e.g., Mates et al, 2009, Nat Genet. 41(6):753-61, or U.S. Pat. No. 9,228,180, herein incorporated by reference). For example, a method can involve electroporation of cells with an mRNA encoding an SB 10, SB 11 or SB 100X transposase.

A further aspect of the invention relates to a genetically modified immune cell comprising a nucleic acid molecule or vector as described herein, and/or expressing a CAR as described herein.

A further aspect of the invention relates to a vector comprising a nucleic acid molecule as described herein, preferably a viral vector, more preferably a gamma retroviral vector. In another aspect of the invention, the invention relates to a transposon vector, preferably a sleeping beauty vector, encoding and preferably capable of expressing the inventive CAR.

In a preferred embodiment the immune cells intended for administering in treatment of the diseases mentioned herein are genetically modified with a nucleic acid as described herein, encoding and expressing the CAR as described herein, using a "Sleeping beauty" transposon system, in particular a sleeping beauty transposase. The Sleeping Beauty transposon system is a synthetic DNA transposon designed to introduce precisely defined DNA sequences into the chromosomes of vertebrate animals, in the context of the present invention for the purposes of modifying immune cells to express the CAR as described herein. The sleeping beauty transposons combine the advantages of viruses and naked DNA. Viruses have been evolutionarily selected based on their abilities to infect and replicate in new host cells. Simultaneously, cells have evolved major molecular defense mechanisms to protect themselves against viral infections. Avoiding the use of viruses is also important for social and regulatory reasons. The use of non-viral vectors such as the sleeping beauty system therefore avoids many, but not all, of the defenses that cells employ against vectors. For this reason, the sleeping beauty system enables particularly effective and safe genetic modification of the immune cells for administration to a patient.

Sequence Variants:

Sequence variants of the claimed nucleic acids, proteins, antibodies, antibody fragments and/or CARs, for example those defined by % sequence identity, that maintain similar binding properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

The recitation "sequence identity" as used herein refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein sequence modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. Substitutions may be carried out that preferably do not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu; represent groups of conservative amino acids. This list is not exhaustive. For example, it is well known that Ala, Gly, Ser and sometimes Cys can substitute for each other even though they belong to different groups.

Substitution variants have at least one amino acid residue in the antibody molecule removed and a different residue inserted in its place. The sites of greatest interest for substitutional mutagenesis include the hypervariable regions, but FR alterations are also contemplated. If such substitutions result in a change in biological activity, then more substantial changes, denominated "exemplary substitutions" in the table immediately below, or as further described below in reference to amino acid classes, may be introduced and the products screened.

Potential Amino Acid Substitutions:

| Original residue | Preferred conservative substitutions | Examples of exemplary substitutions |
|---|---|---|
| Ala (A) | Val | Val; Leu; Ile |
| Asg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn, Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citrulline and methionine sulfoxide which are neutral non-polar analogs, phenylglycine which is an aromatic neutral analog; cysteic acid which is a negatively charged analog and ornithine which is a positively charged amino acid analog. Like the naturally occurring amino acids, this list is not exhaustive, but merely exemplary of the substitutions that are well known in the art.

Genetically Modified Cells and Immune Cells

The present invention contemplates, in particular embodiments, cells genetically modified to express the CARs contemplated herein, for use in the treatment of B cell related conditions. As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably. As used herein, the term "gene therapy" refers to the introduction of extra genetic material in the form of DNA or RNA into the total genetic material in a cell that restores, corrects, or modifies expression of a gene, or for the purpose of expressing a therapeutic polypeptide, e.g., a CAR. In particular embodiments, the CARs contemplated herein are introduced and expressed in immune effector cells so as to redirect their specificity to a target antigen of interest.

An "immune cell" or "immune effector cell" is any cell of the immune system that has one or more effector functions (e.g., cytotoxic cell killing activity, secretion of cytokines, induction of ADCC and/or CDC).

Immune effector cells of the invention can be autologous/autogeneic ("self") or non-autologous ("non-self," e.g., allogeneic, syngeneic or xenogeneic). "Autologous", as used herein, refers to cells from the same subject, and represent a preferred embodiment of the invention. "Allogeneic", as used herein, refers to cells of the same species that differ genetically to the cell in comparison. "Syngeneic", as used herein, refers to cells of a different subject that are genetically identical to the cell in comparison. "Xenogeneic", as used herein, refers to cells of a different species to the cell in comparison. In preferred embodiments, the cells of the invention are autologous or allogeneic.

Illustrative immune effector cells used with the CARs contemplated herein include T lymphocytes. The terms "T cell" or "T lymphocyte" are art-recognized and are intended to include thymocytes, immature T lymphocytes, mature T lymphocytes, resting T lymphocytes, cytokine-induced killer cells (CIK cells) or activated T lymphocytes. Cytokine-induced killer (CIK) cells are typically CD3- and CD56-positive, non-major histocompatibility complex (MHC)-restricted, natural killer (NK)-like T lymphocytes. A T cell can be a T helper (Th; $CD4^+$ T cell) cell, for example a T helper 1 (Th1) or a T helper 2 (Th2) cell. The T cell can be a cytotoxic T cell (CTL; $CD8^+$ T cell), $CD4^+CD8^+$ T cell, CD4 CD8 T cell, or any other subset of T cells. Other illustrative populations of T cells suitable for use in particular embodiments include naive T cells and memory T cells.

For example, when reintroduced back to patients after autologous cell transplantation, the T cells modified with the CAR of the invention as described herein may recognize and kill tumor cells. CIK cells may have enhanced cytotoxic activity compared to other T cells, and therefore represent a preferred embodiment of an immune cell of the present invention.

As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro.

The present invention provides methods for making the immune effector cells which express the CAR contemplated herein. In one embodiment, the method comprises transfecting or transducing immune effector cells isolated from an individual such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before and/or after being genetically modified (i.e., transduced or transfected to express a CAR contemplated herein).

In particular embodiments, prior to in vitro manipulation or genetic modification of the immune effector cells described herein, the source of cells is obtained from a subject. In particular embodiments, the CAR-modified immune effector cells comprise T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation, antibody-conjugated bead-based methods such as MACS™ separation (Miltenyi). In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flow through centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells can be further isolated by positive or negative selection techniques. One method for use herein is cell sorting and/or selection via negative magnetic immunoadherence or flow cytometry that uses a cocktail of monoclonal antibodies directed to cell surface markers present on the cells negatively selected.

PBMC may be directly genetically modified to express CARs using methods contemplated herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. $CD8^+$ cells can be obtained by using standard methods. In some embodiments, $CD8^+$ cells are further sorted into naive, central memory, and effector cells by identifying cell surface antigens that are associated with each of those types of $CD8^+$ cells.

The immune effector cells, such as T cells, can be genetically modified following isolation using known methods, or the immune effector cells can be activated and expanded (or differentiated in the case of progenitors) in vitro prior to being genetically modified. In a particular embodiment, the immune effector cells, such as T cells, are genetically modified with the chimeric antigen receptors contemplated herein (e.g., transduced with a viral vector comprising a nucleic acid encoding a CAR) and then are activated and expanded in vitro. In various embodiments, T cells can be activated and expanded before or after genetic modification to express a CAR, using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In a further embodiment, a mixture of, e.g., one, two, three, four, five or more, different expression vectors can be used in genetically modifying a donor population of immune effector cells wherein each vector encodes a different chimeric antigen receptor protein as contemplated herein. The resulting modified immune effector cells forms a mixed population of modified cells, with a proportion of the modified cells expressing more than one different CAR proteins.

In one embodiment, the invention provides a method of storing genetically modified murine, human or humanized CAR protein expressing immune effector cells which target a herpes viral protein, comprising cryopreserving the immune effector cells such that the cells remain viable upon thawing. A fraction of the immune effector cells expressing the CAR proteins can be cryopreserved by methods known in the art to provide a permanent source of such cells for the future treatment of patients afflicted with the B cell related condition. When needed, the cryopreserved transformed immune effector cells can be thawed, grown and expanded for more such cells.

In one embodiment the immune cell is preferably selected from the group consisting of a T lymphocyte or an NK cell, more preferably cytotoxic T lymphocytes.

In a preferred embodiment the genetically modified immune cell comprising a nucleic acid molecule or vector as described herein, and/or expressing a CAR as described herein, is characterised in that it is $CD4^+$ and/or $CD8^+$ T cell, preferably a mixture of $CD4^+$ and CD8+ T cells. These T cell populations, and preferably the composition comprising both $CD4^+$ and CD8+ transformed cells, show particularly effective cytolytic activity against various malignant B cells, such as B-NHL, preferably against those cells and/or the associated medical conditions described herein.

In a preferred embodiment the genetically modified immune cells comprising a nucleic acid molecule or vector as described herein, and/or expressing a CAR as described herein, are $CD4^+$ and $CD8^+$ T cells, preferably in a ration of 1:10 to 10:1, more preferably in a ratio of 5:1 to 1:5, 2:1 to 1:2 or 1:1. Administration of modified CAR-T cells expressing the CAR described herein at the ratios mentioned, preferably at a 1:1 CD4+/CD8+ ratio, lead to beneficial characteristics during treatment of the diseases mentioned herein, for example these ratios lead to improved therapeutic response and reduced toxicity.

Compositions and Formulations

The compositions contemplated herein may comprise one or more polypeptides, polynucleotides, vectors comprising same, genetically modified immune effector cells, etc., as contemplated herein. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringers solution; ethyl alcohol; phosphate buffer solutions; and any other compatible substances employed in pharmaceutical formulations.

In particular embodiments, compositions of the present invention comprise an amount of CAR-expressing immune effector cells contemplated herein. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cell effective to achieve the desired prophylactic result. Typically but not necessarily, since a prophylactic dose is used in subjects prior to or at an earlier stage of disease, the prophylactically effective amount is less than the therapeutically effective amount. The term prophylactic does not necessarily refer to a complete prohibition or prevention of a particular medical disorder. The tem prophylactic also refers to the reduction of risk of a certain medical disorder occurring or worsening in its symptoms.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject).

It can generally be stated that a pharmaceutical composition comprising the immune cells (T cells) described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells may be administered. CAR expressing cell compositions may be administered multiple times at dosages within these ranges. The cells may be allogeneic, syngeneic, xenogeneic, or autologous to the patient undergoing therapy.

Generally, compositions comprising the cells activated and expanded as described herein may be utilized in the treatment and prevention of diseases that arise in individuals who are immunocompromised. In particular, compositions comprising the CAR-modified T cells contemplated herein are used in the treatment of B cell malignancies. The CAR-modified T cells of the present invention may be administered either alone, or as a pharmaceutical composition in combination with carriers, diluents, excipients, and/ or with other components such as IL-2 or other cytokines or cell populations. In particular embodiments, pharmaceutical compositions contemplated herein comprise an amount of genetically modified T cells, in combination with one or more pharmaceutically or physiologically acceptable carriers, diluents or excipients.

Pharmaceutical compositions of the present invention comprising a CAR-expressing immune effector cell population, such as T cells, may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringers solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, compositions contemplated herein comprise an effective amount of CAR-expressing immune effector cells, alone or in combination with one or more therapeutic agents. Thus, the CAR-expressing immune effector cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

Therapeutic Methods

As used herein, the terms "individual" and "subject" are often used interchangeably and refer to any animal that exhibits a symptom of a disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a B cell malignancy, that can be treated with the cell-based therapeutics and methods disclosed herein. Suitable subjects include laboratory animals (such as mouse, rat, rabbit, or guinea pig), farm animals, and domestic animals or pets (such as a cat or dog). Non-human primates and, preferably, human patients, are included. Typical subjects include human patients that have a B cell malignancy, have been diagnosed with a B cell malignancy, or are at risk or having a B cell malignancy.

As used herein "treatment" or "treating" includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent" and similar words such as "prevented", "preventing" or "prophylactic" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In one embodiment, a method of treating a herpes virus associated condition in a subject in need thereof comprises administering an effective amount, e.g., therapeutically effective amount of a composition comprising genetically modified immune effector cells contemplated herein. The quantity and frequency of administration will be determined by such factors as the condition of the patient, and the type and severity of the patient's disease, although appropriate dosages may be determined by clinical trials.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

FIGURES

The invention is demonstrated by way of example by the following figures. The figures are to be considered as providing a further description of potentially preferred embodiments that enhance the support of one or more non-limiting embodiments of the invention.

BRIEF DESCRIPTION OF THE FIGURES

FIG. 1: 7A1 and 6G4 (CD28z) CAR designs and generation of CAR-T Cells.

FIG. 2: Potency of 7A1 and 6G4 gp350-CAR-T cells (CD28z) to recognize and kill a 293T cell line engineered to express gp350.

FIG. 4: Design of containing 7A1-gp350CAR-T cells with 4-1BB signaling, potency to rec-ognize and kill a 293T/gp350 cell line and potency to recognize the B95.8 cell line.

FIG. 6: Humanized mice infected with B95.8-EBV-GFP and treated with 7A1-gp350CAR-T (CD28z).

FIG. 7: Humanized mice pre-treated with 7A1-gp350CAR-T (CD28z) and infected with EBV-B95.8-fLuc.

FIG. 8: Overview of CAR constructs of the present invention created and tested.

FIG. 9: Humanized NRG mice pre-treated with sorted CAR+CD8+ or CAR+CD4+/CD8+7A1-gp350CAR-T (CD28z) and infected with the EBV-M81/fLuc2 strain.

FIG. 10: Humanized mice infected with EBV-M81/fLuc2 and treated with sorted CD8+7A1-gp350CAR-T (CD28z).

DETAILED DESCRIPTION OF THE FIGURES

Figure 3:
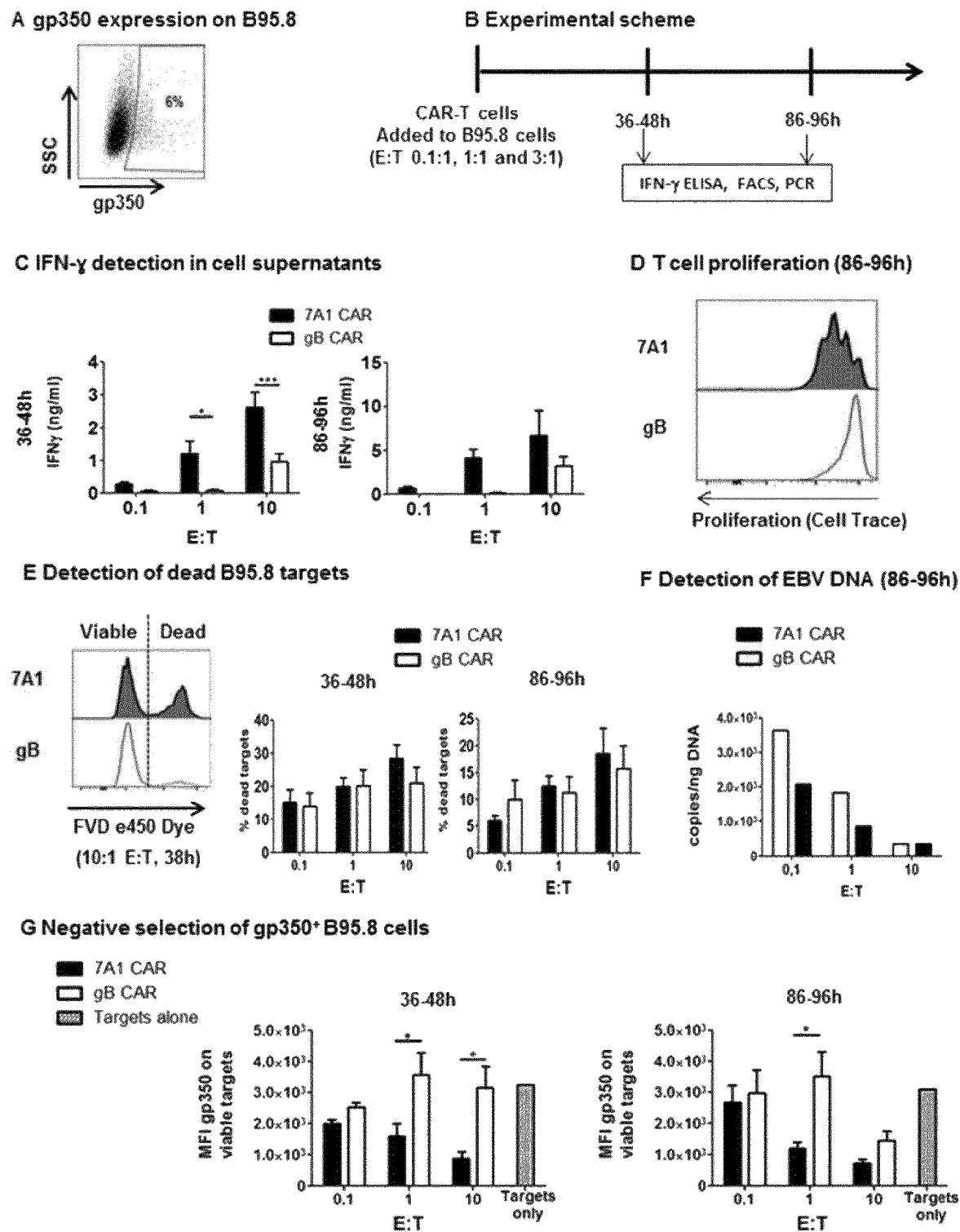
FIG. 3: Potency of 7A1-gp350-CAR-T cells (CD28z) to kill the EBV-latently infected B95.8 cell line.

FIG. 1: 7A1 and 6G4 (CD28z) CAR Designs and Generation of CAR-T Cells.

A 7A1 and 6G4 monoclonal antibodies were diluted to different doses (ng) and incubated with EBV-GFP virus prior to infection of Raji cells. Neutralization activity is shown as reduction of detection of GFP+ infected cells. B Schematic representation of CAR constructs containing the CD28z signaling domain and recognizing EBV-gp350 (7A1 or 6G4). As a cognate negative control, we used a CAR construct recognizing HCMV-gB (gB). Restriction digestion with Pml1, Cla1 and BamHI confirming structure of retroviral constructs containing CARs are shown on an additional sheet (FIG. 1 (cont.). C Overview of the commonly used methods here employed for retroviral gene transfer of CARs into adult peripheral blood or from cord blood T cells. D Left panel: representative example of flow cytometry analyses for detection of CARs on the cell surface. CARs were detected with AF647- or AF488-conjugated goat anti-human IgG-Fc Fab-fragments (Jackson ImmunoResearch, West Grove, PA) directed against the IgF4 hinge incorporated in the constructs. Graphs on the right: Detection of gp350CAR (7A1, n=7, and 6G4, n=6) relative to gBCAR (n=4) expression on CD4+- and CD8+-CAR-T cells produced with adult peripheral blood T cells. E Detection of gp350CAR (7A1) expression on CD4+- and CD8+-CAR-T cells produced with cord blood T cells from 5 different donors.

FIG. 2: Potency of 7A1 and 6G4 gp350-CAR-T Cells (CD28z) to Recognize and Kill a 293T Cell Line Engineered to Express Gp350.

A Flow cytometry analysis of gp350+ expression on 293T w.t. cells (grey) compared with analysis of 293T cells transduced with a lentiviral vector expressing gp350 (black). Surface gp350 was detected with the mouse antibody 72A1 and goat anti-mouse IgG AF647. B Experimental scheme: 293T or 293T/gp350 cells were seeded on plates and a day later CAR-T cells were added. After 24 and 48 h of co-culture, ELISA and FACS analyses were performed. C IFN-γ detection in cell supernatants showing high specificity of both 7A1 and 6G4 gp350CAR-T cells against 293T/gp350 at both lower (1:1) and higher (3:1) effector to target ratios, whereas the negative control gBCAR-T cells did not recognize the 293T/gp350 target. These assays were performed one time with triplicate cultures run in parallel. Statistical analyses were performed with two-way ANOVA and Bonferroni post-test. *** indicate p<0.001. D For detection of dead 293T/gp350 target cells, the fixable viability dye (FVD) e450 (eBioscience™) was added to the cells prior to flow cytometry analyses, allowing the distinction between viable and dead cells. The panels on the left show representative examples of 7A1 and 6G4 gp350CAR-T cells resulting into high frequencies of dead 293T-gp350 cells, whereas gBCAR-T cells did not promote cell death. The graphs on the right depict the quantified cell death after 24 h and 48 h of co-culture, showing higher killing effects at the higher effector to target ratios (3:1). E Frequencies of T cells relative to the targets was quantified by flow cytometry showing a preferential expansion of 7A1 and 6G4 gp350 CAR-T cells at E:T 3:1 in comparison with gB-CAR-T cells. F Analyses of gp350 expression on 293T/gp350 target cells showed that co-cultures with of 7A1 and 6G4 gp350 CAR-T cells at E:T 3:1 resulted into antigenic loss, i.e. negative selection of gp350+ targets.

FIG. 3: Potency of 7A1-Gp350-CAR-T Cells (CD28z) to Kill the EBV-Latently Infected B95.8 Cell Line.

A Flow cytometry analysis of gp350+ expression on a sub-population (around 6%) of latently infected B95.8 cotton top tamarin cell line. Surface gp350 was detected with the mouse antibody 72A1 and goat anti-mouse IgG AF647. B Experimental scheme: B95.8 cells were seeded on plates and shortly after CAR-T cells were added ad different E:T ratios. After 36-48 and 86-96 h of co-culture, ELISA and FACS analyses were performed. These analyses represent merged data from four independent experiments using one donor. C IFN-γ detection in cell supernatants showing high reactivity of 7A1-gp350CAR-T cells against B95.8 cells, whereas no to low reactivity of the gBCAR-T control cells at higher (1:1 and 10:1) effector to target ratios, whereas the negative control gBCAR-T cells did not recognize the B95.8 targets. These assays were performed 12 times for ratios 10:1 and 1:1 and 9 times for ratio 0.1:1. Statistical analyses were performed with two-way ANOVA and Bonferroni post-test. * indicates p<0.05 and *** indicate p<0.001. D CAR-T cells were marked with the proliferation dye Cell-Trace (Thermo Fisher) prior to co-culture. Analysis by flow cytometry showed that after 86 h of co-culture (E:T ratio of 10:1), 7A1-gp350CAR-T cells showed loss of the dye and three waves of proliferation whereas gB-CAR-T cells showed little loss of the marking dye. Representative results from four experiments. E For detection of dead B95.8 cells, the fixable viability dye (FVD) e450 (eBioscience™) was added to the cells prior to flow cytometry analyses, allowing the distinction between viable and dead cells. The panels on the left show representative examples of 7A1-gp350CAR-T cells resulting into high frequencies of dead B95.8 cells, but gBCAR-T cells did not promote cell death. The graphs on the right depict the quantified cell death after shorter and longer periods of co-culture, showing higher killing effects at the higher effector to target ratios (10:1). F Quantification of EBV DNA in cells obtained after co-culture was performed by an in house PCR method by detection of DNA sequences encoding for EBV BALF5 by qRT-PCR. Reduction of EBV copy numbers were observed after 86 h of co-culture with 7A1 CAR T cells. G Analyses of gp350 expression on B95.8 cells was measured by flow cytometry after 36-48 h and 86-96 h of co-culture showing loss of gp350 expression after co-culture with 7A1-gp350CAR-T compared to gBCAR-T cells. These assays were performed four times for ratios 10:1 and 1:1 and 3 times for ratio 0.1:1. Statistical analyses were performed with two-way ANOVA and Bonferroni post-test. * indicates p<0.05.

FIG. 4: Design of Containing 7A1-gp350CAR-T Cells with 4-1BB Signaling, Potency to Recognize and Kill a 293T/Gp350 Cell Line and Potency to Recognize the B95.8 Cell Line.

A Schematic representation of CAR constructs containing the 4-1BB signaling domain and recognizing EBV-gp350 (7A1). As a cognate negative control we used a CAR construct recognizing HCMV-gB (gB). B Flow cytometry analyses for detection of 4-1BB CARs on the cell surface of $CD4^+$- and $CD8^+$-CAR-T cells produced with adult peripheral blood T cells. CARs were detected with goat anti-human IgG-Fc Fab-fragments directed against the IgF4 hinge incorporated in the constructs. C Experimental scheme: 293T Vs. 293T/gp350 or B95.8 cells were seeded on plates and CAR-T cells were added. After 48 h of co-culture, ELISA and FACS analyses were performed. D IFN-γ detection in cell supernatants showing specificity of 7A1-gp350CAR-T-41BB cells against 293T/gp350 at higher (3:1, 10:1) effector to target ratios, whereas the negative control gBCAR-T cells was unspecific to 293T/gp350 target. D Quantified cell death after 48 h of co-culture, showing specific killing effects of 7A1-gp350CAR-T-41BB only at the intermediate effector to target ratios (3:1). F IFN-γ detection in cell supernatants showing specificity of 7A1-gp350CAR-T-41BB cells against B95.8 cells at lower (1:1, 3:1) effector to target ratios.

Figure 5:
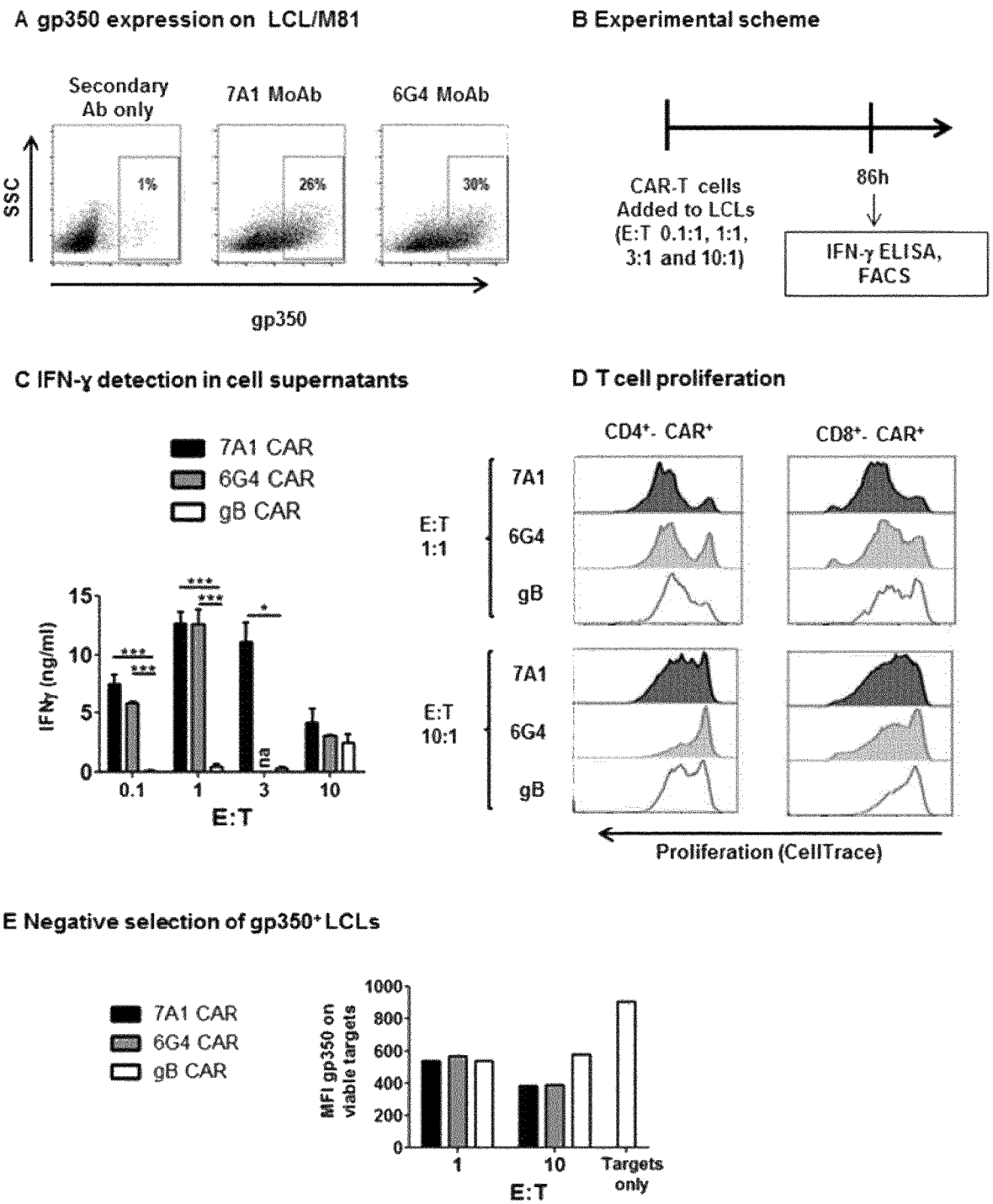
FIG. 5: Demonstration of the potency of 7A1-gp350CAR-T and 6G4-gp350CAR-T cells (CD28z) to recognize and be activated by autologous LCL cell lines immortalized with M81-EBV-GFP.

FIG. 5: Demonstration of the Potency of 7A1-gp350CAR-T and 6G4-gp350CAR-T Cells (CD28z) to Recognize and be Activated by Autologous LCL Cell Lines Immortalized with M81-EBV-GFP.

A Flow cytometry analysis of $gp350^+$ expression on sub-populations (around 26-30%) of latently infected LCLs obtained after immortalization of B cells with M81 EBV. Surface gp350 could be detected with the antibody 7A1 or 6G4 used as primary antibodies for staining. B Experimental scheme: LCLs cells were seeded on plates and shortly after autologous CAR-T cells were added ad different E:T ratios. After 86 h of co-culture, ELISA and FACS analyses were performed. These analyses represent merged data from two independent experiments. C IFN-γ release detected in supernatants after 86 h of co-culture showing T cell activation of 7A1 and 6G4-CAR-T in contrast to none to poor activation of gBCAR-T cells. These assays were performed six times for ratios 10:1 and 1:1 and three times for ratio 3:1 and 0.1:1. Statistical analyses were performed with two-way ANOVA and Bonferroni post-test. * indicates p<0.05 and *** indicate p<0.001. D CAR-T cells were marked with the proliferation dye CellTrace (Thermo Fisher) prior to co-culture. Analysis by flow cytometry showed that after 86 h of co-culture (E:T ratio of 1:1 or 10:1), $CD4^+$ and $CD^8+$ 7A1-gp350CAR-T cells showed the highest levels of loss of the dye compared with 6G4-gp350CAR-T and gB-CAR-T cells. E Analyses of gp350 expression on LCLs was measured by flow cytometry after 86 h of co-culture showing loss of gp350 expression after co-culture with 7A1-gp350CAR-T and 6G4-gp350CAR-T compared to gB-CAR-T cells.

FIG. 6: Humanized Mice Infected with B95.8-EBV-GFP and Treated with 7A1-gp350CAR-T (CD28z).

A Experimental scheme: Nod-Rag$^{-/-}$II2γcR$^{-/-}$ (NRG) mice were irradiated and transplanted with $CD34^+$ cells isolated from cord blood. 16 weeks later, mice were infected i.v. with EBV-B95.8/GFP ($10^5$ GRU i.v.). Five weeks after infection, 5×10 6 7A1-gp350CAR-T cells generated from the same cord blood donor were infused into 2 mice, and 3 mice were maintained as non-treatment controls. Four weeks after CAR-T cell administration, mice were sacrificed for analyses. Tumors could be detected in spleens of one CAR-T and one control animal. B Flow cytometry analyses for detection of $CAR^+$ $CD45^+/CD3^+$ and $CD45^+/CD3^+/CD8$ cells in peripheral blood was analyzed weekly.

Detection of CAR-T cells was highest 2 weeks after infusion, reducing until 4 weeks. C Flow cytometry analyses for detection of CAR+CD45+/CD3$^+$ and CD45+/CD3+/CD8 cells in spleen and tumors was analyzed after euthanasia. CAR-T cells (mostly $CD8^+$ T cells) could be detected in the range of 1.5%-2.5% T cells in spleen and tumor tissues. D DNA isolated from spleen and tumor tissues was analyzed by RT-qPCR. High levels of EBV DNA could be only detected in the tumor obtained from the control mouse, but not from the tumor obtained from the CAR-T treated mouse. E Tumor sections were analyzed by EBER in situ hybridization, demonstrating sparse to rare EBER staining in the tumor obtained from the CAR-T treated mouse and frequent EBER staining in the tumor obtained from the control mouse.

FIG. 7: Humanized Mice Pre-Treated with 7A1-gp350CAR-T (CD28z) and Infected with EBV-B95.8-fLuc.

A Experimental scheme: Nod-Rag$^{-/-}$II2γcR$^{-/-}$ (NRG) mice were irradiated and transplanted with $CD34^+$ cells isolated from cord blood. Twenty-five weeks later, 5×10 6 7A1-gp350CAR-T cells generated from the same cord blood donor were infused in one mouse. One day later, one CAR-T and one control mouse were infected i.v. with EBV-B95.8/fLUC ($10^5$ GRU i.v.). Six weeks after infection, mice were sacrificed for analyses. B Sequential bioluminescence optical imaging analyses showing lower EBV-fLuc infection and spread in CAR-T pre-treated mouse relative to control mouse at 4 and 6 weeks after EBV challenge. C Longitudinal analyses of bioluminescence signal in spleen area from 2 to 6 weeks after EBV infection. D Bioluminescence signal detected in the regions of liver and salivary gland regions at endpoint analysis. E Longitudinal analyses of detection CAR-T cells in peripheral blood showing 3% CD45+/CD3+/CAR+ and 1.5% CD45+/CD3+/CD8+/CAR+ cells one week after administration, but reducing over time. F $CD4^+$ CAR-T cells could be detected in bone marrow and $CD8^+$ CAR-T cells could be detected in spleen at endpoint analysis.

FIG. 8: Overview of CAR constructs of the present invention created and tested.

Provided is an overview of the various constructs generated by the inventors. The majority of all CAR constructs has been generated and expressed in both lentiviral and retroviral vectors. CAR-T production has been completed for constructs #1, 3, 9, 11. Experimentation in 293T and B95.8 co-culture settings (as described above) has been completed for constructs #1 and 3, and the above mentioned in vivo experiments conducted with construct #3. Additional experimentation is ongoing demonstrating the desired functional efficacy for the remaining constructs.

FIG. 9: Humanized NRG mice pre-treated with sorted CAR+CD8+ or CAR+CD4+/CD8+7A1-gp350CAR-T (CD28z) and infected with the EBV-M81/fLuc2 strain.

A Experimental scheme: Nod-Rag$^{-/-}$IL2ycR$^{-/-}$ (NRG) mice were irradiated and transplanted with CD34$^+$ cells isolated from cord blood. 17 weeks later, humanized mice were administered with PBS and served as controls (CTR, n=3) or infused i.v. with 2×10 6 FACS-sorted CAR+/CD8+ (n=3) or with CAR+/CD4+/CD8+7A1-gp350CAR-T cells (n=4). The flow cytometry dot-plot graphs show exemplary results for CARP and CD8+ or CD4$^+$ T cell populations before and after sorting. A day after T cell administrations, all mice were infected with the EBV-M81/fLuc2 strain (10$^6$ GRU, i.v.). Mice were regularly bled to monitor the dynamics of reconstitution of human lymphocytes and monitored by optical imaging analyses for bio-distribution of EBV infection. Mice were euthanized 5 weeks after EBV infection. B, C Flow cytometry analyses of peripheral blood for detection of human CD45$^+$ and human CD8$^+$ cells, respectively. All mice maintained long-term reconstitution with human leukocytes. D Upper panels: Luciferase signal of EBV-M81/fLuc2 in the left side view of infected humanized mice is displayed in a 2D bioluminescence analysis using IVIS SpectralCT and LiveImage and performed in weeks 2, 3 4 and 5 after infection. Lower graphs: Quantification of the intensity of bioluminescence (Flux, represented as photons per second) in the full body of the mice over the course of the experiment. The graphs depict the quantified values for optical imaging analyses obtained for each mouse in the separate cohorts and the calculated merged values comparing the three cohorts (the standard deviation for each analysis is indicated). The data show higher levels of EBV infection in the CTR cohort compared with mice pre-treated with CD8$^+$ or with CD4$^+$/CD8$^+$7A1-gp350CAR-T cells. E DNA isolated from spleen and bone marrow samples was analyzed by qRT-PCR. EBV DNA was detected more frequently in samples obtained from CTR (5/6) in comparison with CD8$^+$ (2/6) and CD4$^+$/CD8$^+$ (4/6) CAR-T treated mice. For the remaining mice, the PCR showed non-detectable (n.d.) results. F Panels show the correlations for each individual mouse between values obtained by optical imaging analyses (full body) and values obtained for qRT-PCR for detection of EBV DNA in spleen and bone marrow. The squares drawn around the dots in the lower left corner of the graphs are to indicate that mice treated with CAR-T cells clustered together in the lower values, whereas values for control mice were more scattered.

FIG. 10: Humanized Mice Infected with EBV-M81/fLuc2 and Treated with Sorted CD8+7A1-gp350CAR-T (CD28z)

A Experimental scheme: Nod-Rag$^{-/-}$IL2ycR$^{-/-}$ (NRG) mice were irradiated and transplanted with CD34$^+$ cells isolated from cord blood. 17 weeks later, mice were infected i.v. with the EBV-M81/fLuc2 strain (10$^6$ GRU, i.v.). 3 and 5 weeks after EBV infections, FACS-sorted CAR$^+$CD8$^+$7A1-gp350CAR-T cells generated from the same cord blood donor were infused (CD8$^+$CAR, 2×10 6 cells i.v., n=7). The flow cytometry dot-plot graphs show exemplary results for CAR$^+$ and CD8$^+$ populations before and after sorting. EBV-infected humanized mice administered i.v. with PBS served as controls (CTR, n=6). Mice were regularly bled to monitor the dynamics of reconstitution of human lymphocytes and monitored by optical imaging analyses for bio-distribution of EBV infection. The arrows in figures and graphs depict the time-points when CAR-T cells were administered. Mice were euthanized 8 weeks after EBV infection. B, C Flow cytometry analyses for detection of human CD45$^+$ and human CD8$^+$ cells in peripheral blood, respectively. All mice maintained long-term reconstitution with human leukocytes. D Upper panels: Luciferase signal of EBV-M81/fLuc2 infected humanized mice is displayed in the left side view or frontal view in a 2D bioluminescence analysis using IVIS SpectralCT and LiveImage and performed in weeks 2, 3 4 and 5 after infection. Lower graphs: Quantification of the intensity of bioluminescence (Flux, defined as photons per second) in the full body of the mice over the course of the experiment. The graphs depict the quantified values for optical imaging analyses obtained for each mouse in the separate cohorts and the calculated merged values comparing the three cohorts (the standard deviation for each analysis is indicated). The data obtained for weeks 6 and 8 show higher levels of EBV infection in the CTR cohort compared with mice treated with CD8$^+$CAR-T cells. E DNA isolated from spleen, liver and bone marrow of the mice was analyzed by qRT-PCR. A 50% reduction in the qRT-PCR signal can be observed for spleen and bone marrow of CD8$^+$CAR-treated mice compared with CTR. F Panels show the correlations for each individual mouse between values obtained by optical imaging analyses (region of spleen, liver or full body) and values obtained for qRT-PCR for detection of EBV DNA in spleen, liver and bone marrow. The squares drawn around the dots in the lower left corner of the graphs are to indicate that mice treated with CAR-T cells clustered together in the lower values, whereas values of control mice were more scattered. G Bioluminescence optical imaging analyses were performed with isolated organs. Mice in CTR cohort showed higher incidence of EBV infections (kidney (66%), brain (33%) and lungs (50%)) than mice treated with CD8$^+$CAR-T cells (kidney (29%), brain (14%) and lungs (29%)).

EXAMPLES

The invention is demonstrated by way of the examples disclosed below. The examples provide technical support for and a more detailed description of potentially preferred, non-limiting embodiments of the invention.

Preclinical in vitro proof-of-concept experimentation is presented below demonstrating efficacy in appropriate in vitro and in vivo models. FIG. 8 presents an overview of the various CAR constructs generated.

Example 1: Engineering of Functional CARs Based on the Amino-Acid Sequences of the Heavy and Light Chains of 7A1 and 6G4

The invention is based on the engineering of functional CARs based on the amino-acid sequences of the heavy and light chains of 7A1 and 6G4 both antibodies known to have a high neutralization capacity against EBV. The corresponding DNA was synthesized commercially using a codon-optimization approach. A retroviral vector expressing CARs and signaling through the CD28zeta chain was employed. The DNA fragments encoding for VH and VL were subcloned into the retroviral vector backbone and clones were selected by restriction digestion and confirmed by DNA sequencing analysis. FIG. 1A shows the neutralization capacity of both antibodies. FIG. 1B provides an overview of the retroviral vector map of both 6G4 and 7A1 gp350-

CAR constructs and corresponding restriction digests. The plasmid constructs were used for transfection of 293T cells using the Calcium Phosphate DNA precipitation technique to generate retroviral vectors. Subsequently, T cells obtained from peripheral blood mononuclear cells (PBMCs) or the CD34⁻ fraction of cord blood mononuclear cells (CBMCs) were stimulated in vitro with cytokines and activating immune beads and transduced with retroviral vectors, as shown in FIG. 1C. FIG. 1D shows CAR expression on T cells from PBMCs analyzed by flow cytometry using an antibody recognizing an epitope in the IgG4 hinge. Expression of the 7A1-gp350-CAR was higher than the 6G4-gp350-CAR. FIG. 1E presents data on expression levels reached on cord blood derived T cells.

Example 2: Demonstration of the Potency of Gp350-CAR-T Cells to Kill a 293T Cell Line Engineered to Express Gp350

FIG. 2 presents data supporting the potency of 7A1 and 6G4-gp350-CAR-T cells to kill 293T cells engineered to express gp350. To test cytotoxic effects of gp350-CAR-T, CAR-T cells were co-cultured with 293T lentivirally transduced to stably express gp350 (FIG. 2A). Analysis of co-cultures was performed 24 and 48 h after co-culture (FIG. 2B). 6G4 and even more pronounced 7A1-CAR-T secreted high amounts (>15 ng/ml) of IFN-γ in the presence of 293T/gp350 compared to control CAR-T. An accumulative effect over time could be observed with increasing levels after 48 h compared to 24 h (FIG. 2C). Cytotoxic effects were detectable as early as 24 h after co-culture especially in the 3:1 effector to target ratio and with 7A1-CAR-T cells. After 48 h, also lower ratios showed increased amounts of dead targets compared to co-cultures without gp350 (FIG. 2D). Relative amounts of T cells were increased in co-cultures with gp350-CAR-T in 3:1 effector to target ratio assumingly caused by a synergistic effect of target killing and proliferation of T cells (FIG. 2E). Further, another phenomenon could be observed. 24 h after co-culture we saw an out-proliferation of 293T negative for gp350 in cultures with 7A1 and 6G4-CAR-T cells reflecting the selective pressure forced upon the target cells. This effect was even more pronounced after 48 h of co-culture with 7A1-CAR-T cells (FIG. 2F).

Example 3: Demonstration of the Potency of 7A1-Gp350-CAR-T Cells to Kill the EBV-Latently Infected B95.8 Cotton Top Tamarin Cell Line FIG. 3 presents data supporting the potency of 7A1-gp350-CAR-T cells to kill EBV-latently infected cell lines. B95.8 is a lymphoblastoid cell line derived from the cotton-top tamarin infected with EBV and also producing EBV viral particles. Surface staining for gp350 revealed expression of gp350 (FIG. 3A). After co-culture of B95.8 cells with CAR-T cells, analyses were performed 36 to 48 and 86 to 96 hours after (FIG. 3B). Analysis of the supernatant of the co-cultures revealed a dose-dependent IFN-γ release as well as an increasing accumulation of such to later time points (FIG. 3C). Labeling of the CAR-T cells prior to co-culture with a proliferation dye showed increased proliferation of gp350-CAR-T upon co-culture with target cells whereas no proliferation could be tracked in the control CAR-T group (FIG. 3D). Cytotoxic effects could be detected in high effector to target ratios already after 36-48 hours. 7A1-CAR-T cells showed increased cytotoxic effects than gB-CAR-T only in 10:1 effector to target ratios (FIG. 3E). Isolation of DNA followed by a BALF4 PCR to detect EBV copy numbers revealed decreased levels of EBV copies in gp350-CAR-T co-cultures compared to control CAR-T groups (FIG. 3F). However, whether this effect is caused by out-proliferation of T cells or killing of B95.8 cells remains unclear. Surface staining of gp350 on target cells after co-culture showed a dose-dependent loss of gp350 on target cells suggesting killing of gp350⁺ targets (FIG. 3G).

Example 4: Demonstration that 7A1-Gp350-CAR-T Containing a 4-1BB Signaling Recognize 293T/Gp350 and B95.8 Targets FIG. 4 presents data supporting the potency of 7A1-gp350-CAR-T with a 4-1BB signaling domain (FIG. 4A) that can be expressed on CD4⁺ and CD8⁺ T cells (FIG. 4B) in in vitro experiments using 293T/gp350 and B95.8 targets (FIG. 4C). At 3:1 and 10:1 E:T ratios higher levels of IFN-γ were evident in the gp350CAR-T cell cultures with the 293T/gp350 target (100-400 pg/ml) than in the gBCAR-T co-cultures (10-50 pg/ml) (FIG. 4D). Preferential killing of 293T/gp350 by gp350CAR-T was seen at the 3:1 E:T ratio (FIG. 4E). Co-culture of B95.8 cells with gp350CAR-T cells resulted in higher IFN-γ detection at all E:T ratios tested (FIG. 4F). Overall, these results showed that gp350CAR-T with the 4-1BB domain were functional, but produced weaker effects than gp350CAR-T with the CD28z domain.

Example 5: Demonstration of the Potency of 7A1-Gp350-CAR-T and 6G4-Gp350-CAR-T Cells to Recognize and be Activated by a Same Donor-Derived LCL Cell Line Immortalized with M81 EBV FIG. 5 presents data supporting the potency of 7A1-gp350-CAR-T cells and 6G4-gp350-CAR-T cells with the CD28z domain to recognize a donor-derived lymphoblastoid cell line (LCL) immortalized with the EBV viral strain M81. CD19⁺ cells were infected with EBV-M81 virus and after complete transformation checked for surface gp350 expression. Both antibody epitopes, 7A1 and 6G4, were detectable at high levels on the surface (FIG. 5A). CAR-T cells were co-cultured with LCLs and analysis was performed after 86 hours of co-culture (FIG. 5B). When co-cultured with gp350-CAR-T cells high levels of IFN-γ could be detected after 86 h. Highest levels of IFN-γ were observed in 3:1 and 1:1 ratios not in the highest ratio of 10:1 suggesting either a use of IFN-γ or an inhibiting effect of such high amounts of CAR-T cells (FIG. 5C). T cell proliferation of 7A1-CAR-T cells could be detected in comparison to control CAR-T (FIG. 5D). Loss of gp350 on target cells could also be detected especially in higher ratios of 7A1-CAR-T after 86 h indicating that gp350⁺ targets were killed however we could not detect increased amounts of dead targets with our FACS-based viability assay (FIG. 5E).

Example 6: 7A1-Gp350-CAR-T Cells were Tested In Vivo in an EBV Infection Model Using Humanized Mice Reconstituted with the Human Immune System FIG. 6 shows 7A1-gp350-CAR-T cell efficacy in vivo in an EBV infection model using humanized mice. NRG mice were irradiated and hCD34⁺ cells were transplanted i.v. Sixteen weeks later, mice were infected with EBV-B95.8/GFP. Five weeks after EBV infection, mice were infused with 5×10⁶ 7A1-gp350-CAR-T cells (same donor matched to the hCD34 cells). Peripheral blood was taken weekly and mice were sacrificed 4 weeks following CAR-T cell injection (FIG. 6A). CAR-T cells were detected at high levels in peripheral blood and reached peak values two weeks post injection (FIG. 6B). At endpoint analysis, autopsy revealed tumor formation in spleen in one mouse with and one without CAR-T cells. Other mice did not show macroscopic tumor formation. Splenic and tumor tissues were then analyzed for presence of CAR-T cells. In spleen CAR-T cells were detected in both mice that received CAR-T cells in the beginning. In tumor tissue of the mouse that initially received CAR-T cells high amounts of CAR-T cells were detected. Further, levels were exceeding the ones measured in healthy splenic tissue suggesting detection of the tumor by CAR-T cells (FIG. 6C). Further, DNA was isolated from spleen and tumor tissues and analyzed by RT-qPCR. Viral DNA copies were found in splenocytes of both mice developing a tumor. While high amounts of viral DNA copies were found in the tumor of the mouse without CAR-T cells, only baseline PCR signal was detectable in the tumor of the mouse with CAR-T cells indicating killing of EBV⁺ tumor cells by CAR-T cells (FIG. 6D). Histopathological analysis of tumor sections also revealed lower levels of EBER staining in the tumor of the mice treated with CAR-T cells (FIG. 6E).

Example 7: In Vivo Testing Gp350-CAR-T in EBV Humanized Mouse Model EBV/B95.8fLuc More extensive testing of 7A1-CAR-T cells in vivo to control and eradicate local and systemic EBV lymphoma and malignancies has been carried out, making use of a system in which EBV-B95.8/fLUC virus spread and tumor formation can be followed dynamically by non-invasive optical imaging. Results of a pilot experiment are shown in FIG. 6. NRG mice were irradiated and hCD34+ cells were transplanted i.v. 26 weeks later, one mouse was infused with 5×10 6 7A1-CAR-T cells (same donor matched to the hCD34 cells). One day later, both mice were infected with EBV/B95.8-fLuc. Peripheral blood was taken every second week and spread of infection was monitored every second week by IVIS Imaging. Mice were sacrificed 6 weeks following CAR-T cell injection (FIG. 7A). 4 weeks after infection, bioluminescence detection by optical imaging analyses revealed drastic differences in spread of infection. Whereas in the mice that received CAR-T cells infection was limited to the spleen, spread of infection to the liver was observable in the one without CAR-T cells. However, two weeks later although signal in the CAR-T cells treated mouse was still lower than in the control mouse also in the CAR-T cells treated mouse spread of infection had occurred (FIG. 7B). This suggests control of infection in the mouse with CAR-T cells until week 4 after infection. This is also underlined by quantification of spleen signal over the course of the experiment. Until week 4 signal in spleen in CAR-T treated mouse stayed stable whereas control mice showed rapid increase in signal from early on (FIG. 7C). At endpoint analysis, bioluminescence signal in liver and salivary glands regions were also measured and revealed lower signal in the mouse with CAR-T cells compared to control mouse (FIG. 7D). CAR-T cells were initially detected in blood but then levels decreased indicating a migration out of the blood stream into the tissues (FIG. 7E). This hypothesis is supported by the detection of CD4⁺ and CD8⁺CAR-T cells in spleen and bone marrow at endpoint analysis (FIG. 7F).

Example 8: Humanized NRG Mice Pre-Treated with Sorted CAR⁺CD8⁺ or CAR⁺CD4⁺/CD8⁺ Derived from 7A1-gp350CAR-T (CD28z) Cells and Infected with the EBV-M81/fLuc2 Strain FIG. 9 shows the effects of 7A1-gp350-CAR-T cells that were sorted as CAR+CD8⁺ cells or sorted and then recombined 1:1 as CAR⁺CD4⁺ plus CD8⁺ T cells and administered into humanized mice. The CAR construct employed was #3 according to FIG. 8, namely "gp350CAR7B(S.28.z)" derived from the 7A1 antibody, comprising the an IgHL-VH-G4S-VL scFV, an IgG Fc CH3 spacer and CD28-CD34ζ signaling domain. The EBV-M81fLuc2 infection in humanized mice was followed non-invasively and dynamically by optical imaging analyses. Seventeen weeks after stem cell transplantation, mice were administered with the CAR-T cells (CAR⁺CD8⁺ or CAR⁺CD4⁺ plus CD8⁺) or with PBS as control group and a day later they were infected with EBV. We observed a very consistent pattern of viral distribution, i.e., initially in spleen and then spreading systemically. Although immune reconstitution with endogenous leukocytes progressed normally for the mice in the different cohorts (FIG. 9B, C), we were unsuccessful in detecting CAR-T cells in peripheral blood or in lymphatic tissues of the mice. Nevertheless, a single administration with both CAR⁺CD8⁺ or CAR⁺CD4⁺ plus CD8⁺ cells prior to infection resulted in a diminution of EBV infection and spread monitored by optical imaging analyses (FIG. 9D). Further, DNA was isolated from spleen and bone marrow and analyzed by qRT-PCR. Viral DNA copies were found in splenocytes of all control mice, but were not detectable in spleen of several of the mice pre-treated with CAR-T cells (FIG. 9E). A similar trend was observed for bone marrow analyses (FIG. 9E). We observed a correlation between the data obtained by optical imaging and PCR, indicating that data of mice treated with CAR-T cells clustered apart from data of control mice (FIG. 9E). For these proof-of-concept experiments, data acquisition was not blinded and sample sizes were not statistically determined prior to experiments. Statistical analysis was performed using the GraphPad Prism software (Graphpad Software Inc., La Jolle, California, USA, Version: 6 and 7). T-test was used to calculate statistical significance.

Example 9: Humanized NRG Mice Infected with the EBV-M81/fLuc2 Strain and Treated with Sorted CAR⁺CD8⁺ Derived from 7A1-gp350CAR-T (CD28z) Cells In this experiment, CAR⁺CD8⁺ cells were selected as a single population by sorting and used therapeutically after pre-established EBV-M81/fLuc2 infection. The CAR construct employed was #3 according to FIG. 8, namely "gp350CAR7B(S.28.z)" derived from the 7A1 antibody, comprising the an IgHL-VH-G4S-VL scFV, an IgG Fc CH3 spacer and CD28-CD34ζ signaling domain. All mice used in the study showed long-term reconstitution with human CD45⁺ or CD8⁺ T cells (FIG. 10B, C). EBV infection and viral distribution was detectable in all mice initially in spleen and then spreading systemically (particularly towards anatomical regions corresponding to liver and salivary glands) (FIG. 10D). Compared with control mice, treated mice showed lower EBV infection and spread at week 6 and 8 of the experiment, i.e., after the second administration with CAR⁺CD8⁺ cells. Analyses of EBV genomic copies in spleen and bone marrow by PCR showed a reduction in the average EBV infection load for CAR⁺CD8⁺ treated mice compared with control mice (approximately 50%), but the differences for liver were marginal (FIG. 10E). A correlation between the data obtained by optical imaging and PCR was observed, showing that the values of mice treated with CAR-T cells clustered apart from the values of control mice (FIG. 10F). Statistical analysis was performed using the GraphPad Prism software (Graphpad Software Inc., La Jolla, California, USA, Version: 6 and 7). T-test was used to calculate statistical significance. Corroborating the data obtained by non-invasive full-body optical imaging, explanted tissues analyzed by optical imaging showed an incidence EBV infection in control mice compared with CAR-T-treated mice in kidneys, brains and lungs (approximately doubled, FIG. 10G).

REFERENCES

Adhikary, D., U. Behrends, A. Moosmann, K. Witter, G. W. Bornkamm and J. Mautner (2006). "Control of Epstein-Barr virus infection in vitro by T helper cells specific for virion glycoproteins." J Exp Med 203(4): 995-1006.

Antsiferova, O., A. Muller, P. C. Ramer, O. Chijioke, B. Chatterjee, A. Raykova, R. Planas, M. Sospedra, A. Shumilov, M. H. Tsai, H. J. Delecluse and C. Munz (2014). "Adoptive transfer of EBV specific CD8⁺ T cell clones can transiently control EBV infection in humanized mice." PLoS Pathog 10(8): e1004333.

Daenthanasanmak, A., G. Salguero, B. S. Sundarasetty, C. Waskow, K. N. Cosgun, C. A. Guzman, P. Riese, L. Gerasch, A. Schneider, A. Ingendoh, M. Messerle, I. Gabaev, B. Woelk, E. Ruggiero, M. Schmidt, C. von Kalle, C. Figueiredo, B. Eiz-Vesper, C. von Kaisenberg, A. Ganser and R. Stripecke (2015). "Engineered dendritic cells from cord blood and adult blood accelerate effector T cell immune reconstitution against HCMV." Mol Ther Methods Clin Dev 1: 14060.

Dotti, G., S. Gottschalk, B. Savoldo and M. K. Brenner (2014). "Design and development of therapies using chimeric antigen receptor-expressing T cells." Immunol Rev 257 (1): 107-126.

Eyquem, J., J. Mansilla-Soto, T. Giavridis, S. J. van der Stegen, M. Hamieh, K. M. Cunanan, A. Odak, M. Gonen and M. Sadelain (2017). "Targeting a CAR to the TRAC locus with CRISPR/Cas9 enhances tumour rejection." Nature 543(7643): 113-117.

Mamonkin, M., R. H. Rouce, H. Tashiro and M. K. Brenner (2015). "A T-cell-directed chimeric antigen receptor for the selective treatment of T-cell malignancies." Blood 126(8): 983-992.

Papadopoulou, A., U. Gerdemann, U. L. Katari, I. Tzannou, H. Liu, C. Martinez, K. Leung, G. Carrum, A. P. Gee, J. F. Vera, R. A. Krance, M. K. Brenner, C. M. Rooney, H. E. Heslop and A. M. Leen (2014). "Activity of broad-spectrum T cells as treatment for AdV, EBV, CMV, BKV, and HHV6 infections after HSCT." Sci Transl Med 6(242): 242ra283.

Salguero, G., A. Daenthanasanmak, C. Munz, A. Raykova, C. A. Guzman, P. Riese, C. Figueiredo, F. Langer, A. Schneider, L. Macke, B. S. Sundarasetty, B. Witte, A. Ganser and R. Stripecke (2014). "Dendritic cell-mediated immune humanization of mice: implications for allogeneic and xenogeneic stem cell transplantation." J Immunol 192 (10): 4636-4647.

Xiaojun Tang, Yan Zhou, Wenjie Li, Qi Tang, Renjie Chen, Jin Zhu, Zhenqing Feng, (2014), "T cells expressing a LMP1-specific chimeric antigen receptor mediate antitumor effects against LMP1-positive nasopharyngeal carcinoma cells in vitro and in vivo", The Journal of Biomedical Research, 2014, 28(6):468-475.

Michael P. Weekes, Peter Tomasec, Edward L. Huttlin, Ceri A. Fielding, David Nusinow, Richard J. Stanton, Eddie C. Y. Wang, Rebecca Aicheler, Isa Murrell, Gavin W. G. Wilkinson, Paul J. Lehner, and Steven P. Gygi, "Quantitative Temporal Viromics: An Approach to Investigate Host-Pathogen Interaction" Cell 157, 1460-1472, Jun. 5, 2014.

Lindsey M Hutt-Fletcher (2015), "EBV glycoproteins: where are we now?" Future Virol. 2015; 10(10): 1155-1162.

Arvin A, Campadelli-Fiume G, Mocarski E, et al., editors. "Human Herpesviruses: Biology, Therapy, and Immunoprophylaxis". Cambridge: Cambridge University Press; 2007

The invention claimed is:

1. A chimeric antigen receptor polypeptide (CAR), comprising:
   i. an extracellular antigen-binding domain, comprising an antibody or antibody fragment that binds to an Epstein-Barr virus (EBV) glycoprotein 350/220 (gp350/gp220),
   ii. a transmembrane domain, and
   iii. an intracellular signaling domain,
   wherein the antigen-binding domain comprises a variable heavy chain (VH), said VH comprising heavy chain complementary determining regions H-CDR1 according to SEQ ID NO: 1 (GLSLTSN), H-CDR2 according to SEQ ID NO: 2 (WSNGG), and H-CDR3 according to SEQ ID NO: 3 (PRYNSGYFFDY), and a variable light chain (VL), said VL comprising light chain complementary determining regions L-CDR1 according to SEQ ID NO: 4 (KASESVSTRMH), L-CDR2 according to SEQ ID NO: 5 (KTSNLAS), and L-CDR3 according to SEQ ID NO: 6 (QQSWNGPLT), or
   wherein the antigen-binding domain comprises a variable heavy chain (VH), said VH comprising heavy chain complementary determining regions H-CDR1 according to SEQ ID NO: 7 (GFSLTSY), H-CDR2 according to SEQ ID NO: 8 (WSDGD), and H-CDR3 according to SEQ ID NO: 9 (LQSEDTATYYCARLQVFGYPGIRDYVMDA), and a variable light chain (VL), said VL comprising light chain complementary determining regions L-CDR1 according to SEQ ID NO: 10 (KSSQSLLSSRHQKNFLA), L-CDR2 according to SEQ ID NO: 11 (HASTRQS), and L-CDR3 according to SEQ ID NO: 12 (LQHYTSPYT).

2. The CAR polypeptide according to claim 1, wherein the EBV glycoprotein gp350/gp220 is present on the surface of EBV-infected cells.

3. The CAR polypeptide according to claim 2, wherein the EBV-infected cells are selected from the group consisting of EBV-infected cancer cells, EBV-infected B cells and EBV-infected epithelial cells.

4. The CAR polypeptide according to claim 1:
   wherein the CAR comprises a leader polypeptide positioned N-terminally of the VH and VL domains, and/or
   wherein the extracellular antigen-binding domain comprises a linker polypeptide positioned between the VH and VL domains, and/or
   comprising additionally a spacer polypeptide positioned between the extracellular antigen-binding domain and the transmembrane domain, and/or
   wherein the transmembrane domain is a CD28 or a CD8 alpha transmembrane domain; and/or
   wherein the intracellular domain comprises a CD28 or a 4-1BB co-stimulatory domain; and/or
   wherein the intracellular domain comprises a CD3 zeta chain signaling domain; and/or
   wherein the CAR comprises one or more linker polypeptides positioned between the VH and VL domains and the spacer, and/or between the spacer and the transmembrane domain.

5. The CAR polypeptide according to claim 4, wherein the leader polypeptide is an IgHL leader, wherein the linker is a G4S linker, and wherein the spacer is an IgG1 CH3 or a IgG1 CH2-CH3 spacer.

6. An isolated nucleic acid molecule, comprising a nucleotide sequence which encodes a CAR polypeptide according to claim 1.

7. A genetically modified immune cell comprising a nucleic acid molecule according to claim 6 and/or expressing a CAR according to claim 1.

8. The genetically modified immune cell according to claim 7, wherein the immune cell is selected from the group consisting of a T lymphocyte, an NK cell, a macrophage, a dendritic cell, a cytotoxic T lymphocyte and a T helper cell.

9. A method for the treatment of a medical condition associated with an EBV infection in a subject comprising administering to the subject a genetically modified immune cell according to claim 7.

10. The method according to claim 9, wherein the medical condition is an EBV-associated cancer.

11. The method according to claim 10, wherein the medical condition is selected from the group consisting of a lymphoproliferative disorder (LPD), B-cell lymphoma, Burkitt lymphoma (BL), Hodgkin lymphoma (HL), a diffuse large B cell lymphoma (DLBCL), a post-transplant lymphoproliferative disorder (PTLD), an epithelial carcinoma, a lymphoepithelioma, a carcinoma with lymphoid stroma and a glioma.

12. The method according to claim 9, wherein the medical condition associated with EBV infection is chronic active EBV infection (CAEBV) or primary EBV infection.

13. The method according to claim 9 for use in the treatment of immune deficient or immune compromised patients after chemotherapy, radiation, immune suppression or transplantation.

* * * * *